(12) United States Patent
Chau et al.

(10) Patent No.: US 8,273,540 B2
(45) Date of Patent: Sep. 25, 2012

(54) METHODS AND COMPOSITIONS RELATING TO E3 RING-E2 FUSION PROTEINS

(75) Inventors: Vincent Chau, Hershey, PA (US); Catherine S. Coleman, Hershey, PA (US); Kristine C. Olson, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 327 days.

(21) Appl. No.: 12/576,704

(22) Filed: Oct. 9, 2009

(65) Prior Publication Data

US 2010/0092998 A1   Apr. 15, 2010

Related U.S. Application Data

(60) Provisional application No. 61/104,079, filed on Oct. 9, 2008.

(51) Int. Cl.
| | |
|---|---|
| G01N 33/53 | (2006.01) |
| C12N 9/00 | (2006.01) |
| C12N 15/00 | (2006.01) |
| C12P 21/06 | (2006.01) |
| C07H 21/04 | (2006.01) |
| C07K 1/00 | (2006.01) |

(52) U.S. Cl. ..... 435/7.1; 435/183; 435/69.1; 435/320.1; 536/23.1; 536/23.2; 536/23.4; 530/350

(58) Field of Classification Search ............. 435/7.1, 435/183, 69.1, 320.1; 536/23.1, 23.2, 23.4; 530/350

See application file for complete search history.

(56) References Cited

U.S. PATENT DOCUMENTS

| | | | |
|---|---|---|---|
| 6,737,244 | B2 | 5/2004 | Issakani et al. |
| 7,132,234 | B2 | 11/2006 | Lu et al. |
| 2002/0164763 | A1 | 11/2002 | Kapeller-Libermann |
| 2008/0090249 | A1* | 4/2008 | Weissman et al. ............. 435/7.1 |

OTHER PUBLICATIONS

Chen et al., The activity of a human endoplasmic reticulum-associated degradation E3, gp78, requires its Cue domain, RING finger, and an E2-binding site. PNAS., 2006, vol. 103 (2): 341-346.*
Joazeiro et al., The tyrosine kinase negative regulator c-Cbl as a RING-type, E2-dependent ubiquitin-protein ligase. Science, 1999, vol. 286: 309-312.*
Kostova et al., Ubiquitin ligases, critical mediators of endoplasmic-associated degradation. Seminars in Cell & Developmental Biology, 2007, vol. 18: 770-779.*
Yamazaki et al., Bacterial expression of the *Saccharomyces cerevisiae* ubiquitin-conjugating enzyme Ubc7. Protein Expression and Purification, 1996, vol. 7: 122-127.*
Sun, Y., Targeting E3 Ubiquitin Ligases for Cancer Therapy, *Cancer Biology & Therapy*, 2(6): 623-29, Nov./Dec. 2003.
Burger, A. et al., The Ubiquitin-Mediated Protein Degradation Pathway in Cancer: Therapeutic Implications, *European Journal of Cancer*, 40(15): 2217-29, Oct. 2004.
van Wijk, S. et al., A comprehensive framework of E2-Ring E3 interactions of the human ubiquitin-proteasome system, *Molecular Systems Biology*, 5, Article 295: Aug. 2-4, 2009.

* cited by examiner

*Primary Examiner* — Ganapathirama Raghu
(74) *Attorney, Agent, or Firm* — Gifford, Krass, Sprinkle, Anderson & Citkowski, P.C.

(57) ABSTRACT

Compositions are provided according to embodiments of the present invention which include an isolated fusion protein including an E3 protein RING motif bonded to an UCE E2 protein. In preferred embodiments, the C-terminus of the E3 protein RING motif is bonded to the N-terminus of the UCE E2 protein by an intervening peptide linker. Optionally, the peptide linker is 5-50 amino acids. Preferred is a peptide linker of 15-20 amino acids. Methods of identifying ubiquitylation modulators are provided according to embodiments of the present invention which include contacting an isolated fusion protein including an E3 protein RING motif bonded to an UCE E2 protein with a ubiquitylation substrate in the presence of a test substance. Ubiquitylation of the ubiquitylation substrate is then detected to determine the effect of the test substance on ubiquitylation of the ubiquitylation substrate.

11 Claims, 6 Drawing Sheets

|  |  |  |  |  |
|---|---|---|---|---|
| gp78/AMFR | : | CAICWDS--MQA-ARKLPCGHL------ | ------FHNSCLRSWLEQD-------TSCPTC | SEQ ID NO: 8 |
| TRC8 | : | CAICYHEFTTSA--RITPCNHY------ | ------FHALCLRKWLYIQ-------DTCPMC | SEQ ID NO: 38 |
| HRD1 | : | CIICREE---MVTGAKRLPCNHI----- | ------FHTSCLRSWFQRQ-------QTCPTC | SEQ ID NO: 56 |
| RNF38 | : | CVVCMCDFESRQLLRVLPCNHE------ | ------FHAKCVDKWLKAN-------RTCPIC | SEQ ID NO: 26 |
| RNF111 | : | CTICLSILEEGEDVRRLPCMHL------ | ------FHQVCVDQWLITN-------KKCPIC | SEQ ID NO: 76 |
| I RNF126.2 | : | CPVCKDDYALGERVRQLPCNHL------ | ------FHDGCIVPWLEQH-------DSCPVC | SEQ ID NO: 50 |
| RNF133 | : | CVICFERYKPNDIVRILTCKHF------ | ------FHKNCIDPWILPH-------GTCPIC | SEQ ID NO: 77 |
| RNF148 | : | CVVCFDTYKPQDVVRILTCKHF------ | ------FHKACIDPWLLAH-------RTCPMC | SEQ ID NO: 78 |
| RNF128 | : | CAVCIELYKPNDLVRILTCNHI------ | ------FHKTCVDPWLLEH-------RTCPMC | SEQ ID NO: 79 |
| RNFX2 | : | CAICLDEYEEGDQLKILPCSHT------ | ------YHCKCIDPWFSQAP------RRSCPVC | SEQ ID NO: 44 |
| RNF13 | : | CAICLDEYEDGDKLRILPCSHA------ | ------YHCKCVDPWLTKTK------KTCPVC | SEQ ID NO: 20 |
| MARCH1 | : | CRICHCEGDEES-PLITPCRCTGTLRFVHQSCLHQWIKSSDT------RCCELC | SEQ ID NO: 62 |
| II MARCH8 | : | CRICHCEGDDES-PLITPCHCTGSLHFVHQACLQQWIKSSDT------RCCELC | SEQ ID NO: 80 |
| MARCH6/TEB | : | CRVCRSEGTPEK-PLYHPCVCTGSIKFIHQECLVQWLKHSRK------EYCELC | SEQ ID NO: 32 |
| MARCH7/AXO | : | CRICQMAAASSSNLLIEPCKCTGSLQYVHQDCMKKWLQAKINSGSSLEAVTTCELC | SEQ ID NO: 81 |
| III RNF26 | : | CVICOD---QSKTVLLLPCRHLC----LCQACTEILMRHPV-------YHRNCPLC | SEQ ID NO: 82 |

FIG. 3

SEQUENCE LISTING

```
<160> NUMBER OF SEQ ID NOS: 82

<210> SEQ ID NO 1
<211> LENGTH: 165
<212> TYPE: PRT
<213> ORGANISM: Homo sapiens

<400> SEQUENCE: 1

Met Ala Gly Thr Ala Leu Lys Arg Leu Met Ala Glu Tyr Lys Gln Leu
1               5                   10                  15

Thr Leu Asn Pro Pro Glu Gly Ile Val Ala Gly Pro Met Asn Glu Glu
            20                  25                  30

Asn Phe Phe Glu Trp Glu Ala Leu Ile Met Gly Pro Glu Asp Thr Cys
        35                  40                  45

Phe Glu Phe Gly Val Phe Pro Ala Ile Leu Ser Phe Pro Leu Asp Tyr
    50                  55                  60

Pro Leu Ser Pro Pro Lys Met Arg Phe Thr Cys Glu Met Phe His Pro
65                  70                  75                  80

Asn Ile Tyr Pro Asp Gly Arg Val Cys Ile Ser Ile Leu His Ala Pro
                85                  90                  95

Gly Asp Asp Pro Met Gly Tyr Glu Ser Ser Ala Glu Arg Trp Ser Pro
            100                 105                 110

Val Gln Ser Val Glu Lys Ile Leu Leu Ser Val Val Ser Met Leu Ala
        115                 120                 125

Glu Pro Asn Asp Glu Ser Gly Ala Asn Val Asp Ala Ser Lys Met Trp
    130                 135                 140

Arg Asp Asp Arg Glu Gln Phe Tyr Lys Ile Ala Lys Gln Ile Val Gln
145                 150                 155                 160

Lys Ser Leu Gly Leu
                165

<210> SEQ ID NO 2
<211> LENGTH: 498
<212> TYPE: DNA
<213> ORGANISM: Homo sapiens
```

<400> SEQUENCE: 2

| | | | | | |
|---|---|---|---|---|---|
| atggcgggga ccgcgctcaa gaggctgatg gccgagtaca acaattaac actgaatcct | | | | | 60 |
| ccggaaggaa ttgtagcagg ccccatgaat gaagagaact ttttttgaatg ggaggcattg | | | | | 120 |
| atcatgggcc cagaagacac ctgctttgag tttggtgttt ttcctgccat cctgagtttc | | | | | 180 |
| ccacttgatt acccgttaag tcccccaaag atgagattta cctgtgagat gtttcatccc | | | | | 240 |
| aacatctacc ctgatgggag agtctgcatt ccatcctcc acgcgccagg cgatgacccc | | | | | 300 |
| atgggctacg agagcagcgc ggagcggtgg agtcctgtgc agagtgtgga aagatcctg | | | | | 360 |
| ctgtcggtgg tgagcatgct ggcagagccc aatgacgaaa gtggagctaa cgtggatgcg | | | | | 420 |
| tccaaaatgt ggcgcgatga ccgggagcag ttctataaga ttgccaagca gatcgtccag | | | | | 480 |
| aagtctctgg gactgtga | | | | | 498 |

<210> SEQ ID NO 3
<211> LENGTH: 200
<212> TYPE: PRT
<213> ORGANISM: Homo sapiens

<400> SEQUENCE: 3

```
Met Ala Asn Ile Ala Val Gln Arg Ile Lys Arg Glu Phe Lys Glu Val
1               5                   10                  15

Leu Lys Ser Glu Glu Thr Ser Lys Asn Gln Ile Lys Val Asp Leu Val
            20                  25                  30

Asp Glu Asn Phe Thr Glu Leu Arg Gly Glu Ile Ala Gly Pro Pro Asp
        35                  40                  45

Thr Pro Tyr Glu Gly Gly Arg Tyr Gln Leu Glu Ile Lys Ile Pro Glu
    50                  55                  60

Thr Tyr Pro Phe Asn Pro Pro Lys Val Arg Phe Ile Thr Lys Ile Trp
65                  70                  75                  80

His Pro Asn Ile Ser Ser Val Thr Gly Ala Ile Cys Leu Asp Ile Leu
                85                  90                  95

Lys Asp Gln Trp Ala Ala Ala Met Thr Leu Arg Thr Val Leu Leu Ser
            100                 105                 110

Leu Gln Ala Leu Leu Ala Ala Ala Glu Pro Asp Asp Pro Gln Asp Ala
        115                 120                 125

Val Val Ala Asn Gln Tyr Lys Gln Asn Pro Glu Met Phe Lys Gln Thr
    130                 135                 140

Ala Arg Leu Trp Ala His Val Tyr Ala Gly Ala Pro Val Ser Ser Pro
145                 150                 155                 160

Glu Tyr Thr Lys Lys Ile Glu Asn Leu Cys Ala Met Gly Phe Asp Arg
                165                 170                 175

Asn Ala Val Ile Val Ala Leu Ser Ser Lys Ser Trp Asp Val Glu Thr
            180                 185                 190

Ala Thr Glu Leu Leu Leu Ser Asn
        195                 200
```

<210> SEQ ID NO 4
<211> LENGTH: 603
<212> TYPE: DNA
<213> ORGANISM: Homo sapiens

<400> SEQUENCE: 4

| | | | | | |
|---|---|---|---|---|---|
| atggccaaca tcgcggtgca gcgaatcaag cgggagttca aggaggtgct gaagagcgag | | | | | 60 |
| gagacgagca aaaatcaaat taagtagat cttgtagatg agaattttac agaattaaga | | | | | 120 |

| | |
|---|---|
| ggagaaatag caggacctcc agacacacca tatgaaggag gaagatacca actagagata | 180 |
| aaaataccag aaacataccc atttaatccc cctaaggtcc ggtttatcac taaaatatgg | 240 |
| catcctaata ttagttccgt cacaggggct atttgtttgg atatcctgaa agatcaatgg | 300 |
| gcagctgcaa tgactctccg cacggtatta ttgtcattgc aagcactatt ggcagctgca | 360 |
| gagccagatg atccacagga tgctgtagta gcaaatcagt acaaacaaaa tcccgaaatg | 420 |
| ttcaaacaga cagctcgact ttgggcacat gtgtatgctg agcaccagt ttctagtcca | 480 |
| gaatacacca aaaaaataga aaacctatgt gctatgggct ttgataggaa tgcagtaata | 540 |
| gtggccttgt cttcaaaatc atgggatgta gagactgcaa cagaattgct tctgagtaac | 600 |
| tga | 603 |

<210> SEQ ID NO 5
<211> LENGTH: 236
<212> TYPE: PRT
<213> ORGANISM: Homo sapiens

<400> SEQUENCE: 5

Met Ala Arg Pro Leu Val Pro Ser Ser Gln Lys Ala Leu Leu Leu Glu
1               5                   10                  15

Leu Lys Gly Leu Gln Glu Glu Pro Val Glu Gly Phe Arg Val Thr Leu
            20                  25                  30

Val Asp Glu Gly Asp Leu Tyr Asn Trp Glu Val Ala Ile Phe Gly Pro
        35                  40                  45

Pro Asn Thr Tyr Tyr Glu Gly Gly Tyr Phe Lys Ala Arg Leu Lys Phe
    50                  55                  60

Pro Ile Asp Tyr Pro Tyr Ser Pro Pro Ala Phe Arg Phe Leu Thr Lys
65                  70                  75                  80

Met Trp His Pro Asn Ile Tyr Glu Thr Gly Asp Val Cys Ile Ser Ile
                85                  90                  95

Leu His Pro Pro Val Asp Asp Pro Gln Ser Gly Glu Leu Pro Ser Glu
            100                 105                 110

Arg Trp Asn Pro Thr Gln Asn Val Arg Thr Ile Leu Leu Ser Val Ile
        115                 120                 125

Ser Leu Leu Asn Glu Pro Asn Thr Phe Ser Pro Ala Asn Val Asp Ala
    130                 135                 140

Ser Val Met Tyr Arg Lys Trp Lys Glu Ser Lys Gly Lys Asp Arg Glu
145                 150                 155                 160

Tyr Thr Asp Ile Ile Arg Lys Gln Val Leu Gly Thr Lys Val Asp Ala
                165                 170                 175

Glu Arg Asp Gly Val Lys Val Pro Thr Thr Leu Ala Glu Tyr Cys Val
            180                 185                 190

Lys Thr Lys Ala Pro Ala Pro Asp Glu Gly Ser Asp Leu Phe Tyr Asp
        195                 200                 205

Asp Tyr Tyr Glu Asp Gly Glu Val Glu Glu Ala Asp Ser Cys Phe
    210                 215                 220

Gly Asp Asp Glu Asp Asp Ser Gly Thr Glu Glu Ser
225                 230                 235

<210> SEQ ID NO 6
<211> LENGTH: 708
<212> TYPE: DNA
<213> ORGANISM: Homo sapiens

<400> SEQUENCE: 6

| | |
|---|---|
| atggctcggc cgctagtgcc cagctcgcag aaggcgctgc tgctggagct caaggggctg | 60 |

```
caggaagagc cggtcgaggg attccgcgtg acactggtgg acgagggcga tctatacaac    120
tgggaggtgg ccatcttcgg ccccccaac acctactacg agggcggcta cttcaaggcg     180
cgcctcaagt tccccatcga ctacccatac tctccaccag cctttcggtt cctgaccaag    240
atgtggcacc ctaacatcta cgagacgggg gacgtgtgta tctccatcct ccacccgccg    300
gtggacgacc cccagagcgg ggagctgccc tcagagaggt ggaaccccac gcagaacgtc    360
aggaccattc tcctgagtgt gatctccctc ctgaacgagc ccaacacctt ctcgcccgca    420
aacgtggacg cctccgtgat gtacaggaag tggaaagaga gcaaggggaa ggatcgggag    480
tacacagaca tcatccggaa gcaggtcctg gggaccaagg tggacgcgga gcgtgacggc    540
gtgaaggtgc ccaccacgct ggccgagtac tgcgtgaaga ccaaggcgcc ggcgcccgac    600
gagggctcag acctcttcta cgacgactac tacgaggacg cgaggtggga ggaggaggcc    660
gacagctgct cggggacga tgaggatgac tctggcacgg aggagtcc               708
```

```
<210> SEQ ID NO 7
<211> LENGTH: 76
<212> TYPE: PRT
<213> ORGANISM: Homo sapiens

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 8
<211> LENGTH: 38
<212> TYPE: PRT
<213> ORGANISM: Homo sapiens

<400> SEQUENCE: 8

Cys Ala Ile Cys Trp Asp Ser Met Gln Ala Ala Arg Lys Leu Pro Cys
1               5                   10                  15

Gly His Leu Phe His Asn Ser Cys Leu Arg Ser Trp Leu Glu Gln Asp
            20                  25                  30

Thr Ser Cys Pro Thr Cys
35

<210> SEQ ID NO 9
<211> LENGTH: 114
<212> TYPE: DNA
<213> ORGANISM: Homo sapiens

<400> SEQUENCE: 9
tgtgccatct gttgggactc catgcaggct gcgcggaaac tgccctgtgg acatcttttc    60
cacaactcct gtcttcgttc ctggctagaa caagacacct cctgtccaac atgc         114

<210> SEQ ID NO 10
<211> LENGTH: 72
<212> TYPE: PRT
<213> ORGANISM: Homo sapiens
```

-continued

<400> SEQUENCE: 10

Met Glu Ala Arg Phe Ala Val Ala Thr Pro Glu Glu Leu Ala Val Asn
1               5                   10                  15

Asn Asp Asp Cys Ala Ile Cys Trp Asp Ser Met Gln Ala Ala Arg Lys
            20                  25                  30

Leu Pro Cys Gly His Leu Phe His Asn Ser Cys Leu Arg Ser Trp Leu
        35                  40                  45

Glu Gln Asp Thr Ser Cys Pro Thr Cys Arg Met Ser Leu Asn Ile Ala
    50                  55                  60

Asp Asn Asn Arg Val Arg Glu Glu
65                  70

<210> SEQ ID NO 11
<211> LENGTH: 216
<212> TYPE: DNA
<213> ORGANISM: Homo sapiens

<400> SEQUENCE: 11
atggaggcca ggtttgcagt tgcaactcca gaggagctgg ctgtcaacaa tgacgactgt     60
gccatctgtt gggactccat gcaggctgcg cggaaactgc cctgtggaca tcttttccac   120
aactcctgtc ttcgttcctg gctagaacaa gacacctcct gtccaacatg cagaatgtct   180
cttaatattg ccgacaataa tcgtgtcagg gaagaa                             216

<210> SEQ ID NO 12
<211> LENGTH: 242
<212> TYPE: PRT
<213> ORGANISM: Artificial Sequence
<220> FEATURE:
<223> OTHER INFORMATION: Fusion protein including the gp78 E3 RING
      motif, Ubc7 UCE E2 protein and peptide linker

<400> SEQUENCE: 12

Met Glu Ala Arg Phe Ala Val Ala Thr Pro Glu Glu Leu Ala Val Asn
1               5                   10                  15

Asn Asp Asp Cys Ala Ile Cys Trp Asp Ser Met Gln Ala Ala Arg Lys
            20                  25                  30

Leu Pro Cys Gly His Leu Phe His Asn Ser Cys Leu Arg Ser Trp Leu
        35                  40                  45

Glu Gln Asp Thr Ser Cys Pro Thr Cys Arg Met Ser Leu Asn Ile Ala
    50                  55                  60

Asp Asn Asn Arg Val Arg Glu Glu Gly Thr Gly Ser His Met Ala Gly
65                  70                  75                  80

Thr Ala Leu Lys Arg Leu Met Ala Glu Tyr Lys Gln Leu Thr Leu Asn
                85                  90                  95

Pro Pro Glu Gly Ile Val Ala Gly Pro Met Asn Glu Glu Asn Phe Phe
            100                 105                 110

Glu Trp Glu Ala Leu Ile Met Gly Pro Glu Asp Thr Cys Phe Glu Phe
        115                 120                 125

Gly Val Phe Pro Ala Ile Leu Ser Phe Pro Leu Asp Tyr Pro Leu Ser
    130                 135                 140

Pro Pro Lys Met Arg Phe Thr Cys Glu Met Phe His Pro Asn Ile Tyr
145                 150                 155                 160

Pro Asp Gly Arg Val Cys Ile Ser Ile Leu His Ala Pro Gly Asp Asp
                165                 170                 175

Pro Met Gly Tyr Glu Ser Ser Ala Glu Arg Trp Ser Pro Val Gln Ser
            180                 185                 190

Val Glu Lys Ile Leu Leu Ser Val Ser Met Leu Ala Glu Pro Asn
            195                 200                 205

Asp Glu Ser Gly Ala Asn Val Asp Ala Ser Lys Met Trp Arg Asp Asp
        210                 215                 220

Arg Glu Gln Phe Tyr Lys Ile Ala Lys Gln Ile Val Gln Lys Ser Leu
225                 230                 235                 240

Gly Leu

<210> SEQ ID NO 13
<211> LENGTH: 729
<212> TYPE: DNA
<213> ORGANISM: Artificial Sequence
<220> FEATURE:
<223> OTHER INFORMATION: cDNA sequencing encoding a fusion protein
      including the gp78 E3 RING motif, Ubc7 UCE E2 protein and a
      peptide linker

<400> SEQUENCE: 13
atggaggcca ggtttgcagt tgcaactcca gaggagctgg ctgtcaacaa tgacgactgt      60
gccatctgtt gggactccat gcaggctgcg cggaaactgc cctgtggaca tcttttccac     120
aactcctgtc ttcgttcctg gctagaacaa gacacctcct gtccaacatg cagaatgtct     180
cttaatattg ccgacaataa tcgtgtcagg gaagaaggta ccggatccca tatggcgggg     240
accgcgctca gaggctgat ggccgagtac aaacaattaa cactgaatcc tccggaagga      300
attgtagcag gccccatgaa tgaagagaac ttttttgaat gggaggcatt gatcatgggc     360
ccagaagaca cctgctttga gtttggtgtt tttcctgcca cctgagtttt cccacttgat     420
tacccgttaa gtcccccaaa gatgagattt acctgtgaga tgtttcatcc caacatctac     480
cctgatggga gagtctgcat ttccatcctc cacgcgccag gcgatgaccc catgggctac     540
gagagcagcg cggagcggtg gagtcctgtg cagagtgtgg agaagatcct gctgtcggtg     600
gtgagcatgc tggcagagcc caatgacgaa agtggagcta acgtggatgc gtccaaaatg     660
tggcgcgatg accgggagca gttctataag attgccaagc agatcgtcca gaagtctctg     720
ggactgtga                                                             729

<210> SEQ ID NO 14
<211> LENGTH: 55
<212> TYPE: PRT
<213> ORGANISM: Saccharomyces cerevisiae

<400> SEQUENCE: 14

Cys Arg Ile Cys Arg Gly Glu Ala Thr Glu Asp Asn Pro Leu Phe His
1                5                  10                  15

Pro Cys Lys Cys Arg Gly Ser Ile Lys Tyr Met His Glu Ser Cys Leu
            20                  25                  30

Leu Glu Trp Val Ala Ser Lys Asn Ile Asp Ile Ser Lys Pro Gly Ala
        35                  40                  45

Asp Val Lys Cys Asp Ile Cys
    50                  55

<210> SEQ ID NO 15
<211> LENGTH: 165
<212> TYPE: DNA
<213> ORGANISM: Saccharomyces cerevisiae

<400> SEQUENCE: 15
tgccgtattt gtcgtggaga agctactgag gacaatcctc ttttccatcc ttgtaaatgc      60

```
aggggctcaa ttaaatacat gcatgaatcc tgtctgttag aatgggtagc ttcaaaaaat    120
atagacattt caaaaccagg cgcggatgtt aaatgtgaca tctgt                    165
```

<210> SEQ ID NO 16
<211> LENGTH: 91
<212> TYPE: PRT
<213> ORGANISM: Saccharomyces cerevisiae

<400> SEQUENCE: 16

```
Met Ala Asn Glu Glu Thr Asp Thr Ala Thr Phe Asn Asp Asp Ala Pro
 1               5                  10                  15

Ser Gly Ala Thr Cys Arg Ile Cys Arg Gly Glu Ala Thr Glu Asp Asn
            20                  25                  30

Pro Leu Phe His Pro Cys Lys Cys Arg Gly Ser Ile Lys Tyr Met His
        35                  40                  45

Glu Ser Cys Leu Leu Glu Trp Val Ala Ser Lys Asn Ile Asp Ile Ser
    50                  55                  60

Lys Pro Gly Ala Asp Val Lys Cys Asp Ile Cys His Tyr Pro Ile Gln
65                  70                  75                  80

Phe Lys Thr Ile Tyr Ala Glu Asn Met Pro Glu
                85                  90
```

<210> SEQ ID NO 17
<211> LENGTH: 273
<212> TYPE: DNA
<213> ORGANISM: Saccharomyces cerevisiae

<400> SEQUENCE: 17

```
atggcaaacg aggaaacaga taccgccact ttcaatgatg atgcgccatc cggcgccacc     60
tgccgtattt gtcgtggaga agctactgag gacaatcctc ttttccatcc ttgtaaatgc    120 agggggctcaa ttaaatacat gcatgaatcc tgtctgttag aatgggtagc ttcaaaaaat   180
atagacattt caaaaccagg cgcggatgtt aaatgtgaca tctgtcacta tcccattcaa    240
ttcaaaacga tatatgcgga aacatgcccc gaa                                  273
```

<210> SEQ ID NO 18
<211> LENGTH: 261
<212> TYPE: PRT
<213> ORGANISM: Artificial Sequence
<220> FEATURE:
<223> OTHER INFORMATION: fusion protein including the Doa10 E3 RING
      motif, Ubc7 UCE E2 protein and peptide linker

<400> SEQUENCE: 18

```
Met Ala Asn Glu Glu Thr Asp Thr Ala Thr Phe Asn Asp Asp Ala Pro
 1               5                  10                  15

Ser Gly Ala Thr Cys Arg Ile Cys Arg Gly Glu Ala Thr Glu Asp Asn
            20                  25                  30

Pro Leu Phe His Pro Cys Lys Cys Arg Gly Ser Ile Lys Tyr Met His
        35                  40                  45

Glu Ser Cys Leu Leu Glu Trp Val Ala Ser Lys Asn Ile Asp Ile Ser
    50                  55                  60

Lys Pro Gly Ala Asp Val Lys Cys Asp Ile Cys His Tyr Pro Ile Gln
65                  70                  75                  80

Phe Lys Thr Ile Tyr Ala Glu Asn Met Pro Glu Gly Thr Gly Ser His
                85                  90                  95

Met Ala Gly Thr Ala Leu Lys Arg Leu Met Ala Glu Tyr Lys Gln Leu
            100                 105                 110
```

```
Thr Leu Asn Pro Pro Glu Gly Ile Val Ala Gly Pro Met Asn Glu Glu
        115                 120                 125

Asn Phe Phe Glu Trp Glu Ala Leu Ile Met Gly Pro Glu Asp Thr Cys
    130                 135                 140

Phe Glu Phe Gly Val Phe Pro Ala Ile Leu Ser Phe Pro Leu Asp Tyr
145                 150                 155                 160

Pro Leu Ser Pro Pro Lys Met Arg Phe Thr Cys Glu Met Phe His Pro
                165                 170                 175

Asn Ile Tyr Pro Asp Gly Arg Val Cys Ile Ser Ile Leu His Ala Pro
            180                 185                 190

Gly Asp Asp Pro Met Gly Tyr Glu Ser Ser Ala Glu Arg Trp Ser Pro
        195                 200                 205

Val Gln Ser Val Glu Lys Ile Leu Leu Ser Val Ser Met Leu Ala
210                 215                 220

Glu Pro Asn Asp Glu Ser Gly Ala Asn Val Asp Ala Ser Lys Met Trp
225                 230                 235                 240

Arg Asp Asp Arg Glu Gln Phe Tyr Lys Ile Ala Lys Gln Ile Val Gln
                245                 250                 255

Lys Ser Leu Gly Leu
            260
```

<210> SEQ ID NO 19
<211> LENGTH: 786
<212> TYPE: DNA
<213> ORGANISM: Artificial Sequence
<220> FEATURE:
<223> OTHER INFORMATION: cDNA sequence encoding a fusion protein
      including the E3 RING motif of Doa10, Ubc7 UCE E2 protein and a
      peptide linker

<400> SEQUENCE: 19

```
atggcaaacg aggaaacaga taccgccact ttcaatgatg atgcgccatc cggcgccacc      60
tgccgtattt gtcgtggaga agctactgag acaatcctc ttttccatcc ttgtaaatgc      120
agggctcaa ttaaatacat gcatgaatcc tgtctgttag aatgggtagc ttcaaaaaat      180
atagacattt caaaaccagg cgcggatgtt aaatgtgaca tctgtcacta tcccattcaa      240
ttcaaaacga tatatgcgga aaacatgccc gaaggtaccg atcccatat ggcggggacc      300
gcgctcaaga ggctgatggc cgagtacaaa caattaacac tgaatcctcc ggaaggaatt      360
gtagcaggcc ccatgaatga agagaacttt tttgaatggg aggcattgat catgggccca      420
gaagacacct gctttgagtt tggtgttttt cctgccatcc tgagtttccc acttgattac      480
ccgttaagtc ccccaaagat gagatttacc tgtgagatgt tcatcccaa catctaccct      540
gatgggagag tctgcatttc catcctccac gcgccaggcg atgacccat gggctacgag      600
agcagcgcgg agcggtggag tcctgtgcag agtgtggaga agatcctgct gtcggtggtg      660
agcatgctgg cagagcccaa tgacgaaagt ggagctaacg tggatgcgtc caaaatgtgg      720
cgcgatgacc gggagcagtt ctataagatt gccaagcaga tcgtccagaa gtctctggga      780
ctgtga                                                                 786
```

<210> SEQ ID NO 20
<211> LENGTH: 42
<212> TYPE: PRT
<213> ORGANISM: Homo sapiens

<400> SEQUENCE: 20

```
Cys Ala Ile Cys Leu Asp Glu Tyr Glu Asp Gly Asp Lys Leu Arg Ile
1               5                   10                  15
```

```
Leu Pro Cys Ser His Ala Tyr His Cys Lys Cys Val Asp Pro Trp Leu
            20                  25                  30

Thr Lys Thr Lys Lys Thr Cys Pro Val Cys
            35                  40

<210> SEQ ID NO 21
<211> LENGTH: 126
<212> TYPE: DNA
<213> ORGANISM: Homo sapiens

<400> SEQUENCE: 21
tgtgccattt gtttggatga gtatgaagat ggagacaaac tcagaatcct tccctgttcc      60
catgcttatc attgcaagtg tgtagaccct tggctaacta aaaccaaaaa aacctgtcca     120
gtgtgc                                                                126

<210> SEQ ID NO 22
<211> LENGTH: 73
<212> TYPE: PRT
<213> ORGANISM: Homo sapiens

<400> SEQUENCE: 22

Met Gln Leu Lys Lys Leu Pro Val His Lys Phe Lys Lys Gly Asp Glu
1               5                   10                  15

Tyr Asp Val Cys Ala Ile Cys Leu Asp Glu Tyr Glu Asp Gly Asp Lys
            20                  25                  30

Leu Arg Ile Leu Pro Cys Ser His Ala Tyr His Cys Lys Cys Val Asp
        35                  40                  45

Pro Trp Leu Thr Lys Thr Lys Lys Thr Cys Pro Val Cys Lys Gln Lys
    50                  55                  60

Val Val Pro Ser Gln Gly Asp Ser Asp
65                  70

<210> SEQ ID NO 23
<211> LENGTH: 219
<212> TYPE: DNA
<213> ORGANISM: Homo sapiens

<400> SEQUENCE: 23
atgcaactta agaaacttcc tgtacataaa ttcaagaaag gagatgagta tgatgtatgt      60
gccatttgtt tggatgagta tgaagatgga gacaaactca gaatccttcc ctgttcccat     120
gcttatcatt gcaagtgtgt agaccctggg ctaactaaaa ccaaaaaaac ctgtccagtg     180
tgcaagcaaa aagttgttcc ttctcaaggc gattcagac                            219

<210> SEQ ID NO 24
<211> LENGTH: 243
<212> TYPE: PRT
<213> ORGANISM: Artificial Sequence
<220> FEATURE:
<223> OTHER INFORMATION: fusion protein including the RNF13 E3 RING
      motif, Ubc7 UCE E2 protein and peptide linker

<400> SEQUENCE: 24

Met Gln Leu Lys Lys Leu Pro Val His Lys Phe Lys Lys Gly Asp Glu
1               5                   10                  15

Tyr Asp Val Cys Ala Ile Cys Leu Asp Glu Tyr Glu Asp Gly Asp Lys
            20                  25                  30

Leu Arg Ile Leu Pro Cys Ser His Ala Tyr His Cys Lys Cys Val Asp
        35                  40                  45
```

```
Pro Trp Leu Thr Lys Thr Lys Lys Thr Cys Pro Val Cys Lys Gln Lys
 50                  55                  60

Val Val Pro Ser Gln Gly Asp Ser Asp Gly Thr Gly Ser His Met Ala
 65                  70                  75                  80

Gly Thr Ala Leu Lys Arg Leu Met Ala Glu Tyr Lys Gln Leu Thr Leu
                 85                  90                  95

Asn Pro Pro Glu Gly Ile Val Ala Gly Pro Met Asn Glu Glu Asn Phe
                100                 105                 110

Phe Glu Trp Glu Ala Leu Ile Met Gly Pro Glu Asp Thr Cys Phe Glu
            115                 120                 125

Phe Gly Val Phe Pro Ala Ile Leu Ser Phe Pro Leu Asp Tyr Pro Leu
        130                 135                 140

Ser Pro Pro Lys Met Arg Phe Thr Cys Glu Met Phe His Pro Asn Ile
145                 150                 155                 160

Tyr Pro Asp Gly Arg Val Cys Ile Ser Ile Leu His Ala Pro Gly Asp
                165                 170                 175

Asp Pro Met Gly Tyr Glu Ser Ser Ala Glu Arg Trp Ser Pro Val Gln
            180                 185                 190

Ser Val Glu Lys Ile Leu Leu Ser Val Val Ser Met Leu Ala Glu Pro
        195                 200                 205

Asn Asp Glu Ser Gly Ala Asn Val Asp Ala Ser Lys Met Trp Arg Asp
    210                 215                 220

Asp Arg Glu Gln Phe Tyr Lys Ile Ala Lys Gln Ile Val Gln Lys Ser
225                 230                 235                 240

Leu Gly Leu

<210> SEQ ID NO 25
<211> LENGTH: 732
<212> TYPE: DNA
<213> ORGANISM: Artificial Sequence
<220> FEATURE:
<223> OTHER INFORMATION: cDNA sequence encoding a fusion protein
      including the E3 RING motif of RNF13, Ubc7 UCE E2 protein and
      peptide linker

<400> SEQUENCE: 25
atgcaactta agaaacttcc tgtacataaa ttcaagaaag gagatgagta tgatgtatgt    60
gccatttgtt tggatgagta tgaagatgga gacaaactca gaatccttcc ctgttcccat   120
gcttatcatt gcaagtgtgt agaccettgg ctaactaaaa ccaaaaaaac ctgtccagtg   180
tgcaagcaaa aagttgttcc ttctcaaggc gattcagacg gtaccggatc ccatatggcg   240
gggaccgcgc tcaagaggct gatggccgag tacaaacaat taacactgaa tcctccggaa   300
ggaattgtag caggccccat gaatgaagag aacttttttg aatgggaggc attgatcatg   360
ggcccagaag acacctgctt tgagtttggt gttttcctg ccatcctgag tttcccactt   420 gattaccegt taagtcccce aaagatgaga tttacctgtg agatgtttca tcccaacatc   480
taccctgatg ggagagtctg catttccatc ctccacgcgc aggcgatga ccccatgggc   540 tacgagagca gcgcggagcg gtggagtcct gtgcagagtg tggagaagat cctgctgtcg   600
gtggtgagca tgctggcaga gcccaatgac gaaagtggag ctaacgtgga tgcgtccaaa   660
atgtggcgcg atgaccggga gcagttctat aagattgcca agcagatcgt ccagaagtct   720
ctgggactgt ga                                                      732

<210> SEQ ID NO 26
<211> LENGTH: 41
<212> TYPE: PRT
```

<213> ORGANISM: Homo sapiens

<400> SEQUENCE: 26

Cys Val Val Cys Met Cys Asp Phe Glu Ser Arg Gln Leu Leu Arg Val
1               5                   10                  15

Leu Pro Cys Asn His Glu Phe His Ala Lys Cys Val Asp Lys Trp Leu
            20                  25                  30

Lys Ala Asn Arg Thr Cys Pro Ile Cys
        35                  40

<210> SEQ ID NO 27
<211> LENGTH: 123
<212> TYPE: DNA
<213> ORGANISM: Homo sapiens

<400> SEQUENCE: 27
tgtgtagtat gcatgtgtga ttttgagtca aggcagctac ttagagtctt accctgtaac     60
cacgagttcc atgccaagtg tgttgacaaa tggcttaagg caaatcgtac ttgcccaatt    120
tgc                                                                  123

<210> SEQ ID NO 28
<211> LENGTH: 72
<212> TYPE: PRT
<213> ORGANISM: Homo sapiens

<400> SEQUENCE: 28

Met Gln Leu Pro Ser Tyr Arg Phe Asn Pro Asn Asn His Gln Ser Glu
1               5                   10                  15

Gln Thr Leu Cys Val Val Cys Met Cys Asp Phe Glu Ser Arg Gln Leu
            20                  25                  30

Leu Arg Val Leu Pro Cys Asn His Glu Phe His Ala Lys Cys Val Asp
        35                  40                  45

Lys Trp Leu Lys Ala Asn Arg Thr Cys Pro Ile Cys Arg Ala Asp Ala
    50                  55                  60

Ser Glu Val His Arg Asp Ser Glu
65                  70

<210> SEQ ID NO 29
<211> LENGTH: 216
<212> TYPE: DNA
<213> ORGANISM: Homo sapiens

<400> SEQUENCE: 29
atgcaacttc cttcttatcg gttcaatcct aacaaccacc agtcagaaca gactttgtgt     60
gtagtatgca tgtgtgattt tgagtcaagg cagctactta gagtcttacc ctgtaaccac    120
gagttccatg ccaagtgtgt tgacaaatgg cttaaggcaa atcgtacttg cccaatttgc    180
cgagctgatg cttcagaagt gcatcgggat tcagaa                              216

<210> SEQ ID NO 30
<211> LENGTH: 242
<212> TYPE: PRT
<213> ORGANISM: Artificial Sequence
<220> FEATURE:
<223> OTHER INFORMATION: fusion protein including the RNF38 E3 RING
      motif, Ubc7 UCE E2 protein and peptide linker

<400> SEQUENCE: 30

Met Gln Leu Pro Ser Tyr Arg Phe Asn Pro Asn Asn His Gln Ser Glu
1               5                   10                  15

```
Gln Thr Leu Cys Val Val Cys Met Cys Asp Phe Glu Ser Arg Gln Leu
             20                  25                  30
Leu Arg Val Leu Pro Cys Asn His Glu Phe His Ala Lys Cys Val Asp
         35                  40                  45
Lys Trp Leu Lys Ala Asn Arg Thr Cys Pro Ile Cys Arg Ala Asp Ala
 50                  55                  60
Ser Glu Val His Arg Asp Ser Glu Gly Thr Gly Ser His Met Ala Gly
 65                  70                  75                  80
Thr Ala Leu Lys Arg Leu Met Ala Glu Tyr Lys Gln Leu Thr Leu Asn
                 85                  90                  95
Pro Pro Glu Gly Ile Val Ala Gly Pro Met Asn Glu Glu Asn Phe Phe
            100                 105                 110
Glu Trp Glu Ala Leu Ile Met Gly Pro Glu Asp Thr Cys Phe Glu Phe
        115                 120                 125
Gly Val Phe Pro Ala Ile Leu Ser Phe Pro Leu Asp Tyr Pro Leu Ser
130                 135                 140
Pro Pro Lys Met Arg Phe Thr Cys Glu Met Phe His Pro Asn Ile Tyr
145                 150                 155                 160
Pro Asp Gly Arg Val Cys Ile Ser Ile Leu His Ala Pro Gly Asp Asp
                165                 170                 175
Pro Met Gly Tyr Glu Ser Ser Ala Glu Arg Trp Ser Pro Val Gln Ser
            180                 185                 190
Val Glu Lys Ile Leu Leu Ser Val Val Ser Met Leu Ala Glu Pro Asn
        195                 200                 205
Asp Glu Ser Gly Ala Asn Val Asp Ala Ser Lys Met Trp Arg Asp Asp
210                 215                 220
Arg Glu Gln Phe Tyr Lys Ile Ala Lys Gln Ile Val Gln Lys Ser Leu
225                 230                 235                 240
Gly Leu

<210> SEQ ID NO 31
<211> LENGTH: 729
<212> TYPE: DNA
<213> ORGANISM: Artificial Sequence
<220> FEATURE:
<223> OTHER INFORMATION: cDNA sequence encoding a fusion protein
      including the E3 RING motif of RNF38, Ubc7 UCE E2 protein and
      peptide linker

<400> SEQUENCE: 31
atgcaacttc cttcttatcg gttcaatcct aacaaccacc agtcagaaca gactttgtgt      60
gtagtatgca tgtgtgattt tgagtcaagg cagctactta gagtcttacc ctgtaaccac     120
gagttccatg ccaagtgtgt tgacaaatgg cttaaggcaa atcgtacttg cccaatttgc     180
cgagctgatg cttcagaagt gcatcgggat tcagaaggta ccggatccca tatggcgggg     240
accgcgctca gaggctgat ggccgagtac aaacaattaa cactgaatcc tccgaagga      300 attgtagcag gccccatgaa tgaagagaac ttttttgaat gggaggcatt gatcatgggc     360
ccagaagaca cctgctttga gtttggtgtt tttcctgcca tcctgagttt cccacttgat     420
tacccgttaa gtccccaaa gatgagattt acctgtgaga tgtttcatcc aacatctac      480 cctgatggga gagtctgcat ttccatcctc acgcgccag gcgatgaccc catgggctac     540
gagagcagcg cggagcggtg gagtcctgtg cagagtgtgg agaagatcct gctgtcggtg     600
gtgagcatgc tggcagagcc caatgacgaa agtggagcta acgtggatgc gtccaaaatg     660
tggcgcgatg accgggagca gttctataag attgccaagc agatcgtcca gaagtctctg     720
```

<210> SEQ ID NO 32
<211> LENGTH: 47
<212> TYPE: PRT
<213> ORGANISM: Homo sapiens

<400> SEQUENCE: 32

Cys Arg Val Cys Arg Ser Glu Gly Thr Pro Glu Lys Pro Leu Tyr His
 1               5                  10                  15

Pro Cys Val Cys Thr Gly Ser Ile Lys Phe Ile His Gln Glu Cys Leu
            20                  25                  30

Val Gln Trp Leu Lys His Ser Arg Lys Glu Tyr Cys Glu Leu Cys
        35                  40                  45

<210> SEQ ID NO 33
<211> LENGTH: 141
<212> TYPE: DNA
<213> ORGANISM: Homo sapiens

<400> SEQUENCE: 33
tgtagagtgt gtcggtcaga aggaacacct gagaaaccgc tttatcatcc ttgtgtatgt      60
actggcagta ttaagtttat ccatcaagaa tgcttagttc aatggctgaa acacagtcga    120
aaagaatact gtgaattatg c                                              141

<210> SEQ ID NO 34
<211> LENGTH: 77
<212> TYPE: PRT
<213> ORGANISM: Homo sapiens

<400> SEQUENCE: 34

Met Asp Thr Ala Glu Glu Asp Ile Cys Arg Val Cys Arg Ser Glu Gly
 1               5                  10                  15

Thr Pro Glu Lys Pro Leu Tyr His Pro Cys Val Cys Thr Gly Ser Ile
            20                  25                  30

Lys Phe Ile His Gln Glu Cys Leu Val Gln Trp Leu Lys His Ser Arg
        35                  40                  45

Lys Glu Tyr Cys Glu Leu Cys Lys His Arg Phe Ala Phe Thr Pro Ile
    50                  55                  60

Tyr Ser Pro Asp Asp Ser Ser Gly Arg Ile Val Thr Asp
65                  70                  75

<210> SEQ ID NO 35
<211> LENGTH: 231
<212> TYPE: DNA
<213> ORGANISM: Homo sapiens

<400> SEQUENCE: 35
atggacaccg cggaggaaga tatatgtaga gtgtgtcggt cagaaggaac acctgagaaa      60
ccgctttatc atccttgtgt atgtactggc agtattaagt ttatccatca agaatgctta    120
gttcaatggc tgaaacacag tcgaaaagaa tactgtgaat tatgcaagca cagatttgct    180
tttacaccaa tttattctcc agatgactcg agcggccgca tcgtgactga c              231

<210> SEQ ID NO 36
<211> LENGTH: 247
<212> TYPE: PRT
<213> ORGANISM: Artificial Sequence
<220> FEATURE:
<223> OTHER INFORMATION: fusion protein including the TEB4 E3 RING
      motif, Ubc7 UCE E2 protein and peptide linker

<400> SEQUENCE: 36

```
Met Asp Thr Ala Glu Glu Asp Ile Cys Arg Val Cys Arg Ser Gly
1               5                   10                  15

Thr Pro Glu Lys Pro Leu Tyr His Pro Cys Val Cys Thr Gly Ser Ile
            20                  25                  30

Lys Phe Ile His Gln Glu Cys Leu Val Gln Trp Leu Lys His Ser Arg
            35                  40                  45

Lys Glu Tyr Cys Glu Leu Cys Lys His Arg Phe Ala Phe Thr Pro Ile
        50                  55                  60

Tyr Ser Pro Asp Asp Ser Ser Gly Arg Ile Val Thr Asp Gly Thr Gly
65                  70                  75                  80

Ser His Met Ala Gly Thr Ala Leu Lys Arg Leu Met Ala Glu Tyr Lys
                85                  90                  95

Gln Leu Thr Leu Asn Pro Pro Glu Gly Ile Val Ala Gly Pro Met Asn
            100                 105                 110

Glu Glu Asn Phe Phe Glu Trp Glu Ala Leu Ile Met Gly Pro Glu Asp
        115                 120                 125

Thr Cys Phe Glu Phe Gly Val Phe Pro Ala Ile Leu Ser Phe Pro Leu
    130                 135                 140

Asp Tyr Pro Leu Ser Pro Pro Lys Met Arg Phe Thr Cys Glu Met Phe
145                 150                 155                 160

His Pro Asn Ile Tyr Pro Asp Gly Arg Val Cys Ile Ser Ile Leu His
                165                 170                 175

Ala Pro Gly Asp Asp Pro Met Gly Tyr Glu Ser Ser Ala Glu Arg Trp
            180                 185                 190

Ser Pro Val Gln Ser Val Glu Lys Ile Leu Leu Ser Val Val Ser Met
        195                 200                 205

Leu Ala Glu Pro Asn Asp Glu Ser Gly Ala Asn Val Asp Ala Ser Lys
    210                 215                 220

Met Trp Arg Asp Asp Arg Glu Gln Phe Tyr Lys Ile Ala Lys Gln Ile
225                 230                 235                 240

Val Gln Lys Ser Leu Gly Leu
                245
```

<210> SEQ ID NO 37
<211> LENGTH: 744
<212> TYPE: DNA
<213> ORGANISM: Artificial Sequence
<220> FEATURE:
<223> OTHER INFORMATION: cDNA sequence encoding a fusion protein including the E3 RING motif of TEB4, Ubc7 UCE E2 protein and peptide linker

<400> SEQUENCE: 37

```
atggacaccg cggaggaaga tatatgtaga gtgtgtcggt cagaaggaac acctgagaaa      60
ccgctttatc atccttgtgt atgtactggc agtattaagt ttatccatca agaatgctta    120
gttcaatggc tgaaacacag tcgaaaagaa tactgtgaat tatgcaagca cagatttgct    180
tttacaccaa tttattctcc agatgactcg agcggccgca tcgtgactga cggtaccgga    240
tcccatatgg cggggaccgc gctcaagagg ctgatggccg agtacaaaca attaacactg    300
aatcctccgg aaggaattgt agcaggcccc atgaatgaag agaacttttt tgaatgggag    360
gcattgatca tgggcccaga agacacctgc tttgagtttg gtgttttcc tgccatcctg    420
agttccccac ttgattaccc gttaagtccc ccaaagatga gatttacctg tgagatgttt    480
catcccaaca tctaccctga tgggagagtc tgcatttcca tcctccacgc gccaggcgat    540
```

```
gaccccatgg gctacgagag cagcgcggag cggtggagtc ctgtgcagag tgtggagaag      600
atcctgctgt cggtggtgag catgctggca gagcccaatg acgaaagtgg agctaacgtg      660
gatgcgtcca aaatgtggcg cgatgaccgg gagcagttct ataagattgc caagcagatc      720
gtccagaagt ctctgggact gtga                                              744
```

<210> SEQ ID NO 38
<211> LENGTH: 39
<212> TYPE: PRT
<213> ORGANISM: Homo sapiens

<400> SEQUENCE: 38

```
Cys Ala Ile Cys Tyr His Glu Phe Thr Thr Ser Ala Arg Ile Thr Pro
1               5                   10                  15

Cys Asn His Tyr Phe His Ala Leu Cys Leu Arg Lys Trp Leu Tyr Ile
            20                  25                  30

Gln Asp Thr Cys Pro Met Cys
        35
```

<210> SEQ ID NO 39
<211> LENGTH: 117
<212> TYPE: DNA
<213> ORGANISM: Homo sapiens

<400> SEQUENCE: 39

```
tgtgcaatct gctatcatga gtttacaaca tctgctcgta ttacaccgtg taatcattat      60
ttccatgcac tttgccttcg gaaatggctg tacattcaag atacttgtcc aatgtgc        117
```

<210> SEQ ID NO 40
<211> LENGTH: 72
<212> TYPE: PRT
<213> ORGANISM: Homo sapiens

<400> SEQUENCE: 40

```
Met Ile Asn Ser Leu Pro Glu Ile Lys Gly Ser Arg Leu Gln Glu Ile
1               5                   10                  15

Asn Asp Val Cys Ala Ile Cys Tyr His Glu Phe Thr Thr Ser Ala Arg
            20                  25                  30

Ile Thr Pro Cys Asn His Tyr Phe His Ala Leu Cys Leu Arg Lys Trp
        35                  40                  45

Leu Tyr Ile Gln Asp Thr Cys Pro Met Cys His Gln Lys Val Tyr Ile
    50                  55                  60

Glu Asp Asp Ile Lys Asp Asn Ser
65                  70
```

<210> SEQ ID NO 41
<211> LENGTH: 216
<212> TYPE: DNA
<213> ORGANISM: Homo sapiens

<400> SEQUENCE: 41

```
atgattaatt cacttcctga aataaaaggg agccgcttac aagaaataaa tgatgtatgt      60
gcaatctgct atcatgagtt tacaacatct gctcgtatta caccgtgtaa tcattatttc     120
catgcacttt gccttcggaa atggctgtac attcaagata cttgtccaat gtgccatcag     180
aaagtataca tcgaagatga tatcaaggat aattca                                216
```

<210> SEQ ID NO 42
<211> LENGTH: 242

```
<212> TYPE: PRT
<213> ORGANISM: Artificial Sequence
<220> FEATURE:
<223> OTHER INFORMATION: fusion protein including the RNF139(trc8) E3
      RING motif, Ubc7 UCE E2 protein and peptide linker

<400> SEQUENCE: 42
```

Met Ile Asn Ser Leu Pro Glu Ile Lys Gly Ser Arg Leu Gln Glu Ile
1               5                   10                  15

Asn Asp Val Cys Ala Ile Cys Tyr His Glu Phe Thr Thr Ser Ala Arg
            20                  25                  30

Ile Thr Pro Cys Asn His Tyr Phe His Ala Leu Cys Leu Arg Lys Trp
        35                  40                  45

Leu Tyr Ile Gln Asp Thr Cys Pro Met Cys His Gln Lys Val Tyr Ile
    50                  55                  60

Glu Asp Asp Ile Lys Asp Asn Ser Gly Thr Gly Ser His Met Ala Gly
65                  70                  75                  80

Thr Ala Leu Lys Arg Leu Met Ala Glu Tyr Lys Gln Leu Thr Leu Asn
                85                  90                  95

Pro Pro Glu Gly Ile Val Ala Gly Pro Met Asn Glu Glu Asn Phe Phe
            100                 105                 110

Glu Trp Glu Ala Leu Ile Met Gly Pro Glu Asp Thr Cys Phe Glu Phe
        115                 120                 125

Gly Val Phe Pro Ala Ile Leu Ser Phe Pro Leu Asp Tyr Pro Leu Ser
    130                 135                 140

Pro Pro Lys Met Arg Phe Thr Cys Glu Met Phe His Pro Asn Ile Tyr
145                 150                 155                 160

Pro Asp Gly Arg Val Cys Ile Ser Ile Leu His Ala Pro Gly Asp Asp
                165                 170                 175

Pro Met Gly Tyr Glu Ser Ser Ala Glu Arg Trp Ser Pro Val Gln Ser
            180                 185                 190

Val Glu Lys Ile Leu Leu Ser Val Val Ser Met Leu Ala Glu Pro Asn
        195                 200                 205

Asp Glu Ser Gly Ala Asn Val Asp Ala Ser Lys Met Trp Arg Asp Asp
    210                 215                 220

Arg Glu Gln Phe Tyr Lys Ile Ala Lys Gln Ile Val Gln Lys Ser Leu
225                 230                 235                 240

Gly Leu

```
<210> SEQ ID NO 43
<211> LENGTH: 729
<212> TYPE: DNA
<213> ORGANISM: Artificial Sequence
<220> FEATURE:
<223> OTHER INFORMATION: cDNA sequence encoding a fusion protein
      including the E3 RING motif of RNF139(trc8), Ubc7 UCE E2 protein
      and peptide linker

<400> SEQUENCE: 43
atgattaatt cacttcctga aataaaaggg agccgcttac aagaaataaa tgatgtatgt    60
gcaatctgct atcatgagtt tacaacatct gctcgtatta caccgtgtaa tcattatttc   120
catgcacttt gccttcggaa atggctgtac attcaagata cttgtccaat gtgccatcag   180
aaagtataca tcgaagatga tatcaaggat aattcaggta ccggatccca tatggcgggg   240
accgcgctca agaggctgat ggccgagtac aaacaattaa cactgaatcc tccggaagga   300
attgtagcag gccccatgaa tgaagagaac ttttttgaat gggaggcatt gatcatgggc   360
ccagaagaca cctgctttga gtttggtgtt tttcctgcca tcctgagttt cccacttgat   420
```

```
tacccgttaa gtcccccaaa gatgagattt acctgtgaga tgtttcatcc caacatctac    480
cctgatggga gagtctgcat ttccatcctc cacgcgccag gcgatgaccc catgggctac    540
gagagcagcg cggagcggtg gagtcctgtg cagagtgtgg agaagatcct gctgtcggtg    600
gtgagcatgc tggcagagcc caatgacgaa agtggagcta acgtggatgc gtccaaaatg    660
tggcgcgatg accgggagca gttctataag attgccaagc agatcgtcca gaagtctctg    720
ggactgtga                                                            729
```

```
<210> SEQ ID NO 44
<211> LENGTH: 43
<212> TYPE: PRT
<213> ORGANISM: Homo sapiens

<400> SEQUENCE: 44
```

Cys Ala Ile Cys Leu Asp Glu Tyr Glu Glu Gly Asp Gln Leu Lys Ile
1               5                   10                  15

Leu Pro Cys Ser His Thr Tyr His Cys Lys Cys Ile Asp Pro Trp Phe
            20                  25                  30

Ser Gln Ala Pro Arg Arg Ser Cys Pro Val Cys
        35                  40

```
<210> SEQ ID NO 45
<211> LENGTH: 129
<212> TYPE: DNA
<213> ORGANISM: Homo sapiens

<400> SEQUENCE: 45
tgtgccatct gcctggatga gtacgaggag ggcgaccaac tcaagatcct gccctgctcc    60
cacacctacc actgcaaatg cattgacccc tggttctccc aagcccccg gcgctcctgc    120 cccgtgtgc                                                            129
```

```
<210> SEQ ID NO 46
<211> LENGTH: 75
<212> TYPE: PRT
<213> ORGANISM: Homo sapiens

<400> SEQUENCE: 46
```

Met Thr Ser Thr Cys Gln Lys Ala Gln Val Arg Thr Phe Thr Trp His
1               5                   10                  15

Asn Asp Leu Cys Ala Ile Cys Leu Asp Glu Tyr Glu Glu Gly Asp Gln
            20                  25                  30

Leu Lys Ile Leu Pro Cys Ser His Thr Tyr His Cys Lys Cys Ile Asp
        35                  40                  45

Pro Trp Phe Ser Gln Ala Pro Arg Arg Ser Cys Pro Val Cys Lys Gln
    50                  55                  60

Ser Val Ala Ala Thr Glu Asp Ser Phe Asp Ser
65                  70                  75

```
<210> SEQ ID NO 47
<211> LENGTH: 225
<212> TYPE: DNA
<213> ORGANISM: Homo sapiens

<400> SEQUENCE: 47
atgacgtcta cctgccagaa ggcccaggtc cgcaccttca cgtggcacaa cgacctgtgt    60
gccatctgcc tggatgagta cgaggagggc gaccaactca agatcctgcc ctgctcccac    120
acctaccact gcaaatgcat tgacccctgg ttctcccaag ccccccggcg ctcctgcccc    180
```
gtgtgcaaac agtcggtggc cgccacagaa gacagctttg actcc 225

<210> SEQ ID NO 48
<211> LENGTH: 245
<212> TYPE: PRT
<213> ORGANISM: Artificial Sequence
<220> FEATURE:
<223> OTHER INFORMATION: fusion protein including the RNFx2 E3 RING
      motif, Ubc7 UCE E2 protein and peptide linker

<400> SEQUENCE: 48

```
Met Thr Ser Thr Cys Gln Lys Ala Gln Val Arg Thr Phe Thr Trp His
1               5                   10                  15

Asn Asp Leu Cys Ala Ile Cys Leu Asp Glu Tyr Glu Gly Asp Gln
            20                  25                  30

Leu Lys Ile Leu Pro Cys Ser His Thr Tyr His Cys Lys Cys Ile Asp
        35                  40                  45

Pro Trp Phe Ser Gln Ala Pro Arg Arg Ser Cys Pro Val Cys Lys Gln
    50                  55                  60

Ser Val Ala Ala Thr Glu Asp Ser Phe Asp Ser Gly Thr Gly Ser His
65                  70                  75                  80

Met Ala Gly Thr Ala Leu Lys Arg Leu Met Ala Glu Tyr Lys Gln Leu
                85                  90                  95

Thr Leu Asn Pro Pro Glu Gly Ile Val Ala Gly Pro Met Asn Glu Glu
            100                 105                 110

Asn Phe Phe Glu Trp Glu Ala Leu Ile Met Gly Pro Glu Asp Thr Cys
        115                 120                 125

Phe Glu Phe Gly Val Phe Pro Ala Ile Leu Ser Phe Pro Leu Asp Tyr
    130                 135                 140

Pro Leu Ser Pro Pro Lys Met Arg Phe Thr Cys Glu Met Phe His Pro
145                 150                 155                 160

Asn Ile Tyr Pro Asp Gly Arg Val Cys Ile Ser Ile Leu His Ala Pro
                165                 170                 175

Gly Asp Asp Pro Met Gly Tyr Glu Ser Ser Ala Glu Arg Trp Ser Pro
            180                 185                 190

Val Gln Ser Val Glu Lys Ile Leu Leu Ser Val Val Ser Met Leu Ala
        195                 200                 205

Glu Pro Asn Asp Glu Ser Gly Ala Asn Val Asp Ala Ser Lys Met Trp
    210                 215                 220

Arg Asp Asp Arg Glu Gln Phe Tyr Lys Ile Ala Lys Gln Ile Val Gln
225                 230                 235                 240

Lys Ser Leu Gly Leu
                245
```

<210> SEQ ID NO 49
<211> LENGTH: 738
<212> TYPE: DNA
<213> ORGANISM: Artificial Sequence
<220> FEATURE:
<223> OTHER INFORMATION: cDNA sequence encoding a fusion protein
      including the E3 RING motif of RNFx2, Ubc7 UCE E2 protein and
      peptide linker

<400> SEQUENCE: 49
atgacgtcta cctgccagaa ggcccaggtc cgcaccttca cgtggcacaa cgacctgtgt   60
gccatctgcc tggatgagta cgaggagggc gaccaactca agatcctgcc ctgctcccac  120
acctaccact gcaaatgcat tgaccctggg ttctcccaag ccccccggcg ctcctgcccc  180

```
gtgtgcaaac agtcggtggc cgccacagaa gacagctttg actccggtac cggatcccat    240
atggcgggga ccgcgctcaa gaggctgatg gccgagtaca aacaattaac actgaatcct    300
ccggaaggaa ttgtagcagg ccccatgaat gaagagaact tttttgaatg ggaggcattg    360
atcatgggcc cagaagacac ctgctttgag tttggtgttt ttcctgccat cctgagtttc    420
ccacttgatt acccgttaag tcccccaaag atgagattta cctgtgagat gtttcatccc    480
aacatctacc ctgatgggag agtctgcatt tccatcctcc acgcgccagg cgatgacccc    540
atgggctacg agagcagcgc ggagcggtgg agtcctgtgc agagtgtgga agatcctg     600 ctgtcggtgg tgagcatgct ggcagagccc aatgacgaaa gtggagctaa cgtggatgcg    660
tccaaaatgt ggcgcgatga ccgggagcag ttctataaga ttgccaagca gatcgtccag    720
aagtctctgg gactgtga                                                  738
```

<210> SEQ ID NO 50
<211> LENGTH: 41
<212> TYPE: PRT
<213> ORGANISM: Homo sapiens

<400> SEQUENCE: 50

Cys Pro Val Cys Lys Asp Asp Tyr Ala Leu Gly Glu Arg Val Arg Gln
1               5                   10                  15

Leu Pro Cys Asn His Leu Phe His Asp Gly Cys Ile Val Pro Trp Leu
            20                  25                  30

Glu Gln His Asp Ser Cys Pro Val Cys
        35                  40

<210> SEQ ID NO 51
<211> LENGTH: 123
<212> TYPE: DNA
<213> ORGANISM: Homo sapiens

<400> SEQUENCE: 51

```
tgccctgtgt gcaaggacga ctacgcgctg ggtgagcgtg tgcggcagct gccctgcaac     60
cacctgttcc acgacggctg catcgtgccc tggctggagc agcacgacag ctgccccgtc    120
tgc                                                                   123
```

<210> SEQ ID NO 52
<211> LENGTH: 72
<212> TYPE: PRT
<213> ORGANISM: Homo sapiens

<400> SEQUENCE: 52

Met Gln Ala Leu Pro Thr Val Pro Val Thr Glu Glu His Val Gly Ser
1               5                   10                  15

Gly Leu Glu Cys Pro Val Cys Lys Asp Asp Tyr Ala Leu Gly Glu Arg
            20                  25                  30

Val Arg Gln Leu Pro Cys Asn His Leu Phe His Asp Gly Cys Ile Val
        35                  40                  45

Pro Trp Leu Glu Gln His Asp Ser Cys Pro Val Cys Arg Lys Ser Leu
    50                  55                  60

Thr Gly Gln Asn Thr Ala Thr Asn
65                  70

<210> SEQ ID NO 53
<211> LENGTH: 216
<212> TYPE: DNA
<213> ORGANISM: Homo sapiens -continued

```
<400> SEQUENCE: 53
atgcaggccc tccccaccgt ccccgtcact gaggagcacg taggctccgg gctcgagtgc    60
cctgtgtgca aggacgacta cgcgctgggt gagcgtgtgc ggcagctgcc ctgcaaccac   120
ctgttccacg acggctgcat cgtgccctgg ctggagcagc acgacagctg ccccgtctgc   180
cgaaaaagcc tcacgggaca gaacacggcc acgaac                             216
```

```
<210> SEQ ID NO 54
<211> LENGTH: 242
<212> TYPE: PRT
<213> ORGANISM: Artificial Sequence
<220> FEATURE:
<223> OTHER INFORMATION: fusion protein including the RNF126 RING motif,
      Ubc7 UCE E2 protein and peptide linker

<400> SEQUENCE: 54
```

```
Met Gln Ala Leu Pro Thr Val Pro Val Thr Glu Glu His Val Gly Ser
1               5                  10                  15

Gly Leu Glu Cys Pro Val Cys Lys Asp Asp Tyr Ala Leu Gly Glu Arg
            20                  25                  30

Val Arg Gln Leu Pro Cys Asn His Leu Phe His Asp Gly Cys Ile Val
        35                  40                  45

Pro Trp Leu Glu Gln His Asp Ser Cys Pro Val Cys Arg Lys Ser Leu
    50                  55                  60

Thr Gly Gln Asn Thr Ala Thr Asn Gly Thr Gly Ser His Met Ala Gly
65                  70                  75                  80

Thr Ala Leu Lys Arg Leu Met Ala Glu Tyr Lys Gln Leu Thr Leu Asn
                85                  90                  95

Pro Pro Glu Gly Ile Val Ala Gly Pro Met Asn Glu Glu Asn Phe Phe
            100                 105                 110

Glu Trp Glu Ala Leu Ile Met Gly Pro Glu Asp Thr Cys Phe Glu Phe
        115                 120                 125

Gly Val Phe Pro Ala Ile Leu Ser Phe Pro Leu Asp Tyr Pro Leu Ser
    130                 135                 140

Pro Pro Lys Met Arg Phe Thr Cys Glu Met Phe His Pro Asn Ile Tyr
145                 150                 155                 160

Pro Asp Gly Arg Val Cys Ile Ser Ile Leu His Ala Pro Gly Asp Asp
                165                 170                 175

Pro Met Gly Tyr Glu Ser Ser Ala Glu Arg Trp Ser Pro Val Gln Ser
            180                 185                 190

Val Glu Lys Ile Leu Leu Ser Val Ser Met Leu Ala Glu Pro Asn
        195                 200                 205

Asp Glu Ser Gly Ala Asn Val Asp Ala Ser Lys Met Trp Arg Asp Asp
    210                 215                 220

Arg Glu Gln Phe Tyr Lys Ile Ala Lys Gln Ile Val Gln Lys Ser Leu
225                 230                 235                 240

Gly Leu
```

```
<210> SEQ ID NO 55
<211> LENGTH: 729
<212> TYPE: DNA
<213> ORGANISM: Artificial Sequence
<220> FEATURE:
<223> OTHER INFORMATION: cDNA sequence encoding a fusion protein
      including the E3 RING motif of RNF126, Ubc7 UCE E2 protein and
      peptide linker

<400> SEQUENCE: 55
```

-continued

```
atgcaggccc tccccaccgt ccccgtcact gaggagcacg taggctccgg gctcgagtgc    60
cctgtgtgca aggacgacta cgcgctgggt gagcgtgtgc ggcagctgcc ctgcaaccac   120
ctgttccacg acggctgcat cgtgccctgg ctggagcagc acgacagctg cccgtctgc   180 cgaaaaagcc tcacgggaca gaacacggcc acgaacggta ccggatccca tatggcgggg   240
accgcgctca agaggctgat ggccgagtac aaacaattaa cactgaatcc tccggaagga   300
attgtagcag gccccatgaa tgaagagaac ttttttgaat gggaggcatt gatcatgggc   360
ccagaagaca cctgctttga gtttggtgtt tttcctgcca tcctgagttt cccacttgat   420
tacccgttaa gtccccccaaa gatgagattt acctgtgaga tgtttcatcc aacatctac   480 cctgatggga gagtctgcat ttccatcctc cacgcgccag gcgatgaccc catgggctac   540
gagagcagcg cggagcggtg gagtcctgtg cagagtgtgg agaagatcct gctgtcggtg   600
gtgagcatgc tggcagagcc caatgacgaa agtggagcta acgtggatgc gtccaaaatg   660
tggcgcgatg accgggagca gttctataag attgccaagc agatcgtcca gaagtctctg   720
ggactgtga                                                            729
```

<210> SEQ ID NO 56
<211> LENGTH: 39
<212> TYPE: PRT
<213> ORGANISM: Homo sapiens

<400> SEQUENCE: 56

Cys Ile Ile Cys Arg Glu Glu Met Val Thr Gly Ala Lys Arg Leu Pro
1               5                   10                  15

Cys Asn His Ile Phe His Thr Ser Cys Leu Arg Ser Trp Phe Gln Arg
            20                  25                  30

Gln Gln Thr Cys Pro Thr Cys
        35

<210> SEQ ID NO 57
<211> LENGTH: 117
<212> TYPE: DNA
<213> ORGANISM: Homo sapiens

<400> SEQUENCE: 57

```
tgcatcatct gccgagaaga gatggtgact ggtgccaaga gactgccctg caaccacatt    60
ttccatacca gctgcctgcg ctcctggttc cagcggcagc agacctgccc cacctgc     117
```

<210> SEQ ID NO 58
<211> LENGTH: 72
<212> TYPE: PRT
<213> ORGANISM: Homo sapiens

<400> SEQUENCE: 58

Met Asn Thr Leu Tyr Pro Asp Ala Thr Pro Glu Glu Leu Gln Ala Met
1               5                   10                  15

Asp Asn Val Cys Ile Ile Cys Arg Glu Glu Met Val Thr Gly Ala Lys
            20                  25                  30

Arg Leu Pro Cys Asn His Ile Phe His Thr Ser Cys Leu Arg Ser Trp
        35                  40                  45

Phe Gln Arg Gln Gln Thr Cys Pro Thr Cys Arg Met Asp Val Leu Arg
    50                  55                  60

Ala Ser Leu Pro Ala Gln Ser Pro
65                  70

<210> SEQ ID NO 59

```
<211> LENGTH: 216
<212> TYPE: DNA
<213> ORGANISM: Homo sapiens

<400> SEQUENCE: 59
atgaacaccc tgtatccaga tgccacccca gaggagctcc aggcaatgga caatgtctgc      60
atcatctgcc gagaagagat ggtgactggt gccaagagac tgccctgcaa ccacattttc     120
cataccagct gcctgcgctc ctggttccag cggcagcaga cctgccccac ctgccgtatg     180
gatgtccttc gtgcatcgct gccagcgcag tcacca                               216

<210> SEQ ID NO 60
<211> LENGTH: 242
<212> TYPE: PRT
<213> ORGANISM: Artificial Sequence
<220> FEATURE:
<223> OTHER INFORMATION: fusion protein including the Hrd1 RING motif,
      Ubc7 UCE E2 protein and peptide linker

<400> SEQUENCE: 60
```

Met Asn Thr Leu Tyr Pro Asp Ala Thr Pro Glu Glu Leu Gln Ala Met
1               5                   10                  15

Asp Asn Val Cys Ile Ile Cys Arg Glu Met Val Thr Gly Ala Lys
            20                  25                  30

Arg Leu Pro Cys Asn His Ile Phe His Thr Ser Cys Leu Arg Ser Trp
        35                  40                  45

Phe Gln Arg Gln Gln Thr Cys Pro Thr Cys Arg Met Asp Val Leu Arg
    50                  55                  60

Ala Ser Leu Pro Ala Gln Ser Pro Gly Thr Gly Ser His Met Ala Gly
65                  70                  75                  80

Thr Ala Leu Lys Arg Leu Met Ala Glu Tyr Lys Gln Leu Thr Leu Asn
                85                  90                  95

Pro Pro Glu Gly Ile Val Ala Gly Pro Met Asn Glu Glu Asn Phe Phe
            100                 105                 110

Glu Trp Glu Ala Leu Ile Met Gly Pro Glu Asp Thr Cys Phe Glu Phe
        115                 120                 125

Gly Val Phe Pro Ala Ile Leu Ser Phe Pro Leu Asp Tyr Pro Leu Ser
    130                 135                 140

Pro Pro Lys Met Arg Phe Thr Cys Glu Met Phe His Pro Asn Ile Tyr
145                 150                 155                 160

Pro Asp Gly Arg Val Cys Ile Ser Ile Leu His Ala Pro Gly Asp Asp
                165                 170                 175

Pro Met Gly Tyr Glu Ser Ser Ala Glu Arg Trp Ser Pro Val Gln Ser
            180                 185                 190

Val Glu Lys Ile Leu Leu Ser Val Val Ser Met Leu Ala Glu Pro Asn
        195                 200                 205

Asp Glu Ser Gly Ala Asn Val Asp Ala Ser Lys Met Trp Arg Asp Asp
    210                 215                 220

Arg Glu Gln Phe Tyr Lys Ile Ala Lys Gln Ile Val Gln Lys Ser Leu
225                 230                 235                 240

Gly Leu

```
<210> SEQ ID NO 61
<211> LENGTH: 729
<212> TYPE: DNA
<213> ORGANISM: Artificial Sequence
<220> FEATURE:
<223> OTHER INFORMATION: cDNA sequence encoding a fusion protein
      including the E3 RING motif of Hrd1, Ubc7 UCE E2 protein and
``` peptide linker

<400> SEQUENCE: 61

```
atgaacaccc tgtatccaga tgccacccca gaggagctcc aggcaatgga caatgtctgc      60
atcatctgcc gagaagagat ggtgactggt gccaagagac tgccctgcaa ccacattttc     120
cataccagct gcctgcgctc ctggttccag cggcagcaga cctgccccac ctgccgtatg     180
gatgtccttc gtgcatcgct gccagcgcag tcaccaggta ccggatccca tatggcgggg     240
accgcgctca gaggctgatg gccgagtaca aacaattaa cactgaatcc tccggaagga      300
attgtagcag gccccatgaa tgaagagaac ttttttgaat gggaggcatt gatcatgggc     360
ccagaagaca cctgctttga gtttggtgtt tttcctgcca tcctgagttt cccacttgat     420
tacccgttaa gtcccccaaa gatgagattt acctgtgaga tgtttcatcc aacatctac      480
cctgatggga gagtctgcat tccatcctc cacgcgccag gcgatgaccc catgggctac      540
gagagcagcg cggagcggtg gagtcctgtg cagagtgtgg agaagatcct gctgtcggtg     600
gtgagcatgc tggcagagcc caatgacgaa agtggagcta acgtggatgc gtccaaaatg     660
tggcgcgatg accgggagca gttctataag attgccaagc agatcgtcca gaagtctctg     720
ggactgtga                                                              729
```

<210> SEQ ID NO 62
<211> LENGTH: 47
<212> TYPE: PRT
<213> ORGANISM: Homo sapiens

<400> SEQUENCE: 62

Cys Arg Ile Cys His Cys Glu Gly Asp Glu Glu Ser Pro Leu Ile Thr
1               5                   10                  15

Pro Cys Arg Cys Thr Gly Thr Leu Arg Phe Val His Gln Ser Cys Leu
                20                  25                  30

His Gln Trp Ile Lys Ser Ser Asp Thr Arg Cys Cys Glu Leu Cys
        35                  40                  45

<210> SEQ ID NO 63
<211> LENGTH: 141
<212> TYPE: DNA
<213> ORGANISM: Homo sapiens

<400> SEQUENCE: 63

```
tgcagaatct gtcactgcga aggggatgaa gagagccccc tcatcacacc ctgtcgctgc      60
actgggacac tgcgctttgt ccaccagtcc tgcctccacc agtggataaa gagctcagat     120
acacgctgct gtgagctctg c                                                141
```

<210> SEQ ID NO 64
<211> LENGTH: 76
<212> TYPE: PRT
<213> ORGANISM: Homo sapiens

<400> SEQUENCE: 64

Met Ala Pro Arg Ser Gln Ser Arg Leu Ser Val Cys Pro Ser Thr Gln
1               5                   10                  15

Asp Ile Cys Arg Ile Cys His Cys Glu Gly Asp Glu Glu Ser Pro Leu
                20                  25                  30

Ile Thr Pro Cys Arg Cys Thr Gly Thr Leu Arg Phe Val His Gln Ser
        35                  40                  45

Cys Leu His Gln Trp Ile Lys Ser Ser Asp Thr Arg Cys Cys Glu Leu
    50                  55                  60

Cys Lys Tyr Asp Phe Ile Met Glu Thr Lys Leu Lys
 65                  70                  75

<210> SEQ ID NO 65
<211> LENGTH: 228
<212> TYPE: DNA
<213> ORGANISM: Homo sapiens

<400> SEQUENCE: 65
atggctccca ggagccagtc aaggttgtct gtctgtccat ccactcagga catctgcaga      60
atctgtcact gcaaggggga tgaagagagc cccctcatca cccctgtcg ctgcactggg     120 acactgcgct ttgtccacca gtcctgcctc caccagtgga taaagagctc agatacacgc    180
tgctgtgagc tctgcaagta tgacttcata atggagacca agctcaaa               228

<210> SEQ ID NO 66
<211> LENGTH: 246
<212> TYPE: PRT
<213> ORGANISM: Artificial Sequence
<220> FEATURE:
<223> OTHER INFORMATION: fusion protein including the MARCH1 RING motif,
      Ubc7 UCE E2 protein and peptide linker

<400> SEQUENCE: 66

Met Ala Pro Arg Ser Gln Ser Arg Leu Ser Val Cys Pro Ser Thr Gln
  1               5                  10                  15

Asp Ile Cys Arg Ile Cys His Cys Glu Gly Asp Glu Glu Ser Pro Leu
                 20                  25                  30

Ile Thr Pro Cys Arg Cys Thr Gly Thr Leu Arg Phe Val His Gln Ser
             35                  40                  45

Cys Leu His Gln Trp Ile Lys Ser Ser Asp Thr Arg Cys Cys Glu Leu
 50                  55                  60

Cys Lys Tyr Asp Phe Ile Met Glu Thr Lys Leu Lys Gly Thr Gly Ser
 65                  70                  75                  80

His Met Ala Gly Thr Ala Leu Lys Arg Leu Met Ala Glu Tyr Lys Gln
                 85                  90                  95

Leu Thr Leu Asn Pro Pro Glu Gly Ile Val Ala Gly Pro Met Asn Glu
                100                 105                 110

Glu Asn Phe Phe Glu Trp Glu Ala Leu Ile Met Gly Pro Glu Asp Thr
            115                 120                 125

Cys Phe Glu Phe Gly Val Phe Pro Ala Ile Leu Ser Phe Pro Leu Asp
130                 135                 140

Tyr Pro Leu Ser Pro Pro Lys Met Arg Phe Thr Cys Glu Met Phe His
145                 150                 155                 160

Pro Asn Ile Tyr Pro Asp Gly Arg Val Cys Ile Ser Ile Leu His Ala
                165                 170                 175

Pro Gly Asp Asp Pro Met Gly Tyr Glu Ser Ser Ala Glu Arg Trp Ser
            180                 185                 190

Pro Val Gln Ser Val Glu Lys Ile Leu Leu Ser Val Val Ser Met Leu
        195                 200                 205

Ala Glu Pro Asn Asp Glu Ser Gly Ala Asn Val Asp Ala Ser Lys Met
210                 215                 220

Trp Arg Asp Asp Arg Glu Gln Phe Tyr Lys Ile Ala Lys Gln Ile Val
225                 230                 235                 240

Gln Lys Ser Leu Gly Leu
                245

<210> SEQ ID NO 67
<211> LENGTH: 741
<212> TYPE: DNA
<213> ORGANISM: Artificial Sequence
<220> FEATURE:
<223> OTHER INFORMATION: cDNA sequence encoding a fusion protein including the E3 RING motif of MARCH1, Ubc7 UCE E2 protein and peptide linker

<400> SEQUENCE: 67

```
atggctccca ggagccagtc aaggttgtct gtctgtccat ccactcagga catctgcaga      60
atctgtcact gcgaagggga tgaagagagc cccctcatca caccctgtcg ctgcactggg     120
acactgcgct ttgtccacca gtcctgcctc caccagtgga taaagagctc agatacacgc     180
tgctgtgagc tctgcaagta tgacttcata tggagaccaa gctcaaagg taccggatcc     240
catatggcgg ggaccgcgct caagaggctg atggccgagt acaaacaatt aacactgaat     300
cctccggaag gaattgtagc aggccccatg aatgaagaga cttttttga atgggaggca     360
ttgatcatgg gcccagaaga cacctgcttt gagtttggtg ttttccctgc atcctgagt     420
ttcccacttg attacccgtt aagtccccca aagatgagat ttacctgtga gatgtttcat     480
cccaacatct accctgatgg gagagtctgc atttccatcc tccacgcgcc aggcgatgac     540
cccatgggct acgagagcag cgcggagcgg tggagtcctg tgcagagtgt ggagaagatc     600
ctgctgtcgg tggtgagcat gctggcagag cccaatgacg aaagtggagc taacgtggat     660
gcgtccaaaa tgtggcgcga tgaccgggag cagttctata agattgccaa gcagatcgtc     720
cagaagtctc tgggactgtg a                                              741
```

<210> SEQ ID NO 68
<211> LENGTH: 1058
<212> TYPE: PRT
<213> ORGANISM: Homo sapiens

<400> SEQUENCE: 68

```
Met Ser Ser Ser Pro Leu Ser Lys Lys Arg Val Ser Gly Pro Asp
1               5                   10                  15

Pro Lys Pro Gly Ser Asn Cys Ser Pro Ala Gln Ser Val Leu Ser Glu
            20                  25                  30

Val Pro Ser Val Pro Thr Asn Gly Met Ala Lys Asn Gly Ser Glu Ala
        35                  40                  45

Asp Ile Asp Glu Gly Leu Tyr Ser Arg Gln Leu Tyr Val Leu Gly His
    50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
            100                 105                 110

Ser Ser Gln Phe Tyr Leu Arg Glu Glu Asp Ile Gly Lys Asn Arg Ala
        115                 120                 125

Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Thr Pro Leu Glu Asp Gln Leu Arg Val Gly
                165                 170                 175

Glu Phe Cys His Asn Arg Gly Ile Lys Leu Val Val Ala Asp Thr Arg
            180                 185                 190
```

```
Gly Leu Phe Gly Gln Leu Phe Cys Asp Phe Gly Glu Glu Met Ile Leu
            195                 200                 205

Thr Asp Ser Asn Gly Glu Gln Pro Leu Ser Ala Met Val Ser Met Val
            210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
            245                 250                 255

Val Glu Leu Asn Gly Asn Gln Pro Met Glu Ile Lys Val Leu Gly Pro
            260                 265                 270

Tyr Thr Phe Ser Ile Cys Asp Thr Ser Asn Phe Ser Asp Tyr Ile Arg
            275                 280                 285

Gly Gly Ile Val Ser Gln Val Lys Val Pro Lys Lys Ile Ser Phe Lys
            290                 295                 300

Ser Leu Val Ala Ser Leu Ala Glu Pro Asp Phe Val Val Thr Asp Phe
305                 310                 315                 320

Ala Lys Phe Ser Arg Pro Ala Gln Leu His Ile Gly Phe Gln Ala Leu
            325                 330                 335

His Gln Phe Cys Ala Gln His Gly Arg Pro Pro Arg Pro Arg Asn Glu
            340                 345                 350

Glu Asp Ala Ala Glu Leu Val Ala Leu Ala Gln Ala Val Asn Ala Arg
            355                 360                 365

Ala Leu Pro Ala Val Gln Gln Asn Asn Leu Asp Glu Asp Leu Ile Arg
            370                 375                 380

Lys Leu Ala Tyr Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
            405                 410                 415

Phe Met Pro Ile Met Gln Trp Leu Tyr Phe Asp Ala Leu Glu Cys Leu
            420                 425                 430

Pro Glu Asp Lys Glu Val Leu Thr Glu Asp Lys Cys Leu Gln Arg Gln
            435                 440                 445

Asn Arg Tyr Asp Gly Gln Val Ala Val Phe Gly Ser Asp Leu Gln Glu
            450                 455                 460

Lys Leu Gly Lys Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
            485                 490                 495

Gly Gly Glu Ile Ile Val Thr Asp Met Asp Thr Ile Glu Lys Ser Asn
            500                 505                 510

Leu Asn Arg Gln Phe Leu Phe Arg Pro Trp Asp Val Thr Lys Leu Lys
            515                 520                 525

Ser Asp Thr Ala Ala Ala Val Arg Gln Met Asn Pro His Ile Arg
            530                 535                 540

Val Thr Ser His Gln Asn Arg Val Gly Pro Asp Thr Glu Arg Ile Tyr
545                 550                 555                 560

Asp Asp Asp Phe Phe Gln Asn Leu Asp Gly Val Ala Asn Ala Leu Asp
            565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
            595                 600                 605

Val Val Ile Pro Phe Leu Thr Glu Ser Tyr Ser Ser Ser Gln Asp Pro
```

```
              610                 615                 620
Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                    645                 650                 655

Lys Gln Pro Ala Glu Asn Val Asn Gln Tyr Leu Thr Asp Pro Lys Phe
                660                 665                 670

Val Glu Arg Thr Leu Arg Leu Ala Gly Thr Gln Pro Leu Glu Val Leu
                675                 680                 685

Glu Ala Val Gln Arg Ser Leu Val Leu Gln Arg Pro Gln Thr Trp Ala
690                 695                 700

Asp Cys Val Thr Trp Ala Cys His His Trp His Thr Gln Tyr Ser Asn
705                 710                 715                 720

Asn Ile Arg Gln Leu Leu His Asn Phe Pro Pro Asp Gln Leu Thr Ser
                    725                 730                 735

Ser Gly Ala Pro Phe Trp Ser Gly Pro Lys Arg Cys Pro His Pro Leu
                740                 745                 750

Thr Phe Asp Val Asn Asn Pro Leu His Leu Asp Tyr Val Met Ala Ala
                755                 760                 765

Ala Asn Leu Phe Ala Gln Thr Tyr Gly Leu Thr Gly Ser Gln Asp Arg
770                 775                 780

Ala Ala Val Ala Thr Phe Leu Gln Ser Val Gln Val Pro Glu Phe Thr
785                 790                 795                 800

Pro Lys Ser Gly Val Lys Ile His Val Ser Asp Gln Glu Leu Gln Ser
                    805                 810                 815

Ala Asn Ala Ser Val Asp Asp Ser Arg Leu Glu Glu Leu Lys Ala Thr
                820                 825                 830

Leu Pro Ser Pro Asp Lys Leu Pro Gly Phe Lys Met Tyr Pro Ile Asp
                835                 840                 845

Phe Glu Lys Asp Asp Asp Ser Asn Phe His Met Asp Phe Ile Val Ala
                850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Pro Ala Ile Ala Thr
                    885                 890                 895

Thr Thr Ala Ala Val Val Gly Leu Val Cys Leu Glu Leu Tyr Lys Val
                900                 905                 910

Val Gln Gly His Arg Gln Leu Asp Ser Tyr Lys Asn Gly Phe Leu Asn
                915                 920                 925

Leu Ala Leu Pro Phe Phe Gly Phe Ser Glu Pro Leu Ala Ala Pro Arg
930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
                980                 985                 990

Gly Val Ser Met Leu Tyr Ser Phe Phe Met Pro Ala Ala Lys Leu Lys
                995                 1000                1005

Glu Arg Leu Asp Gln Pro Met Thr Glu Ile Val Ser Arg Val Ser
    1010                1015                1020

Lys Arg Lys Leu Gly Arg His Val Arg Ala Leu Val Leu Glu Leu
    1025                1030                1035
```

Cys Cys Asn Asp Glu Ser Gly Glu Asp Val Glu Val Pro Tyr Val
            1040                1045                1050

Arg Tyr Thr Ile Arg
    1055

<210> SEQ ID NO 69
<211> LENGTH: 238
<212> TYPE: PRT
<213> ORGANISM: Homo sapiens

<400> SEQUENCE: 69

Met Ala Gln Gln Gln Met Thr Ser Ser Gln Lys Ala Leu Met Leu Glu
1               5                   10                  15

Leu Lys Ser Leu Gln Glu Glu Pro Val Glu Gly Phe Arg Ile Thr Leu
            20                  25                  30

Val Asp Glu Ser Asp Leu Tyr Asn Trp Glu Val Ala Ile Phe Gly Pro
        35                  40                  45

Pro Asn Thr Leu Tyr Glu Gly Gly Tyr Phe Lys Ala His Ile Lys Phe
    50                  55                  60

Pro Ile Asp Tyr Pro Tyr Ser Pro Pro Thr Phe Arg Phe Leu Thr Lys
65                  70                  75                  80

Met Trp His Pro Asn Ile Tyr Glu Asn Gly Asp Val Cys Ile Ser Ile
                85                  90                  95

Leu His Pro Pro Val Asp Asp Pro Gln Ser Gly Glu Leu Pro Ser Glu
            100                 105                 110

Arg Trp Asn Pro Thr Gln Asn Val Arg Thr Ile Leu Leu Ser Val Ile
        115                 120                 125

Ser Leu Leu Asn Glu Pro Asn Thr Phe Ser Pro Ala Asn Val Asp Ala
    130                 135                 140

Ser Val Met Phe Arg Lys Trp Arg Asp Ser Lys Gly Lys Asp Lys Glu
145                 150                 155                 160

Tyr Ala Glu Ile Ile Arg Lys Gln Val Ser Ala Thr Lys Ala Glu Ala
                165                 170                 175

Glu Lys Asp Gly Val Lys Val Pro Thr Thr Leu Ala Glu Tyr Cys Ile
            180                 185                 190

Lys Thr Lys Val Pro Ser Asn Asp Asn Ser Ser Asp Leu Leu Tyr Asp
        195                 200                 205

Asp Leu Tyr Asp Asp Asp Ile Asp Asp Glu Asp Glu Glu Glu Glu Asp
    210                 215                 220

Ala Asp Cys Tyr Asp Asp Asp Ser Gly Asn Glu Glu Ser
225                 230                 235

<210> SEQ ID NO 70
<211> LENGTH: 717
<212> TYPE: DNA
<213> ORGANISM: Homo sapiens

<400> SEQUENCE: 70
atggcccagc agcagatgac cagctcgcag aaggccctga tgctcgagct gaaatccctg      60
caggaggaac cggtggaggg cttccggatc accctggtgg acgagtccga cctctacaac     120
tgggaggtgg ccatcttcgg acccccaac acccctctacg aaggcggcta cttcaaggcg     180
catattaaat ttcctattga ctaccccctat tcaccaccta ccttcagatt cttgaccaaa     240
atgtggcacc ccaacattta tgagaatgga gatgtatgca tttcgattct tcatccgcct     300
gtagatgacc cacagagtgg agaactgcct tctgaaaggt ggaatcctac tcagaatgtg     360
aggactatcc tattaagtgt aatctcactg cttaatgagc ccaacacctt ctccccagcc     420

-continued

```
aatgtcgatg cttcagttat gttcaggaaa tggagagaca gtaaaggaaa agacaaagaa      480
tatgctgaaa ttattaggaa acaagtttca gccactaagg ccgaagcaga aaggatgga      540 gtgaaggtcc ccacaaccct ggcggaatac tgcatcaaaa ctaaagtgcc ttccaatgac      600
aacagctcag atttgcttta cgacgacttg tatgatgacg acattgatga tgaagatgag      660
gaggaggaag atgccgactg ttatgatgat gatgattctg ggaatgagga gtcgtga        717
```

<210> SEQ ID NO 71
<211> LENGTH: 834
<212> TYPE: DNA
<213> ORGANISM: Artificial Sequence
<220> FEATURE:
<223> OTHER INFORMATION: cDNA sequence encoding a fusion protein
      including the E3 RING motif of gp78, UCE E2-25K protein and
      peptide linker

<400> SEQUENCE: 71

```
atggaggcca ggtttgcagt tgcaactcca gaggagctgg ctgtcaacaa tgacgactgt       60
gccatctgtt gggactccat gcaggctgcg cggaaactgc cctgtggaca tcttttccac      120
aactcctgtc ttcgttcctg gctagaacaa gacacctcct gtccaacatg cagaatgtct      180
cttaatattg ccgacaataa tcgtgtcagg gaagaaggta ccggatccca tatggccaac      240
atcgcggtgc agcgaatcaa gcgggagttc aaggaggtgc tgaagagcga ggagacgagc      300
aaaaatcaaa ttaaagtaga tcttgtagat gagaattta cagaattaag aggagaaata      360
gcaggacctc cagacacacc atatgaagga ggaagatacc aactagagat aaaaatacca      420
gaaacatacc catttaatcc ccctaaggtc cggtttatca ctaaaatatg catcctaat      480 attagttccg tcacaggggc tatttgtttg gatatcctga agatcaatg ggcagctgca      540 atgactctcc gcacggtatt attgtcattg caagcactat tggcagctgc agagccagat      600
gatccacagg atgctgtagt agcaaatcag tacaaacaaa atcccgaaat gttcaaacag      660
acagctcgac tttgggcaca tgtgtatgct ggagcaccag tttctagtcc agaatacacc      720
aaaaaaatag aaaacctatg tgctatgggc tttgatagga atgcagtaat agtggccttg      780
tcttcaaaat catgggatgt agagactgca acagaattgc ttctgagtaa ctga           834
```

<210> SEQ ID NO 72
<211> LENGTH: 332
<212> TYPE: PRT
<213> ORGANISM: Artificial Sequence
<220> FEATURE:
<223> OTHER INFORMATION: fusion protein including the gp78 RING motif,
      UCE E2 Ubc7 protein, peptide linker

<400> SEQUENCE: 72

```
Met Glu Ala Arg Phe Ala Val Ala Thr Pro Glu Glu Leu Ala Val Asn
1               5                   10                  15

Asn Asp Asp Cys Ala Ile Cys Trp Asp Ser Met Gln Ala Ala Arg Lys
                20                  25                  30

Leu Pro Cys Gly His Leu Phe His Asn Ser Cys Leu Arg Ser Trp Leu
            35                  40                  45

Glu Gln Asp Thr Ser Cys Pro Thr Cys Arg Met Ser Leu Asn Ile Ala
        50                  55                  60

Asp Asn Asn Arg Val Arg Glu Glu Gly Thr Gly Ser His Met Ala Gly
65                  70                  75                  80

Thr Ala Leu Lys Arg Leu Met Ala Glu Tyr Lys Gln Leu Thr Leu Asn
                85                  90                  95
```

```
Pro Pro Glu Gly Ile Val Ala Gly Pro Met Asn Glu Asn Phe Phe
            100                 105                 110
Glu Trp Glu Ala Leu Ile Met Gly Pro Glu Asp Thr Cys Phe Glu Phe
        115                 120                 125
Gly Val Phe Pro Ala Ile Leu Ser Phe Pro Leu Asp Tyr Pro Leu Ser
    130                 135                 140
Pro Pro Lys Met Arg Phe Thr Cys Glu Met Phe His Pro Asn Ile Tyr
145                 150                 155                 160
Pro Asp Gly Arg Val Cys Ile Ser Ile Leu His Ala Pro Gly Asp Asp
                165                 170                 175
Pro Met Gly Tyr Glu Ser Ser Ala Glu Arg Trp Ser Pro Val Gln Ser
            180                 185                 190
Val Glu Lys Ile Leu Leu Ser Val Val Ser Met Leu Ala Glu Pro Asn
        195                 200                 205
Asp Glu Ser Gly Ala Asn Val Asp Ala Ser Lys Met Trp Arg Asp Asp
    210                 215                 220
Arg Glu Gln Phe Tyr Lys Ile Ala Lys Gln Ile Val Gln Lys Ser Leu
225                 230                 235                 240
Gly Leu Leu Lys Leu Gly Thr Gly Ala Ser Gly Thr Ser Gly Ser Gly
                245                 250                 255
Met Gln Ile Phe Val Lys Thr Leu Thr Gly Lys Thr Ile Thr Leu Glu
            260                 265                 270
Val Glu Pro Ser Asp Thr Ile Glu Asn Val Lys Ala Lys Ile Gln Asp
        275                 280                 285
Lys Glu Gly Ile Pro Pro Asp Gln Gln Arg Leu Ile Phe Ala Gly Lys
    290                 295                 300
Gln Leu Glu Asp Gly Arg Thr Leu Ser Asp Tyr Asn Ile Gln Lys Glu
305                 310                 315                 320
Ser Thr Leu His Leu Val Leu Arg Leu Arg Gly Gly
                325                 330
```

<210> SEQ ID NO 73
<211> LENGTH: 996
<212> TYPE: DNA
<213> ORGANISM: Artificial Sequence
<220> FEATURE:
<223> OTHER INFORMATION: cDNA sequence encoding a fusion protein
      including the gp78 RING motif, UCE E2 Ubc7 protein, peptide linker

<400> SEQUENCE: 73

```
atggaggcca ggtttgcagt tgcaactcca gaggagctgg ctgtcaacaa tgacgactgt      60
gccatctgtt gggactccat gcaggctgcg cggaaactgc cctgtggaca tctttttccac    120
aactcctgtc ttcgttcctg ctagaacaa gacacctcct gtccaacatg cagaatgtct     180
cttaatattg ccgacaataa tcgtgtcagg gaagaaggta ccggatccca tatggcgggg     240
accgcgctca gaggctgat ggccgagtac aaacaattaa cactgaatcc tccggaagga      300
attgtagcag gccccatgaa tgaagagaac tttttttgaat gggaggcatt gatcatgggc    360
ccagaagaca cctgctttga gtttggtgtt tttcctgcca tcctgagttt cccacttgat     420
tacccgttaa gtccccccaaa gatgagattt acctgtgaga tgtttcatcc caacatctac   480
cctgatggga gagtctgcat ttccatcctc acgcgccag gcgatgaccc catgggctac      540
gagagcagcg cggagcggtg gagtcctgtg cagagtgtgg agaagatcct gctgtcggtg    600
gtgagcatgc tggcagagcc caatgacgaa agtggagcta acgtggatgc gtccaaaatg    660
tggcgcgatg accgggagca gttctataag attgccaagc agatcgtcca gaagtctctg    720
```

```
ggactgttaa agcttggcac cggcgctagc ggcactagtg gaagtggaat gcagatcttc    780
gtcaagacgt taaccggtaa aaccataact ctagaagttg aaccatccga taccatcgaa    840
aacgttaagg ctaaaattca agacaaggaa ggcattccac ctgatcaaca agattgatc    900 tttgccggta agcagctcga ggacggtaga acgctgtctg attacaacat tcagaaggag    960
tcgaccttac atcttgtctt aagactaaga ggtggt                              996
```

<210> SEQ ID NO 74
<211> LENGTH: 74
<212> TYPE: PRT
<213> ORGANISM: Homo sapiens

<400> SEQUENCE: 74

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

<210> SEQ ID NO 75
<211> LENGTH: 277
<212> TYPE: PRT
<213> ORGANISM: Artificial Sequence
<220> FEATURE:
<223> OTHER INFORMATION: fusion protein including the gp78 RING motif,
      UCE E2-25K protein and peptide linker

<400> SEQUENCE: 75

Met Glu Ala Arg Phe Ala Val Ala Thr Pro Glu Glu Leu Ala Val Asn
1               5                   10                  15

Asn Asp Asp Cys Ala Ile Cys Trp Asp Ser Met Gln Ala Ala Arg Lys
            20                  25                  30

Leu Pro Cys Gly His Leu Phe His Asn Ser Cys Leu Arg Ser Trp Leu
        35                  40                  45

Glu Gln Asp Thr Ser Cys Pro Thr Cys Arg Met Ser Leu Asn Ile Ala
    50                  55                  60

Asp Asn Asn Arg Val Arg Glu Glu Gly Thr Gly Ser His Met Ala Asn
65                  70                  75                  80

Ile Ala Val Gln Arg Ile Lys Arg Glu Phe Lys Glu Val Leu Lys Ser
                85                  90                  95

Glu Glu Thr Ser Lys Asn Gln Ile Lys Val Asp Leu Val Asp Glu Asn
            100                 105                 110

Phe Thr Glu Leu Arg Gly Glu Ile Ala Gly Pro Pro Asp Thr Pro Tyr
        115                 120                 125

Glu Gly Gly Arg Tyr Gln Leu Glu Ile Lys Ile Pro Glu Thr Tyr Pro
    130                 135                 140

Phe Asn Pro Pro Lys Val Arg Phe Ile Thr Lys Ile Trp His Pro Asn
145                 150                 155                 160

Ile Ser Ser Val Thr Gly Ala Ile Cys Leu Asp Ile Leu Lys Asp Gln
                165                 170                 175

Trp Ala Ala Ala Met Thr Leu Arg Thr Val Leu Leu Ser Leu Gln Ala
            180                 185                 190

```
Leu Leu Ala Ala Ala Glu Pro Asp Asp Pro Gln Asp Ala Val Val Ala
        195                 200                 205

Asn Gln Tyr Lys Gln Asn Pro Glu Met Phe Lys Gln Thr Ala Arg Leu
    210                 215                 220

Trp Ala His Val Tyr Ala Gly Ala Pro Val Ser Ser Pro Glu Tyr Thr
225                 230                 235                 240

Lys Lys Ile Glu Asn Leu Cys Ala Met Gly Phe Asp Arg Asn Ala Val
                245                 250                 255

Ile Val Ala Leu Ser Ser Lys Ser Trp Asp Val Glu Thr Ala Thr Glu
            260                 265                 270

Leu Leu Leu Ser Asn
        275

<210> SEQ ID NO 76
<211> LENGTH: 41
<212> TYPE: PRT
<213> ORGANISM: Homo sapiens

<400> SEQUENCE: 76

Cys Thr Ile Cys Leu Ser Ile Leu Glu Glu Gly Glu Asp Val Arg Arg
1               5                   10                  15

Leu Pro Cys Met His Leu Phe His Gln Val Cys Val Asp Gln Trp Leu
            20                  25                  30

Ile Thr Asn Lys Lys Cys Pro Ile Cys
        35                  40

<210> SEQ ID NO 77
<211> LENGTH: 41
<212> TYPE: PRT
<213> ORGANISM: Homo sapiens

<400> SEQUENCE: 77

Cys Val Ile Cys Phe Glu Arg Tyr Lys Pro Asn Asp Ile Val Arg Ile
1               5                   10                  15

Leu Thr Cys Lys His Phe Phe His Lys Asn Cys Ile Asp Pro Trp Ile
            20                  25                  30

Leu Pro His Gly Thr Cys Pro Ile Cys
        35                  40

<210> SEQ ID NO 78
<211> LENGTH: 41
<212> TYPE: PRT
<213> ORGANISM: Homo sapiens

<400> SEQUENCE: 78

Cys Val Val Cys Phe Asp Thr Tyr Lys Pro Gln Asp Val Val Arg Ile
1               5                   10                  15

Leu Thr Cys Lys His Phe Phe His Lys Ala Cys Ile Asp Pro Trp Leu
            20                  25                  30

Leu Ala His Arg Thr Cys Pro Met Cys
        35                  40

<210> SEQ ID NO 79
<211> LENGTH: 41
<212> TYPE: PRT
<213> ORGANISM: Homo sapiens

<400> SEQUENCE: 79

Cys Ala Val Cys Ile Glu Leu Tyr Lys Pro Asn Asp Leu Val Arg Ile
1               5                   10                  15
```

```
Leu Thr Cys Asn His Ile Phe His Lys Thr Cys Val Asp Pro Trp Leu
            20                  25                  30

Leu Glu His Arg Thr Cys Pro Met Cys
        35                  40

<210> SEQ ID NO 80
<211> LENGTH: 47
<212> TYPE: PRT
<213> ORGANISM: Homo sapiens

<400> SEQUENCE: 80

Cys Arg Ile Cys His Cys Glu Gly Asp Asp Glu Ser Pro Leu Ile Thr
1               5                   10                  15

Pro Cys His Cys Thr Gly Ser Leu His Phe Val His Gln Ala Cys Leu
            20                  25                  30

Gln Gln Trp Ile Lys Ser Ser Asp Thr Arg Cys Cys Glu Leu Cys
        35                  40                  45

<210> SEQ ID NO 81
<211> LENGTH: 56
<212> TYPE: PRT
<213> ORGANISM: Homo sapiens

<400> SEQUENCE: 81

Cys Arg Ile Cys Gln Met Ala Ala Ala Ser Ser Ser Asn Leu Leu Ile
1               5                   10                  15

Glu Pro Cys Lys Cys Thr Gly Ser Leu Gln Tyr Val His Gln Asp Cys
            20                  25                  30

Met Lys Lys Trp Leu Gln Ala Lys Ile Asn Ser Gly Ser Ser Leu Glu
        35                  40                  45

Ala Val Thr Thr Cys Glu Leu Cys
    50                  55

<210> SEQ ID NO 82
<211> LENGTH: 42
<212> TYPE: PRT
<213> ORGANISM: Homo sapiens

<400> SEQUENCE: 82

Cys Val Ile Cys Gln Asp Gln Ser Lys Thr Val Leu Leu Leu Pro Cys
1               5                   10                  15

Arg His Leu Cys Leu Cys Gln Ala Cys Thr Glu Ile Leu Met Arg His
            20                  25                  30

Pro Val Tyr His Arg Asn Cys Pro Leu Cys
        35                  40
```

METHODS AND COMPOSITIONS RELATING TO E3 RING-E2 FUSION PROTEINS

REFERENCE TO RELATED APPLICATION

This application claims priority from U.S. Provisional Patent Application Ser. No. 61/104,079, filed Oct. 9, 2008, the entire content of which is incorporated herein by reference.

FIELD OF THE INVENTION

The present invention relates generally to selective proteolysis and the ubiquitin-proteasome system. In specific embodiments of the present invention, compositions and methods relate to E3 RING:E2 fusion proteins.

BACKGROUND OF THE INVENTION

The ubiquitin-proteasome system (UPS) is a selective proteolysis pathway. In the UPS, a cellular protein, after being modified by polyubiquitylation, is targeted to the proteasome for proteolysis. Polyubiquitylation is a posttranslational modification process that requires a member of the ubiquitin-conjugating enzymes (also known as E2 enzymes), which works in concert with a member of the ubiquitin protein ligases (also known as E3 enzymes). E2 carries an activated ubiquitin as a thiolester complex (E2~Ub) and docks onto E3, which contains a substrate protein binding site, and successive transfer of the ubiquitin in E2~Ub to the E3-bound substrate leads to polyubiquitylation of a substrate protein. In this process, the discharged E2 leaves after each cycle and is reconverted into the E2~Ub form through the action of the ubiquitin-activating enzyme (also known as E1). For the targeting of a protein to the proteasome, this polyubiquitination requires the formation of a polyubiquitin chain in which the K48 residue in ubiquitin serves as the linkage for ubiquitin chain elongation. Other forms of polyubiquitin linkages (K29, K11 and K63) are also found, and these polyubiquitin chains are used for other functions unrelated to UPS.

Protein degradation via UPS serves a wide range of important functions, some of which are essential for cell and animal survival. This process is used in the regulation of many gene transcription events in response to environmental changes. For example the activation of NFkB in inflammatory response is mediated by the selective degradation of IkB, and the selective degradation of HIF1 provides a means to exercise control on the transcription of genes under hypoxia. Other examples are provided by cell cycle transition and checkpoint controls where the expression of specific regulatory proteins is regulated in part by their selective degradation via UPS. UPS is also used in protein quality control in which misfolded or damaged proteins can be selectively removed by degradation.

There is a continuing need for compositions and methods for identifying modulators of UPS mediated protein degradation.

SUMMARY OF THE INVENTION

Compositions are provided according to embodiments of the present invention which include an isolated fusion protein including an E3 protein RING motif bonded to an UCE E2 protein. In preferred embodiments, the C-terminus of the E3 protein RING motif is bonded to the N-terminus of the UCE E2 protein by an intervening peptide linker. Optionally, the peptide linker is 5-50 amino acids. Preferred is a peptide linker of 15-20 amino acids. In a further option, the linker is a non-peptide linker.

In particular embodiments, an isolated fusion protein of the present invention include an E3 protein RING motif selected from the group consisting of: human ubiquitin-protein ligase gp78; yeast ubiquitin-protein ligase Doa10; human ubiquitin-protein ligase RNF13; human ubiquitin-protein ligase RNF38; human ubiquitin-protein ligase TEB4; human ubiquitin-protein ligase RNF139 also known as trc8; human ubiquitin-protein ligase RNFx2; human ubiquitin-protein ligase RNF126; human ubiquitin-protein ligase Hrd1; and human ubiquitin-protein ligase MARCH1.

In further embodiments, an isolated fusion protein of the present invention includes a portion of an E3 protein having the structure $CXXC(X)_{n1}CX(H/C)(X)_{n2}(H/C)XXC(X)_{n3}CXXC$, where C is a cysteine, H is a histidine, n1 is in the range of 11-14, inclusive, n2 is in the range of 2-7, inclusive and n3 is in the range of 10-20, inclusive, and X is any amino acid, with the proviso that identified cysteines and histidines in the structure $CXXC(X)_{n1}CX(H/C)(X)_{n2}(H/C)XXC(X)_{n3}CXXC$ remain constant; an E2 protein and a linker disposed between the portion of the E3 protein and the E2 protein.

Optionally, an isolated fusion protein according to embodiments of the present invention includes a UCE E2 protein selected from the group consisting of: Ubc7, E2-25K, Cdc34 and Cdc34b.

In particular embodiments, an isolated fusion protein according to embodiments of the present invention includes: gp78 E3 protein RING motif and E2 Ubc7; Doa10 E3 protein RING motif and E2 Ubc7; RNF13 E3 protein RING motif and E2 Ubc7; RNF38 E3 protein RING motif and E2 Ubc7; TEB4 E3 protein RING motif and E2 Ubc7; RNF139 E3 protein RING motif and E2 Ubc7; RNFx2 E3 protein RING motif and E2 Ubc7; RNF126 E3 protein RING motif and E2 Ubc7; Hrd1 E3 protein RING motif and E2 Ubc7; or MARCH1 E3 protein RING motif and E2 Ubc7.

In particular embodiments, an isolated fusion protein according to embodiments of the present invention includes: gp78 E3 protein RING motif and E2-25K; RNF38 E3 protein RING motif and E2-25K; or RNF126 E3 protein RING motif and E2-25K.

Compositions according to particular embodiments of the present invention include an isolated fusion protein including a portion of an E3 protein selected from the group consisting of: SEQ ID No. 8, 14, 20, 26, 32, 38, 44, 50, 56 and 62, an E2 protein selected from the group consisting of: SEQ ID No. 1, 3, 5 and 69 and a linker adjoining the C-terminus of the portion of the E3 protein and the N-terminus of the E2 protein.

Compositions according to particular embodiments of the present invention include an isolated fusion protein including a portion of an E3 protein selected from the group consisting of: SEQ ID No. 8, 26 and 50, an E2-25K protein, and a linker adjoining the C-terminus of the portion of the E3 protein and the N-terminus of the E2 protein.

In some embodiments, an isolated fusion protein according to embodiments of the present invention further includes a ubiquitylation substrate. In preferred embodiments, the N-terminus of the ubiquitylation substrate is bonded to the C-terminus of the UCE E2 protein, directly or indirectly such as by a linker. Ubiquitin is an illustrative ubiquitylation substrate included in an isolated fusion protein according to embodiments of the present invention.

In a further option, an isolated fusion protein according to embodiments of the present invention further includes a ubiquitylation substrate binding moiety. In preferred embodiments, the N-terminus of the ubiquitylation substrate binding moiety is bonded to the C-terminus of the UCE E2 protein, directly or indirectly such as by a linker.

Methods of identifying ubiquitylation modulators are provided according to embodiments of the present invention which include contacting an isolated fusion protein including an E3 protein RING motif bonded to an UCE E2 protein with a ubiquitylation substrate in the presence of a test substance. Ubiquitylation of the ubiquitylation substrate is then detected to determine the effect of the test substance on ubiquitylation of the ubiquitylation substrate. Further embodiments of methods of the present invention include contacting the fusion protein with a ubiquitylation substrate in the absence of the test substance and comparing ubiquitylation of the ubiquitylation substrate in the presence and absence of the test substance, thereby identifying a modulator of ubiquitylation.

In particular embodiments of the present invention, the ubiquitylation substrate includes a first mutant ubiquitin having a substitution mutation at K48. Any amino acid other than lysine is substituted for lysine at K48. For example, the first mutant ubiquitin having a substitution mutation at K48 is K48R, where arginine is substituted for lysine.

A second mutant ubiquitin is included in embodiments of inventive assays wherein the second mutant ubiquitin is unable to form a thiolester linkage with a UCE E2 protein due to substitution, truncation or extension at the C-terminus of ubiquitin. An example of the second mutant ubiquitin is C-terminus truncated ubiquitin Ub74.

Isolated nucleotide sequences encoding a fusion protein including an E3 protein RING motif bonded to an UCE E2 protein are provided according to embodiments of the present invention. In preferred embodiments, the isolated nucleotide sequence encodes a fusion protein in which the C-terminus of the E3 protein RING motif is bonded to the N-terminus of the UCE E2 protein by an intervening peptide linker.

In particular embodiments, isolated nucleotide sequences encode a fusion protein including a portion of an E3 protein having the structure $CXXC(X)_{n1}CX(H/C)(X)_{n2}(H/C)XXC(X)_{n3}CXXC$, where C is a cysteine, H is a histidine, n1 is in the range of 11-14, inclusive, n2 is in the range of 2-7, inclusive and n3 is in the range of 10-20, inclusive, and X is any amino acid, with the proviso that identified cysteines and histidines in the structure $CXXC(X)_{n1}CX(H/C)(X)_{n2}(H/C)XXC(X)_{n3}CXXC$ remain constant; an E2 protein and a linker disposed between the portion of the E3 protein and the E2 protein.

In particular embodiments of the present invention isolated nucleotide sequences encoding a fusion protein include a nucleotide sequence encoding a portion of an E3 protein selected from the group consisting of: SEQ ID No. 8, 14, 20, 26, 32, 38, 44, 50, 56 and 62 and a nucleotide sequence encoding an E2 protein selected from the group consisting of: SEQ ID No. 1, 3, 5 and 69. In further embodiments, isolated nucleotide sequences encoding a fusion protein of the present invention also include a nucleotide sequence encoding a linker adjoining the C-terminus of the portion of the E3 protein and the N-terminus of the E2 protein.

Recombinant vectors including a nucleotide sequence encoding a fusion protein including an E3 protein RING motif bonded to an UCE E2 protein are provided according to embodiments of the present invention. Recombinant vectors of the present invention include various types of vectors, including for example cloning vectors and expression vectors.

Host cells including an isolated nucleotide sequence encoding a fusion protein including an E3 protein RING motif bonded to an UCE E2 protein are provided according to embodiments of the present invention.

BRIEF DESCRIPTION OF THE DRAWINGS

FIG. 3 is a sequence alignment of three types of E3 RING motifs which can be included in fusion proteins according to embodiments of the present invention;

DETAILED DESCRIPTION OF THE INVENTION

Figure 1:
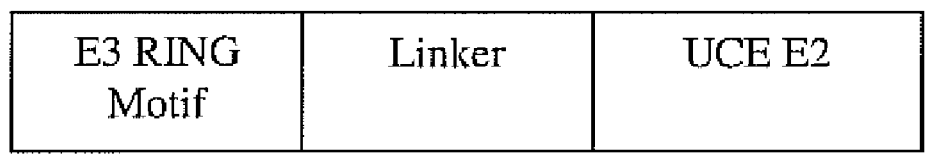
FIG. 1 is a schematic diagram of fusion proteins according to embodiments of the present invention.

Compositions and methods for identifying UPS modulators are provided according to embodiments of the present invention.

Fusion proteins and methods of the present invention are provided which include modified ubiquitin conjugating enzyme (UCE) E2 and E3 proteins. The fusion proteins and methods have utility for, among other uses, modulating UPS mediated protein degradation and for identifying UPS modulators.

E3 RING:E2 fusion proteins of the present invention facilitate the detection of ubiquitylation modulators, particularly ubiquitylation inhibitors, in ubiquitylation assays. Analysis of ubiquitylation assay kinetics illustrates the effects of E3 RING:E2 fusion proteins in ubiquitylation assays.

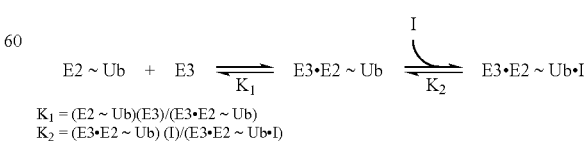

$K_1 = (E2 \sim Ub)(E3)/(E3 \cdot E2 \sim Ub)$
$K_2 = (E3 \cdot E2 \sim Ub)(I)/(E3 \cdot E2 \sim Ub \cdot I)$ In a reaction where E3·E2~Ub is the active enzyme species, the velocity (V) of the reaction is proportional to k (E3·E2~Ub). Where F is the fraction of total E3 in the E2~Ub·E3 complex state, F=(E3·E2~Ub)/[(E3)+(E3·E2~Ub)+(E3·E2~Ub·I)] and F=[(E2~Ub)(1/K$_1$)]/[1+(E2~Ub)(1/K$_1$)+(E2~Ub)(I)(1/K$_1$)(1/K$_2$)]. Thus, V is proportional to k (E3)$_T$(F).

In assays where E2~Ub>>K$_1$, i.e. most E3 is in the E2·E3 complex state, for example 10 times, then F=10/(1+10) in the absence of an inhibitor (I), and when I=K$_2$, F=10/(1+10+10). That is the 50% inhibition as expected.

In assays where (E2~Ub)<<K$_1$, in order to achieve detectable inhibition it would be necessary to employ a concentration of I such that the value of (I)/K$_2$ approaches the value of K$_1$/(E2~Ub). For example if E2~Ub is 0.01 K$_1$, then F=0.01/[1+0.01+0.01*[(I)/(K$_2$)] and when I is 100K$_2$, then you have 0.01/(1+1) and 50% inhibition. Thus, E3 RING:E2 fusion proteins of the present invention allow for increased E3·E2~Ub and facilitate detection of ubiquitylation modulators.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; and B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004.

The terms "polypeptide," "peptide" and "protein" are used interchangeably to refer to a chain of amino acids linked by peptide bonds. These terms also refer to oligopeptides having from 2- about 10 peptide bond linked amino acids and polypeptides having about 10 or more peptide bond linked amino acids. These terms further encompass proteins including synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

The term "fusion protein" refers to a protein which includes at least two proteins bonded through their respective amino- and carboxyl termini to form a single polypeptide. The proteins included in the fusion protein can be in direct linkage through a peptide bond or can be joined indirectly, through a linker.

The term "isolated" as used herein refers to a substance that has been separated from contaminating cellular components associated with the substance in nature not intended to be associated with the substance and that would interfere with use of the substance in assays or other uses. The term isolated used herein also refers to non-naturally occurring nucleic acids and proteins, such as fusion proteins according to embodiments of the present invention and nucleic acids encoding the fusion proteins since such non-naturally occurring nucleic acids and proteins are not found in nature. An "isolated" material may be, but is not necessarily, pure. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology is described in S. Doonan, Protein Purification Protocols Humana Press, 1996.

In particular embodiments, fusion proteins of the present invention include an E3 protein, or portion thereof, fused to a UCE E2 protein, or portion thereof.

Fusion proteins according to embodiments of the present invention have the general structure schematically shown in FIG. 1. FIG. 1 illustrates an E3 RING motif joined to the N-terminus of the UCE E2 protein wherein both the E3 RING motif and the UCE E2 protein are joined to an intervening linker.

The inventive fusion proteins are active to transfer ubiquitin to a ubiquitylation substrate in a ubiquitylation reaction.

In preferred embodiments, fusion proteins of the present invention include a polypeptide including an E3 protein RING motif fused to an UCE E2 protein, or portion thereof.

The terms "E3 ubiquitin ligase," "E3 protein," "ubiquitin-protein ligase" and "ubiquitin ligase" are used interchangeably herein to refer to ubiquitin ligases which are enzymes that mediate the covalent attachment of ubiquitin to a ubiquitylation substrate. As used herein, these terms also refer to naturally occurring variants of a given E3 ubiquitin ligase and recombinantly prepared variants of a given E3 ubiquitin ligase, as well as functional fragments thereof.

Non-limiting examples of E3 proteins include: human ubiquitin-protein ligase gp78, also known as autocrine motility factor receptor, isoform 2; yeast ubiquitin-protein ligase Doa10; human ubiquitin-protein ligase RNF13; human ubiquitin-protein ligase RNF38; human ubiquitin-protein ligase TEB4; human ubiquitin-protein ligase RNF139 also known as trc8; human ubiquitin-protein ligase RNFx2; human ubiquitin-protein ligase RNF126; human ubiquitin-protein ligase Hrd1; and human ubiquitin-protein ligase MARCH1.

Fusion proteins according to embodiments of the present invention can include any of various E3 RING motifs including, but not limited to, the RING motif of E3 proteins gp78, Doa10, RNF13, RNF38, TEB4, RNF139 (trc8), RNFx2, RNF126, Hrd1 or MARCH1.

The terms "E3 RING motif," "E3 RING" refer to a pattern in an amino acid sequence functional to activate unanchored K48-polyUb chain synthesis activity in UCE E2 protein. As used herein, the term "E3 RING" also refers to naturally occurring variants of a given E3 RING motif and recombinantly prepared variants of a given E3 RING motif, as well as functional fragments thereof.

Figure 2:
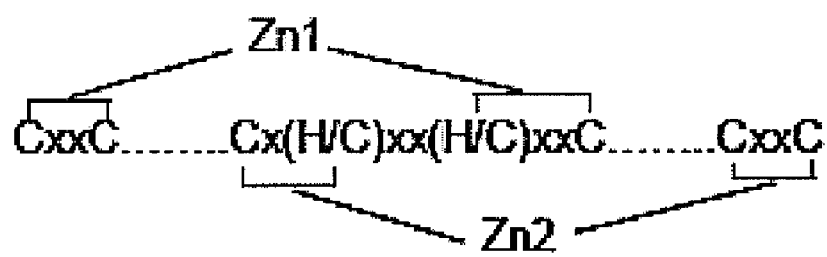
FIG. 2 is a diagram illustrating zinc-binding motifs of three types of E3 RING motifs which can be included in fusion proteins according to embodiments of the present invention.

An E3 RING motif is defined by the sequence motif CXXC(X)$_{n1}$CX(H/C)(X)$_{n2}$(H/C)XXC(X)$_{n3}$CXXC, where C is a cysteine, H is a histidine, n1 is in the range of 11-14, inclusive, n2 is in the range of 2-7, inclusive and n3 is in the range of 10-20, inclusive, and X is any amino acid. An E3 RING motif included in a fusion protein of the present invention can be any E3 RING motif, including those described as Type I, II or III, illustrated in FIG. 2, which are differentiated on the basis of placement of the Zn coordination histidine residue(s).

Exemplary E3 RING motif sequences are illustrated in FIG. 3.

The E3 RING motif amino acid sequences of Type I, II and III activate unanchored K48-polyUb chain synthesis activity in UCE E2 Ubc7 proteins. Zn-coordinating residues are highlighted in dark shading. Also highlighted in grey is a common tryptophan.

The E3 RING motif amino acid sequences of gp78, RNF38 and RNF126 activate unanchored K48-polyUb chain synthesis activity in UCE E2-25K proteins.

Particular E3 RING motifs that can be included in E3 RING:E2 fusion proteins of the present invention are described in Kikkert M, Doolman R, Dai M, Avner R, Hassink G, van Voorden S, Thanedar S, Roitelman J, Chau V, Wiertz E. (2004) Human HRD1 is an E3 ubiquitin ligase involved in degradation of proteins from the endoplasmic reticulum. J Biol Chem.; 279:3525-34; Hassink, G. C., Kikkert, M., van Voorden, S., Lee, S. J., Spaapen, R., van Laar, T., Coleman, C. S., Bartee, E., Fruh, K., Chau, V. and Wiertz, E. J. (2005) TEB4 is a C4HC3 RING finger-containing ubiquitin ligase of the endoplasmic reticulum. Biochem J. 388: 647-655; Flierman, D., Coleman, C. S., Pickart C. M., Rapoport T. A., and Chau, V. (2006) E2-25K Mediates US11-triggered Retro-translocation of MHC Class I Heavy Chains in a Permeabilized Cell System. Proc. Natl. Acad. Sci. USA 103: 11589-11594.

A polypeptide including an E3 RING motif can be a truncated E3 protein. In particular embodiments, a truncated E3 protein includes a flanking peptide of about 1-20 amino acids adjacent the N-terminus of the E3 RING motif and/or 1-20 amino acids adjacent the C-terminus of the E3 RING motif as all or part of a linker.

As noted above, FIG. 1 illustrates an E3 RING motif joined to the N-terminus of the UCE E2 protein wherein both the E3 RING motif and the UCE E2 protein are joined to an intervening linker. The linker can be any length, as long as the fusion protein is enzymatically active. The linker is preferably a peptide linker of about 5-50 amino acids. In particular embodiments, the linker is a peptide linker of about 15-20 amino acids.

A linker peptide includes a portion of an E3 protein which is located adjacent the C-terminus of the E3 RING motif of an E3 protein in embodiments of fusion proteins of the present invention. The linker preferably includes a 5-50 amino acid portion of an E3 protein which is located adjacent the C-terminus of the E3 RING motif of an E3 protein. In particular embodiments, the linker preferably includes a 15-20 amino acid portion of an E3 protein which is located adjacent the C-terminus of the E3 RING motif of an E3 protein.

In a further option, a linker is a non-peptide linker.

The terms "E2 ubiquitin conjugating enzyme," "UCE E2," "E2 protein," and "ubiquitin conjugating enzyme" are used interchangeably herein to refer to enzymes that interact with ubiquitin and an E3 protein in the ubiquitylation process. As used herein, these terms also refer to naturally occurring variants of a given UCE E2 protein and recombinantly prepared variants of a given UCE E2 protein, as well as functional fragments thereof.

The UCE E2 protein can be any UCE E2 protein, including but not limited to, Ubc7, E2-25K, Cdc34, Ubc4, and other UCE E2 proteins.

The amino acid sequence of human ubiquitin conjugating enzyme E2 protein Ubc-7, also known as Homo sapiens ubiquitin-conjugating enzyme E2G 2, is designated SEQ ID No. 1:

MAGTALKRLMAEYKQLTLNPPEGIVAGPMNEENFFEWEALIMGPEDTCFE

FGVFPAILSFPLDYPLSPPKMRPTCEMFHPNIYPDGRVCISILHAPGDDP

MGYESSAERWSPVQSVEKILLSVVSMLAEPNDESGANVDASKMWRDDREQ

FYKIAKQIVQKSLGL

A nucleotide sequence encoding human E2 protein Ubc-7 is designated SEQ ID No. 2:

atggcgggaccgcgctcaagaggctgatggccgagtacaaacaattaac actgaatcctccggaaggaattgtagcaggccccatgaatgaagagaact tttttgaatgggaggcattgatcatgggcccagaagacacctgctttgag tttggtgttttcctgccatcctgagtttcccacttgattacccgttaag tcccccaaagatgagatttacctgtgagatgtttcatcccaacatctacc ctgatgggagagtctgcatttccatcctccacgcgccaggcgatgacccc atgggctacgagagcagcgcggagcggtggagtcctgtgcagagtgtgga gaagatcctgctgtcggtggtgagcatgctggcagagcccaatgacgaaa gtggagctaacgtggatgcgtccaaaatgtggcgcgatgaccgggagcag ttctataagattgccaagcagatcgtccagaagtctctgggactgtga The amino acid sequence of human ubiquitin conjugating enzyme E2 protein E2-25k is designated SEQ ID No. 3:

MANIAVQRIKREFKEVLKSEETSKNQIKVDLVDENFTELRGEIAGPPDTP

YEGGRYQLEIKIPETYPFNPPKVRFITKIWHPNISSVTGAICLDILKDQW

AAAMTLRTVLLSLQALLAAAEPDDPQDAVVANQYKQNPEMFKQTARLWAH

VYAGAPVSSPEYTKKIENLCAMGFDRNAVIVALSSKSWDVETATELLLSN

A nucleotide sequence encoding human ubiquitin conjugating enzyme E2 protein E2-25k is designated SEQ ID No. 4:

atggccaacatcgcggtgcagcgaatcaagcgggagttcaaggaggtgct gaagagcgaggagacgagcaaaaatcaaattaaagtagatcttgtagatg agaattttacagaattaagaggagaaatagcaggacctccagacacacca tatgaaggaggaagataccaactagagataaaaataccagaaacataccc atttaatccccctaaggtccggtttatcactaaaatatggcatcctaata ttagttccgtcacaggggctatttgtttggatatcctgaaagatcaatgg gcagctgcaatgactctccgcacggtattattgtcattgcaagcactatt ggcagctgcagagccagatgatccacaggatgctgtagtagcaaatcagt acaaacaaaatcccgaaatgttcaaacagacagctcgactttgggcacat gtgtatgctggagcaccagtttctagtccagaatacaccaaaaaaataga aaacctatgtgctatgggctttgataggaatgcagtaatagtggccttgt cttcaaaatcatgggatgtagagactgcaacagaattgcttctgagtaac tga The amino acid sequence of human E2 protein Cdc-34 is designated SEQ ID No. 5:

MARPLVPSSQKALLLELKGLQEEPVEGFRVTLVDEGDLYNWEVAIFGPPN

TYYEGGYFKARLKFPIDYPYSPPAFRFLTKMWHPNIYETGDVCISILHPP

VDDPQSGELPSERWNPTQNVRTILLSVISLLNEPNTFSPANVDASVMYRK

WKFSKGKDREYTDIIRKQVLGTKVDAERDGVKVPTTLAEYCVKTKAPAPD

EGSDLFYDDYYEDGEVEEEADSCFGDDEDDSGTEES

A nucleotide sequence encoding human E2 protein Cdc-34 is designated SEQ ID No. 6:

```
atggctcggccgctagtgcccagctcgcagaaggcgctgctgctggagct
caaggggctgcaggaagagccggtcgagggattccgcgtgacactggtgg
acgagggcgatctatacaactgggaggtggccatcttcgggcccccaac
acctactacgagggcggctacttcaaggcgcgcctcaagttccccatcga
ctacccatactctccaccagcctttcggttcctgaccaagatgtggcacc
ctaacatctacgagacgggggacgtgtgtatctccatcctccaccgccg
gtggacgaccccagagcggggagctgccctcagagaggtggaacccac
gcagaacgtcaggaccattctcctgagtgtgatctccctcctgaacgagc
ccaacaccttctcgcccgcaaacgtggacgcctccgtgatgtacaggaag
tggaagagagcaaggggaaggatcgggagtacacagacatcatccggaa
gcaggtcctggggaccaaggtggacgcggagcgtgacggcgtgaaggtgc
ccaccacgctggccgagtactgcgtgaagaccaaggcgccggcgcccgac
gagggctcagacctcttctacgacgactactacgaggacggcgaggtgga
ggaggaggccgacagctgcttcggggacgatgaggatgactctggcacgg
aggagtcc
```

The amino acid sequence of human E2 protein Cdc-34b is designated SEQ ID No. 69:

```
MAQQQMTSSQKALMLELKSLQEEPVEGFRITLVDESDLYNWEVAIFGPPN
TLYEGGYFKAHIKFPIDYPYSPPTFRFLTKMWHPNIYENGDVCISILHPP
VDDPQSGELPSERWNPTQNVRTILLSVISLLNEPNTFSPANVDASVMFRK
WRDSKGKDKEYAEIIRKQVSATKAEAEKDGVKVPTTLAEYCIKTKVPSND
NSSDLLYDDLYDDDIDDEDEEEEDADCYDDDDSGNEES
```

A nucleotide sequence encoding human E2 protein Cdc-34b is designated SEQ ID No. 70:

```
atggcccagcagcagatgaccagctcgcagaaggccctgatgctcgagct
gaaatccctgcaggaggaaccggtggagggcttccggatcaccctggtgg
acgagtccgacctctacaactgggaggtggccatcttcggacccccaac
accctctacgaaggcggctacttcaaggcgcatattaaattcctattga
ctacccctattcaccacctaccttcagattcttgaccaaaatgtggcacc
ccaacatttatgagaatggagatgtatgcatttcgattcttcatccgcct
gtagatgacccacagagtggagaactgccttctgaaaggtggaatcctac
tcagaatgtgaggactatcctattaagtgtaatctcactgcttaatgagc
ccaacaccttctccccagccaatgtcgatgcttcagttatgttcaggaaa
tggagagacagtaaaggaaaagacaaagaatatgctgaaattattaggaa
acaagtttcagccactaaggccgaagcagaaaaggatggagtgaaggtcc
ccacaaccctggcggaatactgcatcaaaactaaagtgccttccaatgac
aacagctcagatttgctttacgacgacttgtatgatgacacattgatga
tgaagatgaggaggaggaagatgccgactgttatgatgatgatgattctg
ggaatgaggagtcgtga
```

In particular embodiments, the term "variant" refers to a protein characterized by an amino acid sequence substantially similar to a reference amino acid sequence and which retains substantially similar functional properties compared to the reference amino acid sequence. A substantially similar amino acid sequence has at least 80%, or at least 85%, 90%, 91%, 92%, 93%, 94%, 95%, 96%, 97%, 98%, 99%, or greater, amino acid sequence identity to a reference amino acid sequence.

When referring to an "E3 RING," the term variant refers to an amino acid sequence motif $CXXC(X)_{n1}CX(H/C)(X)_{n2}(H/C)CXC(X)_{n3}CXXC$, where C is a cysteine, H is a histidine, n1 is in the range of 11-14, inclusive, n2 is in the range of 2-7, inclusive and n3 is in the range of 10-20, inclusive, and X is any amino acid, wherein the amino acid sequence has at least 80%, or at least 85%, 90%, 91%, 92%, 93%, 94%, 95%, 96%, 97%, 98%, 99%, or greater, amino acid sequence identity to a reference E3 RING amino acid sequence, with the proviso that identified cysteines and histidines in the amino acid sequence motif $CXXC(X)_{n1}CX(H/C)(X)_{n2}$ $(H/C)XXC(X)_{n3}CXXC$ remain constant.

A variant can be an ortholog of a reference protein. The term "ortholog" refers to the functional counterpart in a second species of a nucleic acid or protein obtained from a first species. Thus, for example, mouse ubiquitin is the ortholog of human ubiquitin. In preferred embodiments, proteins and protein fragments included in fusion proteins of the present invention are human proteins and fragments of human proteins. Orthologs of human proteins and protein fragments can be used from any of various species, including, without limitation, organisms including mammals, birds, reptiles, amphibians, insects, plants, microorganisms and eukaryotic microorganisms such as yeast.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid. Nucleotide sequences are disclosed herein that encode particular proteins and fusion proteins. It is appreciated that due to the degenerate nature of the genetic code, alternate nucleic acid sequences encode a given protein, and that any of such alternate nucleic acids may be included in an expression vector and expressed to produce a protein, including fusion proteins, described herein.

Variants of proteins described herein are encoded by nucleotide sequences which are substantially similar to a reference sequence. In embodiments of the present invention, a substantially similar nucleotide sequence is characterized as having a complementary nucleotide sequence capable of hybridizing to a nucleotide sequence encoding a reference amino acid sequence under high stringency hybridization conditions.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5× Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, a reference nucleic acid will hybridize to the complement of substantially identical targets and not to unrelated sequences.

Mutations can be introduced using standard molecular biology techniques, such as site-directed mutagenesis and PCR-mediated mutagenesis. One of skill in the art will recognize that one or more amino acid mutations can be introduced without altering the functional properties of a reference peptide or protein. For example, one or more amino acid substitutions, additions, or deletions can be made without altering the functional properties of a reference peptide or protein.

Conservative amino acid substitutions can be made in a reference peptide or protein to produce a variant. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and)(BLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

Fusion proteins of the present invention are made using well-known techniques of molecular biology, for example, as described in standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004.

In particular embodiments, an expression cassette is provided according to embodiments of the present invention which includes a nucleic acid sequence encoding an E3 RING motif, a UCE E2 protein and a peptide linker disposed between the E3 RING motif and UCE E2 protein. The nucleic acid sequence is expressed to produce a fusion protein of the present invention.

The nucleic acid sequence encoding an E3 RING motif, a UCE E2 protein and a peptide linker disposed between the E3 RING motif and UCE E2 protein is operably linked to one or more regulatory nucleic acid sequences which facilitates expression of the nucleic acid sequence in an appropriate host cell and/or in a cell-free expression system. A promoter is a regulatory nucleic acid sequence preferably included in an expression cassette of the present invention. An expression cassette can be generated recombinantly or synthetically using well-known methodology.

An expression cassette can be incorporated into a vector, such as an expression vector and/or cloning vector. The term "vector" refers to a recombinant nucleic acid vehicle for transfer of a nucleic acid. Exemplary vectors are plasmids, cosmids, viruses and bacteriophages. Particular vectors are known in the art and one of skill in the art will recognize an appropriate vector for a specific purpose.

A host cell for expression of given protein or peptide can be prokaryotic or eukaryotic, such as bacterial, plant, insect, fungus, yeast, and mammalian cells.

The term "operably linked" refers to a nucleic acid in functional relationship with a second nucleic acid. A regulatory nucleic acid sequence is illustratively a promoter, an enhancer, a DNA and/or RNA polymerase binding site, a ribosomal binding site, a polyadenylation signal, a transcription start site, a transcription termination site or an internal ribosome entry site (IRES).

Optionally, the expression cassette also encodes a polyhistidine tag peptide to facilitate purification of the expressed fusion protein. The tag can be cleaved following purification.

An expression vector is introduced into a host cell using well-known techniques such as infection or transfection, including calcium phosphate transfection, liposome-mediated transfection, electroporation and sonoporation. Expression constructs and methods for their generation and use to express a desired protein are known in the art, as described, for example, in Sambrook et al., Molecular Cloning: A Laboratory Manual, Cold Spring Harbor Laboratory Press, 2001; Ausubel, F. et al., (Eds.), Protocols in Molecular Biology, Wiley, 2002; and S. J. Higgins and B. D. Hames (Eds.), Protein Expression: A Practical Approach, Oxford University Press, USA, 1999.

In particular embodiments of the present invention, components of an inventive fusion protein, such as an E3 RING motif, linker and/or UCE E2 protein are attached by chemical conjugation.

The components of an inventive fusion protein, such as an E3 RING motif, linker and UCE E2 protein can be produced by recombinant methodology or chemical synthesis. For example, a specified peptide or protein can be produced using solid phase synthesis, solution phase synthesis, partial solid phase synthesis or fragment condensation. The components of an inventive fusion protein can then be chemically conjugated to produce a fusion protein.

Conjugation chemistries used in conjugation of peptide, proteins and non-protein linkers illustratively include coupling agents such as, but not limited to, glutaraldehyde, carbodiimide, succinimde esters, benzidine, periodate, isothionate and combinations of these. For example, a E3 RING motif and an UCE E2 protein can be modified to include an appropriate functional group and/or protective group at one or both termini of each of the E3 RING motif and UCE E2 protein, if desired. One of skill in the art can determine appropriate functional groups and appropriate conjugation chemistries for fusion of the individual components of a fusion protein, such as a E3 RING motif and UCE E2 protein.

Mutants of E3 RING motif and UCE E2 proteins are included in compositions and methods of the present invention. In particular embodiments, E3 RING motif and UCE E2 proteins in fusion proteins described herein include 1, 2, 3, 4, 5, 6, 7, 8, 9, 10 or more amino acid substitutions, deletions or additions compared to a wild-type E3 RING motif or UCE E2 protein.

In embodiments of the present invention, certain amino acids in the E3 RING motif and/or UCE E2 protein are substituted with another amino acid in order to modify a functional characteristic of a fusion protein including the mutant E3 RING motif and/or UCE E2 protein.

Figure 4A:
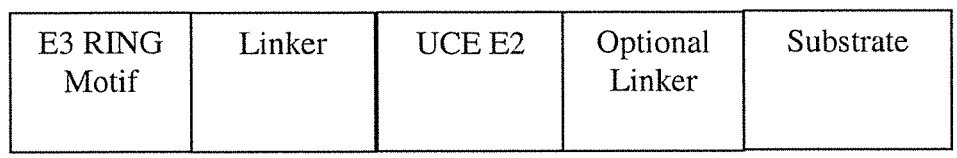
FIG. 4A is a schematic diagram of fusion proteins according to embodiments of the present invention.

A fusion protein according to embodiments of the present invention optionally further includes an ubiquitylation substrate. For example, a fusion protein according to embodiments of the present invention has the general structure shown in the schematic diagram in FIG. 4A.

The ubiquitylation substrate can be any naturally occurring or synthetic ubiquitylation substrate.

A linker is preferably disposed between the E2 protein and the substrate. The linker can be any length, as long as the fusion protein is enzymatically active to catalyze an ubiquitylation reaction, adding ubiquitin to the substrate. The linker is preferably a peptide linker of about 1-20 amino acids. In particular embodiments, the linker is a peptide linker of about 10-15 amino acids. In a further option, a linker is a non-peptide linker.

Figure 4B:
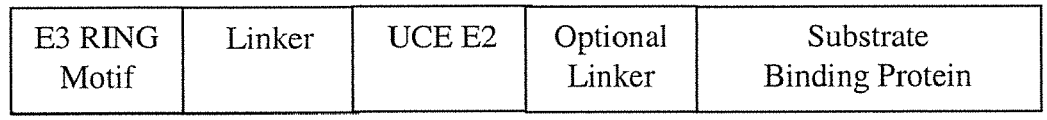
FIG. 4B is a schematic diagram of fusion proteins according to embodiments of the present invention.

A fusion protein according to embodiments of the present invention optionally further includes an ubiquitylation substrate binding moiety. For example, a fusion protein according to embodiments of the present invention has the general structure shown in the schematic diagram in FIG. 4B.

Ubiquitylation substrate binding proteins included in the fusion protein can be any ubiquitylation substrate binding protein, such as an antibody, a receptor, a lectin or a fragment of any of these or other ubiquitylation substrate binding protein effective to bind an ubiquitylation substrate.

Methods of inhibiting a target protein are provided according to embodiments of the present invention which include contacting the target protein with a fusion protein having an E3 protein RING motif linked to an UCE E2 protein, or fragment thereof, and an ubiquitylation substrate binding moiety linked to the UCE E2 protein. The fusion protein is characterized by activity to transfer ubiquitin to an ubiquitylation substrate which is bound to the binding moiety. The target protein can be in vitro or in vivo.

Methods of inhibiting a target protein according to embodiments of the present invention can be used to decrease levels of the target protein in a cell, tissue or organism. For example, a particular protein associated with deleterious effects in a disease state can be inhibited using compositions and methods of the present invention Assays Methods of identifying a modulator of ubiquitylation are provided according to embodiments of the present invention which include contacting an E3 RING:E2 fusion protein and a ubiquitylation substrate in the presence of a test substance. Also included in particular embodiments of inventive assays is contacting an E3 RING:E2 fusion protein with a ubiquitylation substrate in the absence of the test substance. Ubiquitylation of the ubiquitylation substrate is detected and ubiquitylation of the ubiquitylation substrate in the presence and absence of the test substance is compared, thereby identifying an increase or decrease in ubiquitylation in the presence of the test substance.

The term "test substance" refers to any substance, naturally occurring or synthetic, to be tested for the capacity to directly or indirectly modulate the activity of a fusion protein of the present invention to ubiquitinylate a ubiquitinylation substrate relative to a control. A test substance can be any molecule or mixture of molecules, for example, a small organic molecule, a protein, a polysaccharide, lipid or nucleic acid. A test substance can be a complex mixture of molecules, such as a cell extract. A test substance can be in the form of a mixture of compounds, exemplified by a library of compounds, such as a combinatorial or randomized library.

The term "modulator" refers to molecules that are identified using an assay according to embodiments of the present invention that increases, decreases, facilitates, sensitizes or otherwise affects the activity of a fusion protein of the present invention to ubiquitinylate a ubiquitinylation substrate relative to a control.

In particular embodiments, an assay including a test substance is compared to an assay without the test substance to examine the effect of the test substance on ubiquitylation of a ubiquitinylation substrate or unanchored polyubiquitin chain synthesis. Inhibition of ubiquitylation is achieved when the ubiquitinylation activity of the fusion protein in the presence of the test substance is about 80% or less, 75% or less, 70% or less, 65% or less, 60% or less, 55% or less, 50% or less, 45% or less, 40% or less, 35% or less, 30% or less, 25% or less, 20% or less, 15% or less, or 10% or less compared to the ubiquitinylation activity of the fusion protein in the absence of the test substance. Activation of ubiquitylation is achieved when the ubiquitylation activity of the fusion protein in the presence of the test substance is about 110% or greater, 150% or greater, 200% or greater, 500% or greater, 1000% or greater, or 5000% or greater compared to the ubiquitylation activity of the fusion protein in the absence of the test substance.

In preferred embodiments, assays of the present invention are performed under ubiquitylation reaction conditions. The term "ubiquitylation reaction conditions" refers to chemical reaction conditions in which reaction components ubiquitylate a ubiquitylation substrate. Ubiquitylation reaction conditions according to the present invention include an E3 RING:E2 fusion protein of the present invention, a UCE E1 protein or functional fragment thereof and a ubiquitylation substrate. An assay according to embodiments of the present invention can be performed in cells or under cell-free conditions. Additional aspects of ubiquitylation reaction conditions include, for example, suitable reaction temperature, pH and identity of reaction medium where present, cofactors such as $MgCl_2$ and ATP, all of which are known in the art. U.S. Pat. Nos. 6,737,244; and 7,132,234 describe such aspects of exemplary ubiquitylation reaction conditions.

A ubiquitylation substrate included in an assay according to embodiments of the present invention can be any of various naturally occurring or synthetic substrates capable of having a ubiquitin moiety covalently attached by a ubiquitylation reaction. Ubiquitylation substrates are well known in the art and include ubiquitin itself. In a particular embodiment, the ubiquitylation substrate is K48 of ubiquitin.

The amino acid sequence of human ubiquitin:

(SEQ ID No. 7)
MQIFVKTLTGKTITLEVEPSDTIENVKAKIQDKEGIPPDQQRLIFAGKQL

EDGRTLSDYNIQKESTLHLVLRLRGG.

As used herein, the term "ubiquitin" also refers to naturally occurring variants of a given ubiquitin protein and recombinantly prepared variants of a given ubiquitin protein, as well as functional fragments thereof.

The terms "UCE E1" and E1 protein refer to ubiquitin activating enzyme E1. As used herein, these terms also refer to isolated naturally occurring variants of a given UCE E1 protein and isolated recombinantly prepared variants of a given UCE E1 protein, as well as functional fragments thereof.

The amino acid sequence of human ubiquitin Ub74:

(SEQ ID No. 74)
MQIFVKTLTGKTITLEVEPSDTIENVKAKIQDKEGIPPDQQRLIFAGKQL

EDGRTLSDYNIQKESTLHLVLRLR.

The amino acid sequence of human ubiquitin activating enzyme E1 is identified as SEQ ID No. 68:

MSSSPLSKKRRVSGPDPKPGSNCSPAQSVLSEVPSVPTNGMAKNGSEADI

DEGLYSRQLYVLGHEAMKRLQTSSVLVSGLRGLGVEIAKNIILGGVKAVT

LHDQGTAQWADLSSQFYLREEDIGKNRAEVSQPRLAELNSYVPVTAYTGP

LVEDFLSGFQVVVLTNTPLEDQLRVGEFCHNRGIKLVVADTRGLFGQLFC

DFGEEMILTDSNGEQPLSAMVSMVTKDNPCVVTCLDEARHGFESGDFVSF

SEVQGMVELNGNQPMEIKVLGPYTFSICDTSNFSDYIRGGIVSQVKVPKK

-continued

ISFKSLVASLAEPDFVVTDFAKFSRPAQLHIGFQALHQFCAQHGRPPRPR

NEEDAAELVALAQAVNARALPAVQQNNLDEDLIRKLAYVAAGDLAPINAF

IGGLAAQEVMKACSCKFMPIMQWLYFDALECLPEDKEVLTEDKCLQRQNR

YDGQVAVFCSDLQEKLGKQKYFLVGAGAIGCELLKNFAMIGLGCGEGGEI

IVTDMDTIEKSNLNRQFLFRPWDVTKLKSDTAAAAVRQMNPHIRVTSHQN

RVGPDTERIYDDDFFQNLDGVANALDNVDARMYMDRRCVYYRKPLLESGT

LGTKGNVQVVIPPFLTESYSSSQDPPEKSIPICTLKNFPNAIEHTLQWARD

EFEGLFKQPAENVNQYLTDPKFVERTLRLAGTQPLEVLEAVQRSLVLQRP

QTWADCVTWACHHWHTQYSNNIRQLLHNFPPDQLTSSGAPFWSGPKRCPH

PLTFDVNNPLHLDYVMAAANLFAQTYGLTCSQDRAAVATFLQSVQVPEFT

PKSGVKIHVSDQELQSANASVDDSRLEELKATLPSPDKLPGFKMYPIDFE

KDDDSNFHMDFIVAASNLRAENYDIPSADRHKSKLIAGKIIPAIATTTAA

VVGLVCLELYKVVQGHRQLDSYKNGFLNLALPFFGFSEPLAAPRHQYYNQ

EWTLWDRFEVQGLQPNGEEMTLKQFLDYFKTEHKLEITMLSQGVSMLYSF

FMPAAKLKERLDQPMTEIVSRVSKRKLGRHVRALVLELCCNDESGEDVEV

PYVRYTIR

Ubiquitylation of a ubiquitylation substrate can be detected by any of various well-known techniques. For example, ubiquitylation detection can include detection of labeled ubiquitin, such as radiolabelled or fluorescently labeled ubiquitin. In particular embodiments, immunodetection can be included, for example, using a ubiquitin-specific antibody or antibody fragment to detect ubiquitylation.

In one embodiment, ubiquitylation is detected by detection of relatively small multimers, particularly dimers, of modified ubiquitin.

Figure 8A:
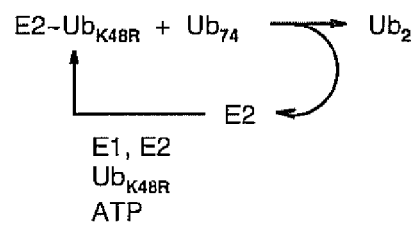
FIG. 8A is a schematic diagram of an activity assay reaction according to embodiments of the present invention.

FIG. 8A shows a reaction scheme relating to an embodiment of a ubiquitylation assay of the present invention. Two ubiquitin mutants are included in the assay. A first ubiquitin mutant is a K48 mutant in which any amino acid, X, is substituted for lysine at position 48 (K48). In such mutants, the E2UbK48X is stable since the thiolester-linked UbK48X cannot be transferred to UbK48X to form K48-specific Ub dimers. A second ubiquitin mutant included in the reaction is modified such that it is unable to form thiolester linkage with a UCE E2 protein. Any ubiquitin mutant which does not have the usual C-terminal gly-gly can be used in this capacity. Thus, for example, the second ubiquitin mutant can be Ub75, having one C-terminal glycine removed. In another example, the second ubiquitin mutant can be Ub74, having the two C-terminal glycines removed. In a further example, 1-4 C-terminal amino acids can be removed such that a C-terminal truncated ubiquitin is included in embodiments of an inventive assay. Alternatively, one or both C-terminal glycines can be substituted by any other amino acid. In a further option, the C-terminus of ubiquitin can be extended by 1 or more amino acids such that the C-terminal glycines are unavailable to form thiolester linkage with a UCE E2 protein.

In a particular embodiment of this assay mutant ubiquitin is used in which the lysine at position 48 (K48) is replaced with arginine, resulting in the mutant ubiquitin termed UbK48R. In a reaction where E2~Ub is formed with the UbK48R mutant replacing ubiquitin (Ub), the E2~UbK48R is stable since the thiolester-linked UbK48R cannot be transferred to UbK48R to form K48-specific Ub dimer. The assay reaction mixture also contains a second ubiquitin mutant species, termed Ub74, where the C-terminal Gly-Gly sequence in Ub is not present. The thiolester-linked UbK48R can be transferred to K48 present in Ub74, resulting in the formation of a UbK48R-Ub74 dimer ($Ub_2$). This ubiquitin dimer ($Ub_2$) lacks the free C-terminal Gly residue in wild type Ub dimer and is therefore unable to form thiolester linkage with E2. Likewise, this $Ub_2$ lacks the free K48 residue in a wild type ubiquitin dimer and is therefore unable to accept the transfer of UbK48R to form trimeric ubiquitin. The formation of $Ub_2$ can be used to determine the activity of E2 or E3 RING-E2 fusion protein, in the presence or absence of a test substance.

Ubiquitin multimers, including dimers, can be detected by any of various detection methods, including, but not limited to, immunodetection or detection of a detectably labeled ubiquitin multimers or dimer.

The terms "detectably labeled" and "detectable label" refers to a material capable of producing a signal indicative of the presence of a detectably labeled nucleic acid by any appropriate method illustratively including spectroscopic, optical, photochemical, biochemical, enzymatic, electrical and/or immunochemical. Examples of detectable labels illustratively include a fluorescent moiety, a chemiluminescent moiety, a bioluminescent moiety, a magnetic particle, an enzyme, a substrate, a radioisotope and a chromophore. In a preferred embodiment, a detectable label is a fluorescent label.

Embodiments of inventive compositions and methods are illustrated in the following examples. These examples are provided for illustrative purposes and are not considered limitations on the scope of inventive compositions and methods.

EXAMPLES

Example 1

Plasmid Constructs

Coding sequences for E3 RING motifs and human E2 proteins are obtained by separate polymerase chain reactions (PCR), using either a HeLa cell cDNA library or specific IMAGE cDNA clones (ATCC) as templates. The E3 RING-E2 fusion coding sequence can be created by fusing the two PCR products using standard techniques of DNA cloning to create ends suitable for ligation. An initiation methionine for the E3 RING-E2 fusion can be introduced either in the PCR product or may be supplied by an expression vector. The 3' end of the E3 RING coding sequence and the 5' end of the E2 PCR products contain a sequence that specifies a common restriction site that can be used to ligate the two PCR products to generate an in frame E3 RING-E2 fusion sequence. The ligated coding sequence of E3 RING-E2 can be introduced into any number of expression vectors by standard molecular biology procedures. In this example, the E3 RING PCR product contains the sequence CATATG 5' upstream of the E3 RING coding sequence; this sequence provides an Nde1 site for cloning purposes as well as the ATG serving as the initiation codon. The 3' RING coding sequence is followed by the Kpn1 restriction site sequence of GGTACC followed by the BamH1 restriction site sequence. In the PCR product of the E2 coding sequence, the sequence is flanked by the restriction site sequence for BamH1 and HindIII at the 5' and 3' end respectively of the E2 coding sequence. Digestion by BamH1 and HindIII, followed by ligation yields the desired cDNA that encodes the E3 RING-E2 fusion with a linker sequence of GTGSH due to the presence of the Kpn1 and BamH1 restriction site sequences as well as the CAT sequence present in the Nde1 site in the ligated nucleotide product. This product can be introduced into an expression vector where a coding sequence can be inserted between an Nde1 and a HindIII restriction site. In this example, a pET28(a+) vector (Novagen) is used in which a nucleotide sequence encoding the peptide sequence of MGSSHHHHHHDYDIPSTENLY-FQG has been inserted between the Nco1 and the Nde1 restriction sites so that this polypeptide will be fused to the N-terminus of the E3 RING-E2 fusion when the latter coding sequence is inserted between the Nde1 and HindIII sites in the modified pET28(a+) vector.

Example 2

A fusion protein including the E3 RING sequence motif of gp78 and human E2 Ubc7 protein is constructed as described in Example 1.

The RING motif in gp78 is located at residue positions 341-378 in the full-length gp78 sequence. The amino acid sequence of E3 RING motif of gp78 is designated SEQ ID No. 8:

```
CAICWDSMQAARKLPCGHLFHNSCLRSWLEQDTSCPTC.
```

A cDNA sequence encoding the E3 RING motif of gp78 is designated SEQ ID No. 9:

```
tgtgccatctgttgggactccatgcaggctgcgcggaaactgccctgtgg
acatcttttccacaactcctgtcttcgttcctggctagaacaagacacct
cctgtccaacatgc
```

In this example, the nucleotide sequence that encodes the amino acid residues 322 to 393 of the full-length gp78 protein is isolated and fused in frame to the nucleotides encoding the full-length human Ubc7 E2 enzyme. Amino acid residues 322 to 393 of the full-length gp78 E3 protein have the sequence designated SEQ ID No. 10:

```
MEARFAVATPEELAVNNDDCAICWDSMQAARKLPCGHLFHNSCLRSWLEQ
DTSCPTCRMSLNIADNNRVREE
```

This sequence includes 19 amino acids N-terminal to the first cysteine of the RING motif as well as 15 amino acids following the last cysteine in the RING motif.

A cDNA sequence encoding amino acid residues 322 to 393 of the full-length gp78 sequence is designated SEQ ID No. 11:

```
atggaggccaggtttgcagttgcaactccagaggagctggctgtcaacaa
tgacgactgtgccatctgttgggactccatgcaggctgcgcggaaactgc
cctgtggacatcttttccacaactcctgtcttcgttcctggctagaacaa
gacacctcctgtccaacatgcagaatgtctcttaatattgccgacaataa
tcgtgtcagggaagaa
```

The amino acid sequence of a fusion protein including the gp78 E3 RING motif, Ubc7 UCE E2 protein and peptide linker disposed between the E3 RING motif and the Ubc7 UCE E2 protein is designated SEQ ID No. 12:

```
MEARFAVATPEELAVNNDDCAICWDSMQAARKLPCGHLFHNSCLRSWLEQ
DTSCPTCRMSLNIADNNRVREEGTGSHMAGTALKRLMAEYKQLTLNPPEG
IVAGPMNEENFFEWEALIMGPEDTCFEFGVFPAILSFPLDYPLSPPKMRF
TCEMFHPNIYPDGRVCISILHAPGDDPMGYESSAERWSPVQSVEKILLSV
VSMLAEPNDESGANVDASKMWRDDREQFYKIAKQIVQKSLGL
```

A cDNA sequence encoding a fusion protein including the gp78 E3 RING motif, Ubc7 UCE E2 protein and a peptide linker disposed between the E3 RING motif and the Ubc7 UCE E2 protein is designated SEQ ID No. 13:

```
atggaggccaggtttgcagttgcaactccagaggagctggctgtcaacaa
tgacgactgtgccatctgttgggactccatgcaggctgcgcggaaactgc
cctgtggacatcttttccacaactcctgtcttcgttcctggctagaacaa
gacacctcctgtccaacatgcagaatgtctcttaatattgccgacaataa
tcgtgtcagggaagaaggtaccggatcccatatggcggggaccgcgctca
agaggctgatggccgagtacaaacaattaacactgaatcctccggaagga
attgtagcaggccccatgaatgaagagaactttttttgaatgggaggcatt
gatcatgggcccagaagacacctgctttgagtttggtgttttcctgcca
tcctgagtttcccacttgattacccgttaagtccccccaaagatgagattt
acctgtgagatgtttcatcccaacatctaccctgatgggagagtctgcat
ttccatcctccacgcgccaggcgatgacccatgggctacgagagcagcg
cggagcggtggagtcctgtgcagagtgtggagaagatcctgctgtcggtg
gtgagcatgctggcagagcccaatgacgaaagtggagctaacgtggatgc
gtccaaaatgtggcgcgatgaccgggagcagttctataagattgccaagc
agatcgtccagaagtctctgggactgtga
```

Example 3

An exemplary scheme applicable for expression and purification of the E3 RING:E2 fusion proteins to homogeneity is described in this example.

For purposes of cloning and protein purification, a poly-Histag, a Tev cleavage site and a linker is encoded in the DNA sequence of the expression cassette. In this example, to facilitate Ni-affinity chromatography purification, the fusion proteins are expressed with an N-terminal extension sequence of MGSSHHHHHHDYDIPSTENLYFQGH. Treatment of the expressed fusion protein with the Tobacco-Etch virus (TEV) protease generates the peptides MGSSHHHHHHDYDIPS-TENLYFQ and leaves the dipeptide GH at the N-terminus of the RING-E2 fusion protein.

Expression of E3 RING-E2 fusion proteins is carried out with the expression cassette encoding the E3 RING-E2 fusion protein inserted into a modified pET28 bacterial expression vector.

Bacteria harboring the expression plasmids are grown in liquid culture at 37° C. to an absorbance of 0.5, measured at 600 nm. The cultures are then adjusted to contain 1 mM IPTG (Isopropyl β-D-1-thiogalactopyranoside) to induce the expression of the fusion protein. The culture is grown for an additional 3 hours, harvested by centrifugation, lysed with BugBuster (Novagen) per manufacturer's protocol, and insoluble cell debris are removed by centrifugation at 20,000 rpm (about 50,000 g). Fusion protein is purified sequentially by Ni-affinity chromatography, Superdex-75 size exclusion chromatography, and anion exchange chromatography. For the Ni-Affinity chromatography, fusion protein is eluted from Ni-NTA beads with 25 mM Tris, pH 7.6 and 200 mM imidazole. Gel filtration is carried out with column equilibrated in 25 Tris pH 7.6 containing 0.05 M sodium chloride. The TEV protease cleavage is carried out on protein obtained after the gel filtration step. The cleaved protein is loaded onto a Q-sepharose column and eluted with a linear gradient of 0.05-0.4 M sodium chloride. The purification results in the yield of ~24 mg of apparently homogeneous protein from al L culture of bacteria.

Figure 5:
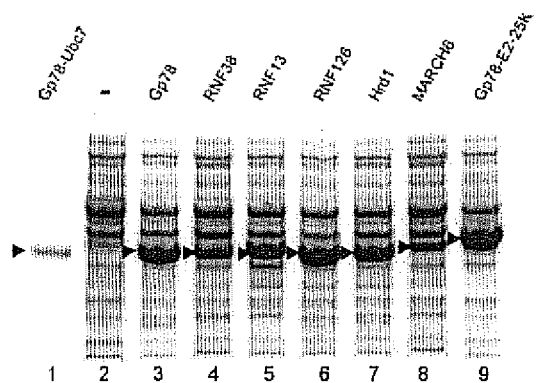
FIG. 5 shows an SDS-PAGE showing expressed fusion proteins according to embodiments of the present invention.

FIG. 5 shows expressed fusion proteins according to embodiments of the present invention from lysed bacterial extracts separated by SDS-PAGE and visualized by Coomassie-blue staining (lane 1). Extracts are prepared either from BL21 strain (Novagen) grown in liquid culture (lane 2) or with cells induced for the expression of specific RING-E2 fusions: gp78-Ubc7 (lane 3), RNF38-Ubc7 (lane 4), RNF13-Ubc7 (lane 5), RNF126-Ubc7 (lane 6), Hrd1-Ubc7 (lane 7), March6/TEB4-Ubc7 (lane 8) and gp78-E2-25K (lane 9).

Figure 6:
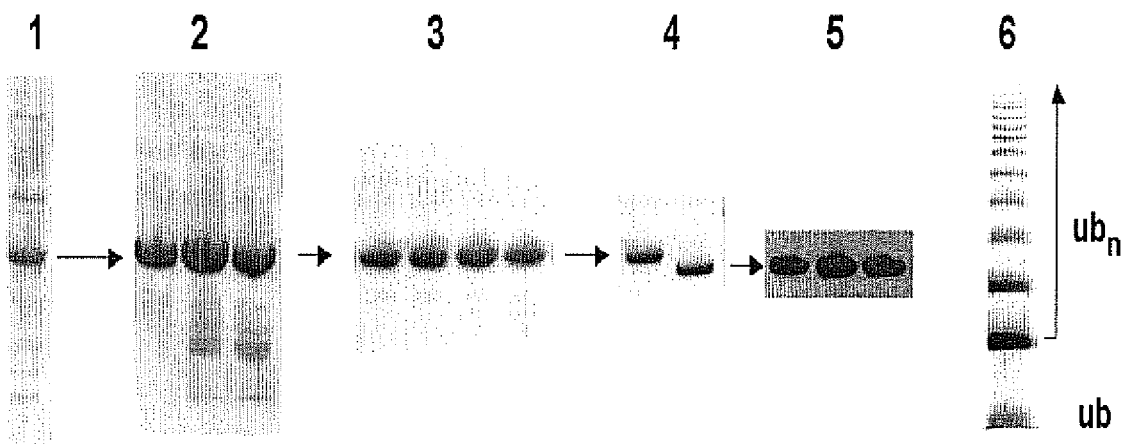
FIG. 6 shows SDS-PAGE of samples of an expressed fusion protein of the present invention at various stages of purification and showing results of an assay showing ubiquitylation activity of the expressed fusion protein.

FIG. 6 shows SDS-PAGE of samples of a representative expressed fusion protein (RNF126-Ubc7) of the present invention at various stages of purification: 1) lysed bacterial extract; 2) proteins after Ni-NTA chromatography; 3) proteins after gel filtration; 4) proteins after TEV protease cleavage; and 5) proteins after anion exchange.

Example 4

Activity Assay

Isolated fusion proteins are assayed for ubiquitylation activity. Broadly described, ubiquitin (Ub) of activated E2~Ub is transferred to K48 of another Ub molecule, forming Ub dimers and higher order polymers is detected and qualitatively or quantitatively evaluated. Ubiquitylation activity is allosterically stimulated by the presence of E3 RING motifs.

In this example, unanchored polyUb chain synthesis ubiquitylation activity assays are carried out in ubiquitylation reaction conditions at 25° C. in 25 mM Tris, pH7.5, 10 mM $MgCl_2$, 1 mM ATP, 10 nM E1, 20 μM Ub; and 0.1 μM of an E3 RING-E2 fusion protein of the present invention. FIG. 6 shows results of an assay showing ubiquitylation activity of the expressed fusion protein RNF126-Ubc7, showing ubiquitylation activity.

Example 5

Activity Assay

Figure 7:
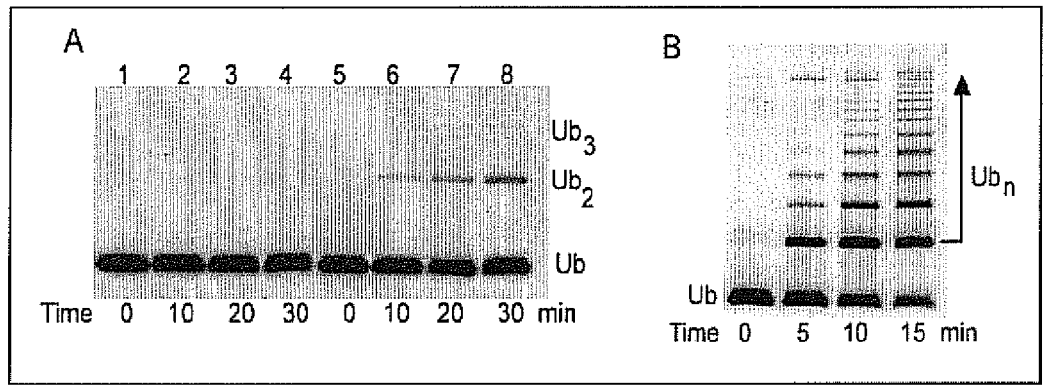
FIG. 7 shows an SDS-PAGE indicating results of the activity assay and the activity measurement of Ubc7, Ubc7 in the presence of the gp78 RING motif, and the fusion gp78 RING-Ubc7 fusion protein.

In a further example, FIG. 7 shows an SDS-PAGE indicating results of the activity assay and the activity measurement of Ubc7, Ubc7 in the presence of the gp78 RING motif, and the fusion gp78 RING-Ubc7 fusion protein. (Panel A) Lanes 1-4, time course of unanchored polyUb chain synthesis with 0.1 μM Ubc7 and 20 μM Ub; lanes 5-8, with 20 μM gp78RING motif added. (panel B) the same reaction carried out with 0.1 μM gp78RING-Ubc7 fusion. The reactions are carried out at 25° C. in 25 mM Iris, pH7.5, 10 mM $MgCl_2$, 1 mM ATP and 10 nM E1 in addition to the components indicated.

In these reactions, a modified ubiquitin is used where the N-terminus had been extended with the amino acid sequence MCHHHHHH and where the cysteine residue in this extension had been modified with Oregon Green iodoacetamide (Invitrogen). At specified times indicated, aliquots are withdrawn into SDS-sample buffer to stop the reaction, subjected to SDS-PAGE, and protein species containing the modified UbK48R visualized by using a fluorescent imager using excitation wavelength of 488 nm and emission of light at >510 nm. Note that the activity is much higher using the fusion protein.

Example 6

RING-E2 fusions form a stable complex. A crystal structure of gp78-Ubc7 fusion is solved to 2.2 Å resolution.

In the structure, the first 62 residues of the 72-residue gp78 RING motif are structured. Residues 63 to 72 are not in the electron density map, suggesting that this stretch of the sequence forms a flexible linker to the N-terminus of Ubc7.

Surface topology generated by bringing the gp78 RING, Ubc7 and ubiquitin together in Gp78 RING-Ubc7~Ub, formed at the interfaces of separate proteins, provides binding sites for modulators, such as small molecule modulators of ubiquitylation. For example, a modulator may inhibit the E2 activity by precluding substrate binding or the function of the active site residues in E2.

Example 7

Mutant Proteins

Site directed mutageneis is used to change particular amino acids in the E3 RING motif, UCE E2 protein, or both, in fusion proteins of the present invention. Particular mutants are used in assays of the present invention.

His94 is an active site residue in Ubc7 that is required to lower the pKa of substrate lysine for ubiquitin transfer.

Example 8

A fusion protein including the E3 RING sequence motif of Doa10 and the E2 Ubc7 protein is constructed.

The amino acid sequence of E3 RING motif of Doa10 is designated SEQ ID No. 14:

CRICRGEATEDNPLFHPCKCRGSIKYMHESCLLEWVASKNIDISKPGADV

KCDIC

The cDNA sequence encoding the E3 RING motif of Doa10 and additional Doa10 sequence is designated SEQ ID No. 15:

tgccgtatttgtcgtggagaagctactgaggacaatcctcttttccatcc ttgtaaatgcaggggctcaattaaatacatgcatgaatcctgtctgttag aatgggtagcttcaaaaaatatagacatttcaaaaccaggcgcggatgtt aaatgtgacatctgt The amino acid sequence used in the fusion protein in this example includes the E3 RING motif of Doa10 and additional Doa10 sequence and is designated SEQ ID No. 16:

MANEETDTATFNDDAPSGATCRICRGEATEDNPLFHPCKCRGSIKYMHES

CLLEWVASKNIDISKPGADVKCDICHYPIQFKTIYAENMPE

The cDNA sequence encoding the E3 RING motif of Doa10 and additional Doa10 sequence is designated SEQ ID No. 17:

atggcaaacgaggaaacagataccgccactttcaatgatgatgcgccatc cggcgccacctgccgtatttgtcgtggagaagctactgaggacaatcctc ttttccatccttgtaaatgcaggggctcaattaaatacatgcatgaatcc tgtctgttagaatgggtagcttcaaaaaatatagacatttcaaaaccagg cgcggatgttaaatgtgacatctgtcactatcccattcaattcaaaacga tatatgcggaaaacatgcccgaa The amino acid sequence of a fusion protein including the Doa10 E3 RING motif, Ubc7 UCE E2 protein and peptide linker disposed between the Doa10 E3 RING motif and the Ubc7 UCE E2 protein is designated SEQ ID No. 18:

MANEETDTATFNDDAPSGATCRICRGEATEDNPLFHPCKCRGSIKYMHES

CLLEWVASKNIDISKPGADVKCDICHYPIQFKTIYAENMPEGTGSHMAGT

ALKRLMAEYKQLTLNPPEGIVAGPMNEENFFEWEALIMGPEDTCFEFGVF

PAILSFPLDYPLSPPKMRFTCEMFHPNIYPDGRVCISILHAPGDDPMGYE

SSAERWSPVQSVEKILLSVVSMLAEPNDESGANVDASKMWRDDREQFYKI

AKQIVQKSLGL

A cDNA sequence encoding a fusion protein including the E3 RING motif of Doa10, Ubc7 UCE E2 protein and a peptide linker disposed between the Doa10 E3 RING motif and the Ubc7 UCE E2 protein is constructed essentially as described in Example 1 and designated SEQ ID No. 19:

atggcaaacgaggaaacagataccgccactttcaatgatgatgcgccatc cggcgccacctgccgtatttgtcgtggagaagctactgaggacaatcctc ttttccatccttgtaaatgcaggggctcaattaaatacatgcatgaatcc tgtctgttagaatgggtagcttcaaaaaatatagacatttcaaaaccagg cgcggatgttaaatgtgacatctgtcactatcccattcaattcaaaacga tatatgcggaaaacatgcccgaaggtaccggatcccatatggcggggacc gcgctcaagaggctgatggccgagtacaaacaattaacactgaatcctcc ggaaggaattgtagcaggcccatgaatgaagagaactttttttgaatggg aggcattgatcatgggcccagaagacacctgctttgagtttggtgttttt cctgccatcctgagtttcccacttgattacccgttaagtcccccaaagat gagatttacctgtgagatgtttcatcccaacatctaccctgatgggagag tctgcatttccatcctccacgcgccaggcgatgacccatgggctacgag agcagcgcggagcggtggagtcctgtgcagagtgtggagaagatcctgct gtcggtggtgagcatgctggcagagcccaatgacgaaagtggagctaacg tggatgcgtccaaaatgtggcgcgatgaccgggagcagttctataagatt gccaagcagatcgtccagaagtctctgggactgtga SEQ ID No. 19 is inserted into an expression vector as described in Example 1, expressed and purified as described in Example 3. The resulting isolated E3 RING:E2 fusion protein is assayed for ubiquitylation activity as described in Examples 4 and 5.

Example 9

A fusion protein including the E3 RING sequence motif of RNF13 and the E2 Ubc7 protein is constructed as described in Example 1.

The amino acid sequence of E3 RING motif of RNF13 is designated SEQ ID No. 20:

CAICLDEYEDGDKLRILPCSHAYHCKCVDPWLTKTKKTCPVC

A cDNA sequence encoding the E3 RING motif of RNF13 is designated SEQ ID No. 21:

tgtgccatttgtttggatgagtatgaagatggagacaaactcagaatcct tccctgttcccatgcttatcattgcaagtgtgtagacccttggctaacta aaaccaaaaaaacctgtccagtgtgc The amino acid sequence of E3 RING motif of RNF13 and additional RNF13 sequence is designated SEQ ID No. 22:

MQLKKLPVHKFKKGDEYDVCAICLDEYEDGDKLRILPCSHAYHCKCVDPW

LTKTKKTCPVCKQKVVPSQGDSD

A cDNA sequence encoding the E3 RING motif of RNF13 and additional sequence is designated SEQ ID No. 23:

atgcaacttaagaaacttcctgtacataaattcaagaaggagatgagta tgatgtatgtgccatttgtttggatgagtatgaagatggagacaaactca gaatccttccctgttcccatgcttatcattgcaagtgtgtagacccttgg ctaactaaaaccaaaaaaacctgtccagtgtgcaagcaaaaagttgttcc ttctcaaggcgattcagac The amino acid sequence of a fusion protein including the RNF13 E3 RING motif, Ubc7 UCE E2 protein and peptide linker disposed between the RNF13 E3 RING motif and the Ubc7 UCE E2 protein is designated SEQ ID No. 24:

MQLKKLPVHKFKKGDLYDVCAICLDEYEDGDKLRILPCSHAYHCKCVDPW

LTKTKKTCPVCKQKVVPSQGDSDGTGSHMAGTALKRLMAEYKQLTLNPPL

GIVAGPMNEENFFEWEALIMGPEDTCFEFGVFPAILSFPLDYPLSPPKMR

FTCEMFHPNIYPDGRVCISILHAPGDDPMGYESSAERWSPVQSVEKILLS

VVSMLALEPNDESGANVDASKMWRDDREQFYKIAKQWQKSLGL

A cDNA sequence encoding a fusion protein including the E3 RING motif of RNF13, Ubc7 UCE E2 protein and peptide linker disposed between the RNF13 E3 RING motif and the Ubc7 UCE E2 protein is designated SEQ ID No. 25:

atgcaacttaagaaacttcctgtacataaattcaagaaggagatgagta tgatgtatgtgccatttgtttggatgagtatgaagatggagacaaactca gaatccttccctgttcccatgcttatcattgcaagtgtgtagacccttgg -continued

```
ctaactaaaaccaaaaaaacctgtccagtgtgcaagcaaaaagttgttcc ttctcaaggcgattcagacggtaccggatcccatatggcggggaccgcgc tcaagaggctgatggccgagtacaaacaattaacactgaatcctccggaa ggaattgtagcaggccccatgaatgaagaaacttttttgaatgggaggc attgatcatgggcccagaagacacctgctttgagtttggtgtttttcctg ccatcctgagtttcccacttgattacccgttaagtccccaaagatgaga tttacctgtgagatgtttcatcccaacatctaccctgatgggagagtctg catttccatcctccacgcgccaggcgatgacccatgggctacgagagca gcgcggagcggtggagtcctgtgcagagtgtggagaagatcctgctgtcg gtggtgagcatgctggcagagcccaatgacgaaagtggagctaacgtgga tgcgtccaaaatgtggcgcgatgaccgggagcagttctataagattgcca agcagatcgtccagaagtctctgggactgtga
```

SEQ ID No. 25 is inserted into an expression vector as described in Example 1, expressed and purified as described in Example 3. The resulting isolated E3 RING:E2 fusion protein is assayed for ubiquitylation activity as described in Examples 4 and 5.

Example 6

A fusion protein including the E3 RING sequence motif of RNF38 and the E2 Ubc7 protein is constructed as described in Example 1.

The amino acid sequence of E3 RING motif of RNF38 is designated SEQ ID No. 26:

```
CVVCMCDFESRQLLRVLPCNHEFHAKCVDKWLKANRTCPIC
```

The cDNA sequence of the E3 RING motif of RNF38 is designated SEQ ID No. 27:

```
tgtgtagtatgcatgtgtgatttgagtcaaggcagctacttagagtctt accctgtaaccacgagttccatgccaagtgtgttgacaaatggcttaagg caaatcgtacttgcccaatttgc
```

The amino acid sequence of E3 RING motif of RNF38 and additional RNF38 sequence is designated SEQ ID No. 28:

```
MQLPSYRFNPNNHQSEQTLCVVCMCDFESRQLLRVLPCNHEFHAKCVDKW

LKANRTCPICRADASEVHRDSE
```

The cDNA sequence of the E3 RING motif of RNF38 and additional RNF38 sequences is designated SEQ ID No. 29:

```
atgcaacttccttcttatcggttcaatcctaacaaccaccagtcagaaca gactttgtgtgtagtatgcatgtgtgatttgagtcaaggcagctactta gagtcttaccctgtaaccacgagttccatgccaagtgtgttgacaaatgg cttaaggcaaatcgtacttgcccaatttgccgagctgatgcttcagaagt gcatcgggattcaaaa
```

The amino acid sequence of a fusion protein including the RNF38 E3 RING motif, Ubc7 UCE E2 protein and peptide linker disposed between the RNF38 E3 RING motif and the Ubc7 UCE E2 protein is designated SEQ ID No. 30:

```
MQLPSYRFNPNNHQSEQTLCVVCMCDFESRQLLRVLPCNHEFHAKCVDKW

LKANRTCPICRADASEVHRDSEGTGSHMAGTALKRLMAEYKQLTLNPPEG

IVAGPMNEENFFEWEALIMGPEDTCFEFGVFPAILSFPLDYPLSPPKMRF

TCEMFHPNIYPDGRVCISILHAPGDDPMGYESSAERWSPVQSVEKILLSV

VSMLAEPNDESGANVDASKMWRDDREQFYKIAKQIVQKSLGL
```

A cDNA sequence encoding a fusion protein including the E3 RING motif of RNF38, Ubc7 UCE E2 protein and peptide linker disposed between the RNF38 E3 RING motif and the Ubc7 UCE E2 protein is designated SEQ ID No. 31:

```
atgcaacttccttcttatcggttcaatcctaacaaccaccagtcagaaca gactttgtgtgtagtatgcatgtgtgatttgagtcaaggcagctactta gagtcttaccctgtaaccacgagttccatgccaagtgtgttgacaaatgg cttaaggcaaatcgtacttgcccaatttgccgagctgatgcttcagaagt gcatcgggattcagaaggtaccggatcccatatggcggggaccgcgctca agaggctgatggccgagtacaaacaattaacactgaatcctccggaagga attgtagcaggccccatgaatgaagagaacttttttgaatgggaggcatt gatcatgggcccagaagacacctgctttgagtttggtgtttttcctgcca tcctgagtttcccacttgattacccgttaagtccccaaagatgagattt acctgtgagatgtttcatcccaacatctaccctgatgggagagtctgcat ttccatcctccacgcgccaggcgatgacccatgggctacgagagcagcg cggagcggtggagtcctgtgcagagtgtggagaagatcctgctgtcggtg gtgagcatgctggcagagcccaatgacgaaagtggagctaacgtggatgc gtccaaaatgtggcgcgatgaccgggagcagttctataagattgccaagc agatcgtccagaagtctctgggactgtga
```

SEQ ID No. 31 is inserted into an expression vector as described in Example 1, expressed and purified as described in Example 3. The resulting isolated E3 RING:E2 fusion protein is assayed for ubiquitylation activity as described in Examples 4 and 5.

Example 10

A fusion protein including the E3 RING sequence motif of TEB4 and the E2 Ubc7 protein is constructed as described in Example 1.

The amino acid sequence of E3 RING motif of TEB4 is designated SEQ ID No. 32:

```
CRVCRSEGTPEKPLYHPCVCTGSIKFIHQECLVQWLKHSRKEYCELC
```

A cDNA sequence encoding the E3 RING motif of TEB4 is designated SEQ ID No. 33:

```
tgtagagtgtgtcggtcagaaggaacacctgagaaaccgctttatcatcc ttgtgtatgtactggcagtattaagtttatccatcaagaatgcttagttc aatggctgaaacacagtcgaaaagaatactgtgaattatgc
```

The amino acid sequence of E3 RING motif of TEB4 and additional TEB4 sequences is designated SEQ ID No. 34:

```
MDTAEEDICRVCRSEGTPEKPLYHPCVCTGSIKFIHQECLVQWLKHSRKE
YCELCKHRFAFTPIYSPDDSSGRIVTD.
```

A cDNA sequence encoding the E3 RING motif of TEB4 and additional TEB4 sequences is designated SEQ ID No. 35:

```
atggacaccgcggaggaagatatatgtagagtgtgtcggtcagaaggaac
acctgagaaaccgctttatcatccttgtgtatgtactggcagtattaagt
ttatccatcaagaatgcttagttcaatggctgaaacacagtcgaaagaa
tactgtgaattatgcaagcacagatttgcttttacaccaatttattctcc
agatgactcgagcggccgcatcgtgactgac
```

The amino acid sequence of a fusion protein including the TEB4 E3 RING motif, Ubc7 UCE E2 protein and peptide linker disposed between the TEB4 E3 RING motif and the Ubc7 UCE E2 protein is designated SEQ ID No. 36:

```
MDTAEEDICRVCRSEGTPEKPLYHPCVCTGSIKFIHQECLVQWLKHSRKE
YCELCKHRFAFTPIYSPDDSSGRIVTDGTGSHMAGTALKRLMAEYKQLTL
NPPEGIVAGPMNEENFFEWEALIMGPEDTCFEFGVFPAILSFPLDYPLSP
PKMRFTCEMFHPNIYPDGRVCISILHAPGDDPMGYESSAERWSPVQSVEK
ILLSVVSMLAEPNDESGANVDASKMWRDDREQFYKIAKQIVQKSLGL
```

A cDNA sequence encoding a fusion protein including the E3 RING motif of TEB4, Ubc7 UCE E2 protein and peptide linker disposed between the TEB4 E3 RING motif and the Ubc7 UCE E2 protein is designated SEQ ID No. 37:

```
atggacaccgcggaggaagatatatgtagagtgtgtcggtcagaaggaac
acctgagaaaccgctttatcatccttgtgtatgtactggcagtattaagt
ttatccatcaagaatgcttagttcaatggctgaaacacagtcgaaagaa
tactgtgaattatgcaagcacagatttgcttttacaccaatttattctcc
agatgactcgagcggccgcatcgtgactgacggtaccggatcccatatgg
cggggaccgcgctcaagaggctgatggccgagtacaaacaattaacactg
aatcctccggaaggaattgtagcaggcccatgaatgaagagaactttt
tgaatgggaggcattgatcatgggcccagaagacacctgctttgagtttg
gtgttttcctgccatcctgagtttcccacttgattacccgttaagtccc
ccaaagatgagatttacctgtgagatgtttcatcccaacatctaccctga
tgggagagtctgcatttccatcctccacgcgccaggcgatgacccatgg
gctacgagagcagcgcggagcggtggagtcctgtgcagagtgtggagaag
atcctgctgtcggtggtgagcatgctggcagagcccaatgacgaaagtgg
agctaacgtggatgcgtccaaaatgtggcgcgatgaccgggagcagttct
ataagattgccaagcagatcgtccagaagtctctgggactgtga
```

SEQ ID No. 37 is inserted into an expression vector as described in Example 1, expressed and purified as described in Example 3. The resulting isolated E3 RING:E2 fusion protein is assayed for ubiquitylation activity as described in Examples 4 and 5.

Example 11

A fusion protein including the E3 RING sequence motif of RNF139 (trc8) and the E2 Ubc7 protein is constructed as described in Example 1.

The amino acid sequence of E3 RING motif of RNF139 (trc8) is designated SEQ ID No. 38:

```
CAICYHEFTTSARITPCNHYFHALCLRKWLYIQDTCPMC
```

A cDNA sequence encoding the E3 RING motif of RNF139 (trc8) is designated SEQ ID No. 39:

```
tgtgcaatctgctatcatgagtttacaacatctgctcgtattacaccgtg
taatcattatttccatgcactttgccttcggaaatggctgtacattcaag
atacttgtccaatgtgc
```

The amino acid sequence of E3 RING motif of RNF139 (trc8) and additional RNF139 sequences is designated SEQ ID No. 40:

```
MINSLPEIKGSRLQEINDVCAICYHEFTTSARITPCNHYFHALCLRKWLY
IQDTCPMCHQKVYIEDDIKDNS.
```

A cDNA sequence encoding the E3 RING motif of RNF139 (trc8) and additional RNF139 sequences is designated SEQ ID No. 41:

```
atgattaattcacttcctgaaataaaagggagccgcttacaagaaataaa
tgatgtatgtgcaatctgctatcatgagtttacaacatctgctcgtatta
caccgtgtaatcattatttccatgtactttgccttcggaaatggctgtac
attcaagatacttgtccaatgtgccatcagaaagtatacatcgaagatga
tatcaaggataattca
```

The amino acid sequence of a fusion protein including the RNF139 (trc8) E3 RING motif, Ubc7 UCE E2 protein and peptide linker disposed between the RNF139 (trc8) E3 RING motif and the Ubc7 UCE E2 protein is designated SEQ ID No. 42:

```
MINSLPEIKGSRLQEINDVCAICYHEFTTSARITPCNHYFHALCLRKWLY
IQDTCPMCHQKVYIEDDIKDNSGTGSHMAGTALKRLMAEYKQLTLNPPEG
IVAGPMNEENFFEWEALIMGPEDTCFEFGVFPAILSFPLDYPLSPPKMRF
TCEMFHPNIYPDGRVCISILHAPGDDPMGYESSAERWSPVQSVEKILLSV
VSMLAEPNDESGANVDASKMWRDDREQFYKIAKQIVQKSLGL
```

A cDNA sequence encoding a fusion protein including the E3 RING motif of RNF139 (trc8), Ubc7 UCE E2 protein and peptide linker disposed between the RNF139 (trc8) E3 RING motif and the Ubc7 UCE E2 protein is designated SEQ ID No. 43:

```
atgattaattcacttcctgaaataaaagggagccgcttacaagaaataaa tgatgtatgtgcaatctgctatcatgagtttacaacatctgctcgtatta caccgtgtaatcattatttccatgcactttgccttcggaaatggctgtac attcaagatacttgtccaatgtgccatcagaaagtatacatcgaagatga tatcaaggataattcaggtaccggatcccatatggcggggaccgcgctca agaggctgatggccgagtacaaacaattaacactgaatcctccggaagga attgtagcaggcccatgaatgaagagaacttttttgaatgggaggcatt gatcatgggcccagaagacacctgctttgagtttggtgttttcctgcca tcctgagtttcccacttgattaccgttaagtcccccaaagatgagattt acctgtgagatgtttcatcccaacatctaccctgatgggagagtctgcat ttccatcctccacgcgccaggcgatgacccatgggctacgagagcagcg cggagcggtggagtcctgtgcagagtgtggagaagatcctgctgtcggtg gtgagcatgctggcagagcccaatgacgaaagtggagctaacgtggatgc gtccaaaatgtggcgcgatgaccgggagcagttctataagattgccaagc agatcgtccagaagtctctgggactgtga
```

SEQ ID No. 43 is inserted into an expression vector as described in Example 1, expressed and purified as described in Example 3. The resulting isolated E3 RING:E2 fusion protein is assayed for ubiquitylation activity as described in Examples 4 and 5.

Example 12

A fusion protein including the E3 RING sequence motif of RNFx2 and the E2 Ubc7 protein is constructed as described in Example 1.

The amino acid sequence of E3 RING motif of RNFx2 is designated SEQ ID No. 44:

CAICLDEYEEGDQLKILPCSHTYHCKCIDPWFSQAPRRSCPVC

A cDNA sequence encoding the E3 RING motif of RNFx2 is designated SEQ ID No. 45

```
tgtgccatctgcctggatgagtacgaggagggcgaccaactcaagatcct gccctgctcccacacctaccactgcaaatgcattgacccctggttctccc aagcccccggcgtcctgccccgtgtgc
```

The amino acid sequence of E3 RING motif of RNFx2 and additional RNFx2 sequences is designated SEQ ID No. 46:

MTSTCQKAQVRTFTWHNDLCAICLDEYEEGDQLKILPCSHTYHCKCIDPW

FSQAPRRSCPVCKQSVAATEDSFDS

A cDNA sequence encoding the E3 RING motif of RNFx2 and additional RNFx2 sequences is designated SEQ ID No. 47:

```
atgacgtctacctgccagaaggcccaggtccgcaccttcacgtggcacaa cgacctgtgtgccatctgcctggatgagtacgaggagggcgaccaactca agatcctgccctgctcccacacctaccactgcaaatgcattgacccctgg ttctcccaagcccccggcgtcctgccccgtgtgcaaacagtcggtggc cgccacagaagacagctttgactcc
```

The amino acid sequence of a fusion protein including the RNFx2 E3 RING motif, Ubc7 UCE E2 protein and peptide linker disposed between the RNFx2 E3 RING motif and the Ubc7 UCE E2 protein is designated SEQ ID No. 48:

MTSTCQKAQVRTFTWHNDLCAICLDEYEEGDQLKILPCSHTYHCKCIDPW

FSQAPRRSCPVCKQSVAATEDSFDSGTGSHMAGTALKRLMAEYKQLTLNP

PEGIVAGPMNEENFFEWEALIMGPEDTCFEFGVFPAILSFPLDYPLSPPK

MRFTCEMFHPNIYPDGRVCISILHAPGDDPMGYESSAERWSPVQSVEKIL

LSVVSMLAEPNDESGANVDASKMWRDDREQFYKIAKQIVQKSLGL

A cDNA sequence encoding a fusion protein including the E3 RING motif of RNFx2, Ubc7 UCE E2 protein and peptide linker disposed between the RNFx2 E3 RING motif and the Ubc7 UCE E2 protein is designated SEQ ID No. 49:

```
atgacgtctacctgccagaaggcccaggtccgcaccttcacgtggcacaa cgacctgtgtgccatctgcctggatgagtacgaggagggcgaccaactca agatcctgccctgctcccacacctaccactgcaaatgcattgacccctgg ttctcccaagcccccggcgtcctgccccgtgtgcaaacagtcggtggc cgccacagaagacagctttgactccggtaccggatcccatatggcgggga ccgcgctcaagaggctgatggccgagtacaaacaattaacactgaatcct ccggaaggaattgtagcaggcccatgaatgaagagaacttttttgaatg ggaggcattgatcatgggcccagaagacacctgctttgagtttggtgttt ttcctgccatcctgagtttcccacttgattaccgttaagtcccccaaag atgagatttacctgtgagatgtttcatcccaacatctaccctgatgggag agtctgcatttccatcctccacgcgccaggcgatgacccatgggctacg agagcagcgcggagcggtggagtcctgtgcagagtgtggagaagatcctg ctgtcggtggtgagcatgctggcagagcccaatgacgaaagtggagctaa cgtggatgcgtccaaaatgtggcgcgatgaccgggagcagttctataaga ttgccaagcagatcgtccagaagtctctgggactgtga
```

SEQ ID No. 49 is inserted into an expression vector as described in Example 1, expressed and purified as described in Example 3. The resulting isolated E3 RING:E2 fusion protein is assayed for ubiquitylation activity as described in Examples 4 and 5.

Example 13

A fusion protein including the E3 RING sequence motif of RNF126 and the E2 Ubc7 protein is constructed as described in Example 1.

The amino acid sequence of E3 RING motif of RNF126 is designated SEQ ID No. 50:

CPVCKDDYALGERVRQLPCNHLFHDGCIVPWLEQHDSCPVC

A cDNA sequence encoding the E3 RING motif of RNF126 is designated SEQ ID No. 51:

```
tgccctgtgtgcaaggacgactacgcgctgggtgagcgtgtgcggcagct
gccctgcaaccacctgttccacgacggctgcatcgtgccctggctggagc
agcacgacagctgccccgtctgc
```

The amino acid sequence of E3 RING motif of RNF126 and additional RNF126 sequences is designated SEQ ID No. 52:

```
MQALPTVPVTEEHVGSGLECPVCKDDYALGERVRQLPCNHLFHDGCIVPW
LEQHDSCPVCRKSLTGQNTATN
```

A cDNA sequence encoding the E3 RING motif of RNF126 and additional RNF126 sequences is designated SEQ ID No. 53:

```
atgcaggccctccccaccgtcccgtcactgaggagcacgtaggctccgg
gctcgagtgccctgtgtgcaaggacgactacgcgctgggtgagcgtgtgc
ggcagctgccctgcaaccacctgttccacgacggctgcatcgtgccctgg
ctggagcagcacgacagctgccccgtctgccgaaaaagcctcacgggaca
gaacacggccacgaac
```

The amino acid sequence of a fusion protein including the RNF126 RING motif, Ubc7 UCE E2 protein and peptide linker disposed between the RNF126 RING motif and the Ubc7 UCE E2 protein is designated SEQ ID No. 54:

```
MQALPTVPVTEEHVGSGLECPVCKDDYALGERVRQLPCNHLFHDGCIVPW
LEQHDSCPVCRKSLTGQNTATNGTGSHMAGTALKRLMAEYKQLTLNPPEG
IVAGPMNEENFFEWEALIMGPEDTCFEFGVFPAILSFPLDYPLSPPKMRF
TCEMFHPNIYPDGRVCISILHAPGDDPMGYESSAERWSPVQSVEKILLSV
VSMLAEPNDLSGANVDASKMWRDDREQFYKIAKQIVQKSLGL
```

A cDNA sequence encoding a fusion protein including the E3 RING motif of RNF126, Ubc7 UCE E2 protein and peptide linker disposed between the RNF126 E3 RING motif and the Ubc7 UCE E2 protein is designated SEQ ID No. 55:

```
atgcaggccctccccaccgtcccgtcactgaggagcacgtaggctccgg
gctcgagtgccctgtgtgcaaggacgactacgcgctgggtgagcgtgtgc
ggcagctgccctgcaaccacctgttccacgacggctgcatcgtgccctgg
ctggagcagcacgacagctgccccgtctgccgaaaaagcctcacgggaca
gaacacggccacgaacggtaccggatccatatggcggggaccgcgctca
agaggctgatggccgagtacaaacaattaacactgaatcctccggaagga
attgtagcaggcccatgaatgaagagaacttttttgaatgggaggcatt
gatcatgggcccagaagacacctgctttgagtttggtgttttcctgcca
tcctgagtttcccacttgattaccgttaagtcccccaaagatgagattt
acctgtgagatgtttcatcccaacatctaccctgatgggagagtctgcat
ttccatcctccacgcgccaggcgatgaccccatgggctacgagagcagcg
cggagcggtggagtcctgtgcagagtgtggagaagatcctgctgtcggtg
gtgagcatgctggcagagcccaatgacgaaagtggagctaacgtggatgc
gtccaaaatgtggcgcgatgaccgggagcagttctataagattgccaagc
agatcgtccagaagtctctgggactgtga
```

SEQ ID No. 55 is inserted into an expression vector as described in Example 1, expressed and purified as described in Example 3. The resulting isolated E3 RING:E2 fusion protein is assayed for ubiquitylation activity as described in Examples 4 and 5.

Example 14

A fusion protein including the E3 RING sequence motif of Hrd1 and the E2 Ubc7 protein is constructed as described in Example 1.

The amino acid sequence of E3 RING motif of Hrd1 is designated SEQ ID No. 56:

```
CIICREEMVTGAKRLPCNHIFHTSCLRSWFQRQQTCPTC
```

The cDNA sequence of the E3 RING motif of Hrd1 is designated SEQ ID No. 57:

```
tgcatcatctgccgagaagagatggtgactggtgccaagagactgccctg
caaccacatttccataccagctgcctgcgctcctggttccagcggcagc
agacctgccccacctgc
```

The amino acid sequence of E3 RING motif of Hrd1 and additional Hrd1 sequences is designated SEQ ID No. 58

```
MNTLYPDATPEELQAMDNVCIICREEMVTGAKRLPCNHIFHTSCLRSWFQ
RQQTCPTCRMDVLRASLPAQSP
```

A cDNA sequence encoding the E3 RING motif and additional sequences of Hrd1 is designated SEQ ID No. 59:

```
atgaacaccctgtatccagatgccacccagaggagctccaggcaatgga
caatgtctgcatcatctgccgagaagagatggtgactggtgccaagagac
tgccctgcaaccacatttccataccagctgcctgcgctcctggttccag
cggcagcagacctgccccacctgccgtatggatgtccttcgtgcatcgct
gccagcgcagtcacca
```

An amino acid sequence of a fusion protein including the Hrd1 RING motif, Ubc7 UCE E2 protein and peptide linker disposed between the Hrd1 RING motif and the Ubc7 UCE E2 protein is designated SEQ ID No. 60:

```
MNTLYPDATPEELQAMDNVCIICREEMVTGAKRLPCNHIFHTSCLRSWFQ
RQQTCPTCRMDVLRASLPAQSPGTGSHMAGTALKRLMAEYKQLTLNPPEG
IVAGPMNEENFFEWEALIMGPEDTCFEFGVFPAILSFPLDYPLSPPKMRF
TCEMFHPNIYPDGRVCISILHAPGDDPMGYESSAERWSPVQSVEKILLSV
VSMLAEPNDESGANVDASKMWRDDREQFYKIAKQIVQKSLGL
```

A cDNA sequence encoding a fusion protein including the E3 RING motif of Hrd1, Ubc7 UCE E2 protein and peptide linker disposed between the Hrd1 E3 RING motif and the Ubc7 UCE E2 protein is designated SEQ ID No. 61:

atgaaccccctgtatccagatgccaccccagaggagctccaggcaatgga caatgtctgcatcatctgccgagaagagatggtgactggtgccaagagac tgccctgcaaccacatttccataccagctgcctgcgctcctggttccag cggcagcagacctgccccacctgccgtatggatgtccttcgtgcatcgct gccagcgcagtcaccaggtaccggatcccatatggcggggaccgcgctca agaggctgatggccgagtacaaacaattaacactgaatcctccggaagga attgtagcaggccccatgaatgaagagaacttttttgaatgggaggcatt gatcatgggcccagaagacacctgctttgagtttggtgttttcctgcca tcctgagtttcccacttgattacccgttaagtcccccaaagatgagattt acctgtgagatgtttcatcccaacatctaccctgatgggagagtctgcat ttccatcctccacgcgccaggcgatgacccatgggctacgagagcagcg cggagcggtggagtcctgtgcagagtgtgagaagatcctgctgtcggtg gtgagcatgctggcagagcccaatgacgaaagtggagctaacgtggatgc gtccaaaatgtggcgcgatgaccgggagcagttctataagattgccaagc agatcgtccagaagtctctgggactgtga SEQ ID No. 61 is inserted into an expression vector as described in Example 1, expressed and purified as described in Example 3. The resulting isolated E3 RING:E2 fusion protein is assayed for ubiquitylation activity as described in Examples 4 and 5.

Example 15

A fusion protein including the E3 RING sequence motif of MARCH1 and the E2 Ubc7 protein is constructed as described in Example 1.

The amino acid sequence of E3 RING motif of MARCH1 is designated SEQ ID No. 62:

CRICHCEGDEESPLITPCRCTGTLRFVHQSCLHQWIKSSDTRCCELC

A cDNA sequence encoding the E3 RING motif of MARCH1 is designated SEQ ID No. 63:

tgcagaatctgtcactgcgaaggggatgaagagagccccctcatcacacc ctgtcgctgcactgggacactgcgctttgtccaccagtcctgcctccacc agtggataaagagctcagatacacgctgctgtgagctctgc The amino acid sequence of the E3 RING motif of MARCH1 and additional MARCH1 sequences is designated SEQ ID No. 64:

MAPRSQSRLSVCPSTQDICRICHCEGDEESPLITPCRCTGTLRFVHQSCL

HQWIKSSDTRCCELCKYDFIMETKLK

A cDNA sequence encoding the E3 RING motif of MARCH1 and additional MARCH1 sequences is designated SEQ ID No. 65:

atggctcccaggagccagtcaaggttgtctgtctgtccatccactcagga catctgcagaatctgtcactgcgaaggggatgaagagagccccctcatca caccctgtcgctgcactgggacactgcgctttgtccaccagtcctgcctc caccagtggataaagagctcagatacacgctgctgtgagctctgcaagta tgacttcataatggagaccaagctcaaa An amino acid sequence of a fusion protein including the MARCH1 RING motif, Ubc7 UCE E2 protein and peptide linker disposed between the MARCH1 RING motif and the Ubc7 UCE E2 protein is designated SEQ ID No. 66:

MAPRSQSRLSVCPSTQDICRICHCEGDEESPLITPCRCTGTLRFVHQSCL

HQWIKSSDTRCCELCKYDFIMETKLKGTGSHMAGTALKRLMAEYKQLTLN

PPEGIVAGPMNEENFFEWEALIMGPEDTCFEFGVFPAILSFPLDYPLSPP

KMRFTCEMFHPNIYPDGRVCISILHAPGDDPMGYESSAERWSPVQSVEKI

LLSVVSMLAEPNDESGANVDASKMWRDDREQFYKIAKQIVQKSLGL

A cDNA sequence encoding a fusion protein including the E3 RING motif of MARCH1, Ubc7 UCE E2 protein and peptide linker disposed between the MARCH1 E3 RING motif and the Ubc7 UCE E2 protein is designated SEQ ID No. 67:

atggctcccaggagccagtcaaggttgtctgtctgtccatccactcagga catctgcagaatctgtcactgcgaaggggatgaagagagccccctcatca caccctgtcgctgcactgggacactgcgctttgtccaccagtcctgcctc caccagtggataaagagctcagatacacgctgctgtgagctctgcaagta tgacttcataatggagaccaagctcaaaggtaccggatcccatatggcgg ggaccgcgctcaagaggctgatggccgagtacaaacaattaacactgaat cctccggaaggaattgtagcaggccccatgaatgaagagaacttttttga atgggaggcattgatcatgggcccagaagacacctgctttgagtttggtg ttttcctgccatcctgagtttcccacttgattacccgttaagtccccca aagatgagatttacctgtgagatgtttcatcccaacatctaccctgatgg gagagtctgcatttccatcctccacgcgccaggcgatgacccatgggct acgagagcagcgcggagcggtggagtcctgtgcagagtgtgagaagatc ctgctgtcggtggtgagcatgctggcagagcccaatgacgaaagtggagc taacgtggatgcgtccaaaatgtggcgcgatgaccgggagcagttctata agattgccaagcagatcgtccagaagtctctgggactgtga SEQ ID No. 67 is inserted into an expression vector as described in Example 1, expressed and purified as described in Example 3. The resulting isolated E3 RING:E2 fusion protein is assayed for ubiquitylation activity as described in Examples 4 and 5.

Example 16

Ubiquitylation Assay
Activity of E3 RING:E2 fusion proteins as measured by Ub dimer ($Ub_2$) formation under steady-state conditions.
FIG. 8A schematically illustrates a reaction where E2~Ub is formed with the UbK48R mutant replacing ubiquitin (Ub), the E2~UbK48R is stable since the thiolester-linked UbK48R cannot be transferred to UbK48R to form K48-specific Ub dimer. When the reaction mixture also contain Ub74, where the C-terminal Gly-Gly sequence in Ub is not present, the thiolester-linked UbK48R can be transferred to K48 present in Ub74, resulting in the formation of a UbK48R-Ub74 dimer (Ub$_2$). This Ub$_2$ lacks the free C-terminal Gly residue in wild type Ub dimer and is therefore unable to form thiolester linkage with E2. Likewise, this Ub$_2$ lacks the free K48 residue in a wild type ubiquitin dimer and is therefore unable to accept the transfer of UbK48R to foam trimeric ubiquitin. The formation of Ub$_2$ can be used to follow the activity of E2 or RING-E2 fusion protein.

Reactions are carried out in 25 mM Tris, pH 7.6, containing 1 mM ATP, 10 mM MgCl$_2$, 0.1 mM DTT, 0.25 µM E1, 1 µM of either gp78-Ubc7 or Ubc7, 20 µM of a C-terminally truncated ubiquitin where the C-terminal Gly-Gly sequence in ubiquitin is absent (Ub74), and 20 µM of a modified UbK48R mutant. This modified UbK48R mutant is extended at the N-terminus by a MCHHHHHH sequence where the cysteine residue had been modified with Oregon Green iodoacetamide (Invitrogen). At specified times indicated, aliquots are withdrawn into SDS-sample buffer, subjected to SDS-PAGE, and protein species containing the modified UbK48R is visualized by using a fluorescent imager using excitation wavelength of 488 nm and emission of light at >510 nm.

Figures 8B, 8C:
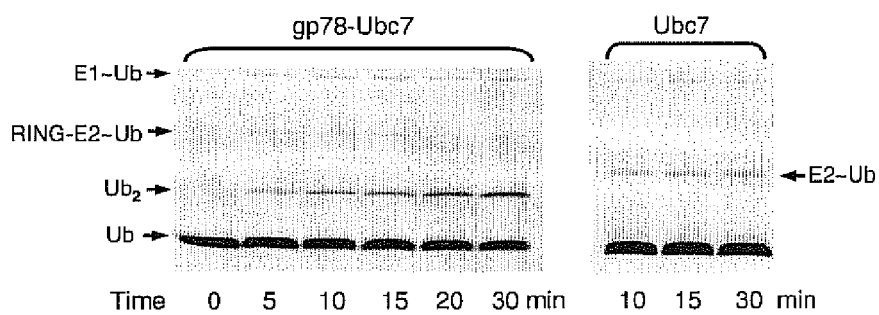
FIG. 8B shows an SDS-PAGE imaged with a fluorescent imager and showing results of an activity assay using the indicated fusion protein of the present invention.
FIG. 8C shows an SDS-PAGE imaged with a fluorescent imager and showing results of an activity assay using unmodified E2 Ubc7.

FIG. 8B shows an SDS-PAGE imaged with a fluorescent imager and showing results of an activity assay using the indicated 78-Ubc7 fusion protein of the present invention.

FIG. 8C shows an SDS-PAGE imaged with a fluorescent imager and showing results of an activity assay using unmodified E2 Ubc7.

Example 17

A fusion protein including the E3 RING sequence motif of gp78 and the E2-25K protein is constructed as described in Example 1.

An amino acid sequence of a fusion protein including the gp78 RING motif, UCE E2-25K protein and peptide linker disposed between the gp78 RING motif and the UCE E2-25K protein is designated SEQ ID No. 75:

MEARFAVATPEELAVNNDDCAICWDSMQAARKLPCGHLFHNSCLRSWLEQ

DTSCPTCRMSLNIADNNRVREEGTGSHMANIAVQRIKREFKEVLKSEETS

KNQIKVDLVDENFTELRGEIAGPPDTPYEGGRYQLEIKIPETYPFNPPKV

RFITKIWHPNISSVTGAICLDILKDQWAAMTLRTVLLSLQALLAAAEPDD

PQDAVVANQYKQNPEMFKQTARLWAHVYAGAPVSSPEYTKKIENLCAMGF

DPNAVIVALSSKSWDVETATELLLSN

A cDNA sequence encoding a fusion protein including the E3 RING motif of gp78, UCE E2-25K protein and peptide linker disposed between the E3 RING motif of gp78 and UCE E2-25K protein is designated SEQ ID No. 71:

atggaggccaggtttgcattgcaactccagaggagctggctgtcaacaat gacgactgtgccatctgtttgggactccatgcaggctgcgcggaaactgc ctgtggacatcttttccacaactcctgtcttcgttcctggctagaacaag acacctcctgtccaacatgcagaatgtctcttaatattgccgacaataat cgtgtcagggaagaaggtaccggatcccatatggccaacatcgcggtgca gcgaatcaagcgggagttcaaggaggtgctgaagagcgaggagacgagca aaaatcaaattaaagtagatcttgtagatgagaattttacagaattaaga ggagaaatagcaggacctccagacacaccatatgaaggaggaagatacca actagagataaaaataccagaaacatacccatttaatccccctaaggtcc ggtttatcactaaaatatggcatcctaatattagttccgtcacaggggct atttgtttggatatcctgaaagatcaatgggcagctgcaatgactctccg cacggtattattgtcattgcaagcactattggcagctgcagagccagatg atccacaggatgctgtagtagcaaatcagtacaaacaaaatcccgaaatg ttcaaacagacagctcgactttgggcacatgtgtatgctggagcaccagt ttctagtccagaatacaccaaaaaaatagaaaacctatgtgctatgggct ttgataggaatgcagtaatagtggccttgtcttcaaaatcatgggatgta gagactgcaacagaattgcttctgagtaactga SEQ ID No. 71 is inserted into an expression vector as described in Example 1, expressed and purified as described in Example 3. The resulting isolated E3 RING:E2 fusion protein is assayed for ubiquitylation activity as described in Examples 4 and 5.

Example 18

E3 RING:E2:Ubiquitylation Substrate Fusion Protein and Assay

A fusion protein including the E3 RING sequence motif of gp78, the E2 Ubc7 protein and ubiquitin is constructed essentially as described in Example 1.

An amino acid sequence of a fusion protein including the gp78 RING motif, UCE E2 Ubc7 protein, peptide linker disposed between the gp78 RING motif and the UCE E2 Ubc7 protein and ubiquitin is designated SEQ ID No. 72:

MEARFAVATPEELAVNNDDCAICWDSMQAARKLPCGHLFHNSCLRSWLEQ

DTSCPTCPMSLNIADNNRVREEGTGSHMAGTALKRLMAEYKQLTLNPPEG

IVAGPMNEENFFEWEALIMGPEDTCFEFGVFPAILSFPLDYPLSPPKMRF

TCEMFHPNIYPDGRVCISILHAPGDDPMGYESSAERWSPVQSVEKILLSV

VSMLAEPNDESGANVDASKMWRDDREQFYKIAKQIVQKSLGLLKLGTGAS

GTSGSGMQIFVKTLTGKTITLEVEPSDTIENVKAKIQDKEGIPPDQQRLI

FAGKQLEDGRTLSDYNIQKESTLHLVLRLRGG

A cDNA sequence encoding a fusion protein including the gp78 RING motif, UCE E2 Ubc7 protein, peptide linker disposed between the gp78 RING motif and the UCE E2 Ubc7 protein and ubiquitin is designated SEQ ID No. 73:

atggaggccaggtttgcagttgcaactccagaggagctggctgtcaacaa tgacgactgtgccatctgtttgggactccatgcaggctgcgcggaaactgc cctgtggacatcttttccacaactcctgtcttcgttcctggctagaacaa gacacctcctgtccaacatgcagaatgtctcttaatattgccgacaataa tcgtgtcagggaagaaggtaccggatcccatatggcggggaccgcgctca -continued

```
agaggctgatggccgagtacaaacaattaacactgaatcctccggaagga attgtagcaggcccccatgaatgaagagaacttttttgaatgggaggcatt gatcatgggcccagaagacacctgctttgagtttggtgttttcctgcca tcctgagtttcccacttgattacccgttaagtcccccaaagatgagattt acctgtgagatgtttcatcccaacatctaccctgatgggagagtctgcat ttccatcctccacgcgccaggcgatgaccccatgggctacgagagcagcg cggagcggtggagtcctgtgcagagtgtggagaagatcctgctgtcggtg gtgagcatgctggcagagcccaatgacgaaagtggagctaacgtggatgc gtccaaaatgtggcgcgatgaccgggagcagttctataagattgccaagc agatcgtccagaagtctctgggactgttaaagcttggcaccggcgctagc ggcactagtggaagtggaatgcagatcttcgtcaagacgttaaccggtaa aaccataactctagaagttgaaccatccgataccatcgaaaacgttaagg ctaaaattcaagacaaggaaggcattccacctgatcaacaaagattgatc
```

```
tttgccggtaagcagctcgaggacggtagaacgctgtctgattacaacat tcagaaggagtcgaccttacatcttgtcttaagactaagaggtggt
```

SEQ ID No. 73 is inserted into an expression vector as described in Example 1, expressed and purified as described in Example 3. The resulting isolated E3 RING:E2 fusion protein is assayed for ubiquitylation activity.

Figure 9:
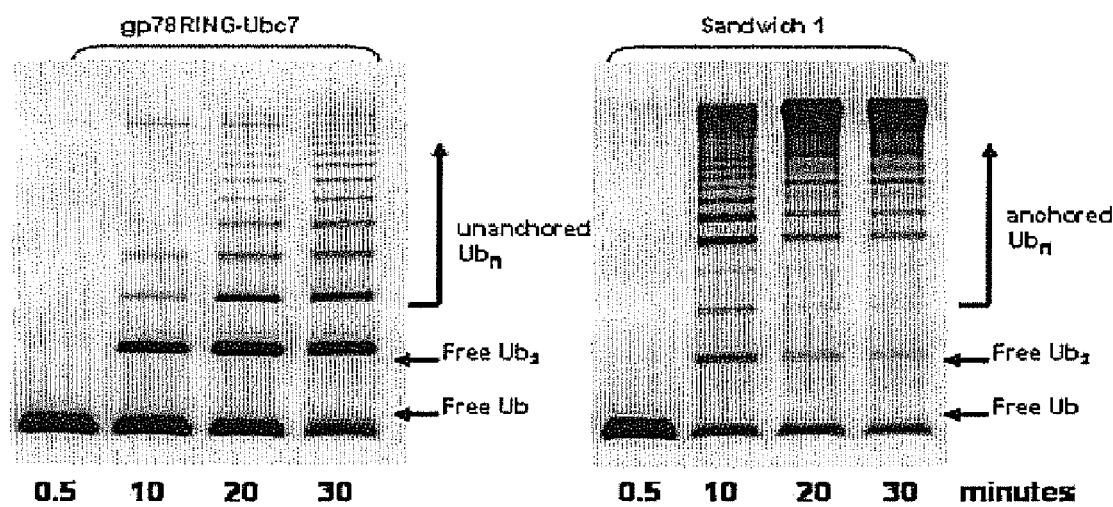
FIG. 9 shows an SDS-PAGE indicating results of the activity assay reactions carried out either with 0.1 µM gp78RING-Ubc7 or with gp78RING-Ubc7-Ub in reaction conditions otherwise identical to those used in FIG. 7.

FIG. 9 shows results of reactions carried out either with 0.1 µM gp78RING-Ubc7 or with gp78RING-Ubc7-Ub in reaction conditions otherwise identical to those used for reactions shown in FIG. 7.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A composition, comprising:
a fusion protein comprising an ubiquitin ligase RING motif $CXXC(X)_{n1}CX(H/C)(X)_{n2}(H/C)XXC(X)_{n3}CXXC$, where C is a cysteine, H is a histidine, n1 is in the range of 11-14, inclusive, n2 is in the range of 2-7, inclusive and n3 is in the range of 10-20, inclusive, and X is any amino acid, wherein the ubiquitin ligase RING motif has at least 90% identity to an ubiquitin ligase RING motif selected from the group consisting of: SEQ ID NO: 8, SEQ ID NO: 14, SEQ ID NO: 20, SEQ ID NO: 26, SEQ ID NO: 32, SEQ ID NO: 38, SEQ ID NO: 44, SEQ ID NO: 50, SEQ ID NO: 56 and SEQ ID NO: 62; fused to an ubiquitin conjugating enzyme which has at least 90% identity to an ubiquitin conjugating enzyme selected from the group consisting of: SEQ ID NO: 1, SEQ ID NO: 3, SEQ ID NO: 5 and SEQ ID NO: 69, the fusion protein active to transfer ubiquitin to a ubiquitylation substrate in a ubiquitinylation reaction.

2. The composition of claim 1 wherein the fusion protein further comprises ubiquitin.

3. A method of identifying a modulator of ubiquitylation, comprising:
contacting the fusion protein of claim 1 and a ubiquitylation substrate in the presence of a test substance; and
detecting ubiquitylation of the ubiquitylation substrate.

4. The method of claim 3, further comprising:
contacting the fusion protein with a ubiquitylation substrate in the absence of the test substance;

comparing ubiquitylation of the ubiquitylation substrate in the presence and absence of the test substance, thereby identifying a modulator of ubiquitylation.

5. The method of claim 3, wherein the ubiquitylation substrate comprises a first mutant ubiquitin, the first mutant ubiquitin having a substitution mutation at K48, where any amino acid other than lysine is substituted for lysine.

6. The method of claim 5, wherein the first mutant ubiquitin having a substitution mutation at K48 is K48R, where arginine is substituted for lysine.

7. The method of claim 5, further comprising a second mutant ubiquitin, wherein the second mutant ubiquitin is unable to form a thiolester linkage with a UCE E2 protein due to substitution, truncation or extension at the C-terminus of ubiquitin.

8. The method of claim 7, wherein the second mutant ubiquitin is C-terminus truncated ubiquitin Ub74.

9. A composition comprising a nucleotide sequence encoding the fusion protein according to claim 1.

10. A host cell comprising the nucleotide sequence according to claim 9.

11. A vector comprising the nucleotide sequence according to claim 9.

* * * * *

UNITED STATES PATENT AND TRADEMARK OFFICE
CERTIFICATE OF CORRECTION

PATENT NO.        : 8,273,540 B2
APPLICATION NO.   : 12/576704
DATED             : September 25, 2012
INVENTOR(S)       : Vincent Chau et al.

It is certified that error appears in the above-identified patent and that said Letters Patent is hereby corrected as shown below:

In the Specifications

Col. 12, line 59: replace ")(BLAST" with --XBLAST--;

Col. 35, line 11: replace "to foam" with --to form--;

Col. 35, line 29: replace "indicated 78-UBC7" with --indicated gp 78-UBC7--;

In the Claims

Col. 104, line 9: replace "a host cell" with --an isolated host cell--.

Signed and Sealed this
Ninth Day of July, 2013

Teresa Stanek Rea
*Acting Director of the United States Patent and Trademark Office*